(12) United States Patent
Tsukada et al.

(10) Patent No.: US 7,566,128 B2
(45) Date of Patent: Jul. 28, 2009

(54) FUNDUS OBSERVATION DEVICE, FUNDUS IMAGE DISPLAY DEVICE AND FUNDUS OBSERVATION PROGRAM

(75) Inventors: Hisashi Tsukada, Tokyo (JP); Koki Harumoto, Tokyo (JP); Hiroyuki Aoki, Tokyo (JP); Tsutomu Kikawa, Tokyo (JP); Yasufumi Fukuma, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 183 days.

(21) Appl. No.: 11/521,360

(22) Filed: Sep. 15, 2006

(65) Prior Publication Data

US 2007/0070295 A1    Mar. 29, 2007

(30) Foreign Application Priority Data

Sep. 29, 2005  (JP)  ............................. 2005-284622
Jun. 7, 2006   (JP)  ............................. 2006-157928

(51) Int. Cl.
*A61B 3/10*  (2006.01)
(52) U.S. Cl. ....................... 351/205; 351/221
(58) Field of Classification Search ......... 351/205–206, 351/221; 354/62
See application file for complete search history.

(56) References Cited

U.S. PATENT DOCUMENTS 5,975,697 A * 11/1999 Podoleanu et al. .......... 351/206
2003/0053072 A1  3/2003  Fercher et al.
2005/0020925 A1  1/2005  Kleen et al.

FOREIGN PATENT DOCUMENTS

| EP | 1650528 A | 4/2006 |
|---|---|---|
| JP | 2003-543 | 1/2003 |
| JP | 2004-350849 | 12/2004 |
| JP | 2005-241464 | 9/2005 |

OTHER PUBLICATIONS

European Search Report for Application No. 06020267.8, mailed Oct. 26, 2007.
Shuliang Jiao et al: "Simultaneous Acquisition of Sectional Fundus Opthamalic Images With Spectral-Domain Optical Coherence Tomography", Optics Express, Optical Society of America, Washington, DC, US, vol. 13, No. 2, Jan. 24, 2005, pp. 444-452.

* cited by examiner

*Primary Examiner*—Scott J Sugarman
*Assistant Examiner*—Dawayne A Pinkney
(74) *Attorney, Agent, or Firm*—Edwards Angell Palmer & Dodge LLP

(57) ABSTRACT

To provide a technology that makes it easy to capture a positional relation of a 2-dimensional image of the surface of a fundus oculi and a tomographic image of the fundus oculi. The fundus observation device 1 is provided with a fundus camera unit 1A for forming a 2-dimensional image of the surface of a fundus oculi Ef of an eye to be examined, an OCT unit 150 for forming a tomographic image of the fundus oculi Ef, a scanning unit 141 as well as an image processing part 220, a display 207, and a controlling part 210 of a computer 200 for displaying the 2-dimensional image formed by the fundus camera unit 1A and a tomographic image formed by the OCT unit, etc. in parallel on the display 207, and also for displaying the cross-sectional position information (attention line L, attention region P) indicating the cross-sectional position of the tomographic image on the surface of the fundus oculi Ef, so as to be overlapped with the 2-dimensional image.

36 Claims, 32 Drawing Sheets

3-DIMENSIONAL PARTIAL IMAGE
GP'

FUNDUS OBSERVATION DEVICE, FUNDUS IMAGE DISPLAY DEVICE AND FUNDUS OBSERVATION PROGRAM

BACKGROUND OF THE INVENTION

1. Field of the Invention

The present invention relates to a fundus observation device, a fundus image display device and a fundus observation program for observing the state of the fundus oculi of an eye to be examined.

2. Description of the Related Art

As a fundus observation device, conventionally a fundus camera has been widely used. FIG. 42 shows one example of the appearance of a conventional fundus camera in general, and FIG. 43 shows one example of an optical system composition to be internally accommodated therein (e.g. ref. JP Patent laid-open No. 2004-350849). Furthermore, "observation" is intended to include at least a case in which photographic images are observed (observations with the naked eye may be included).

First, referring to FIG. 42, an explanation is made regarding the appearance of a conventional fundus camera 1000. This fundus camera is provided with a platform 3 mounted on a base 2 slidably in the front and rear, right and left (horizontal direction) directions. On this platform 3, an operation panel and a joystick 4 are installed for an examiner to conduct various operations.

The examiner may place the platform 3 on the base 2 to be moved freely by operating the joystick 4. On the top of the joystick, an operation button 4a is installed to be pressed down to photograph fundus oculi images.

On the base 2, a post 5 is installed standing upwards. On the post 5, a jaw rest 6 where the jaw of a patient is to be rested and an external fixation lamp 7 as a light source for fixing an eye to be examined E are provided.

On the platform 3, a main body part 8 is installed to accommodate various optical systems or control systems of the fundus camera 1000. Furthermore, the control system may be installed inside the base 2 or the platform, etc., or in an external device such as a computer, etc. connected to the fundus camera 1000.

On the side of the eye to be examined E of the main body part 8, an objective lens part 8a disposed opposite to the eye to be examined E is installed, and on the examiner side, an eyepiece part 8b is installed.

Furthermore, connected to the main body part 8 is a still camera 9 for photographing a still image of a fundus oculi of the eye to be examined E and an imaging device 10 such as a TV camera, etc. for photographing still images or moving images of a fundus oculi. The still camera 9 and the imaging device 10 are formed removably with respect to the main body part 8.

As a still camera 9, in accordance with various conditions such as the purpose of an examination or the saving method of photographed images, etc., a digital camera equipped with CCD, a film camera, an instant camera, etc. may interchangeably be used when it is appropriate. The main body part 8 is equipped with a mounting part 8c for interchangeably mounting such a still camera 9.

If the still camera 9 or the imaging device 10 is for taking digital images, the image data may be sent to and be saved in an image storing device such as a computer, etc. connected to the fundus camera 1000.

Furthermore, on the examiner's side of the main body part 8, a touch panel monitor 11 is installed. On this touch panel monitor 11, fundus images of the eye to be examined E created based on the picture signals output from the still camera 9 (a digital method thereof) or the imaging device 10 are displayed. Moreover, on the touch panel monitor 11, the xy coordinate system with the center of the screen as the origin is displayed overlapped with a fundus image, and once the screen is touched, the coordinate value corresponding to the touched position is displayed.

Next, referring to FIG. 43, a composition of an optical system of the fundus camera 1000 is described. The fundus camera 1000 is provided with an illuminating optical system 100 to light the fundus oculi Ef of an eye to be examined E, a photographing optical system 120 to guide the fundus reflection light of the illumination light to the eyepiece part 8b, a still camera 9, and an imaging device 10.

The illuminating optical system 100 comprises: a halogen lamp 101, a capacitor lens 102, a xenon lamp 103, a capacitor lens 104, an exciter filter 105 and 106, a ring transparent plate 107, a mirror 108, a liquid crystal display 109, an illumination diaphragm 110, a relay lens 111, an aperture mirror 112, and an objective lens 113.

The halogen lamp 101 is an observation light source to emit fixed light. The capacitor lens 102 is an optical element to converge the fixed light (observation illumination light) emitted by the halogen lamp 101 and evenly irradiate the eye to be examined E (fundus oculi Ef) with the observation illumination light.

The xenon lamp 103 is a photographing light source to be flushed when photographing fundus oculi Ef images. The capacitor lens 104 is an optical element to converge the flush light (photographing illumination light) emitted by the xenon lamp 103 and irradiate the fundus oculi Ef evenly with the photographing illumination light.

The exciter filters 105 and 106 are the filters to be used when fluorography of ocular fundus images of a fundus oculi Ef takes a place. The exciter filters 105 and 106 respectively are to be removable on the optical path by a drive mechanism such as a solenoid, etc. The exciter filter 105 is disposed on the optical path in the event of FAG (fluorescein angiography). Whereas, the exciter filter 106 is disposed on the optical path in the event of ICG (indocyanine green angiography). Furthermore, when color images are being photographed, both exciter filters 105 and 106 are retracted from the optical path.

The ring transparent plate 107 is disposed in a conjugating location with a pupil of the eye to be examined E, and is equipped with a ring transparent part 107a taking an optical axis of the illuminating optical system 100 as a center. The mirror 108 reflects the illumination light emitted by the halogen lamp 101 or by the xenon lamp 103 in the direction of the optical axis of the photographing optical system 120. The liquid crystal display 109 displays a fixation target (not illustrated) for fixing the eye to be examined E.

The illumination diaphragm 110 is a diaphragm member to cut a part of the illumination light for flare prevention, etc. This illumination diaphragm 110 is composed movably in the light axial direction of the illuminating optical system 100, and is thus capable of changing the illuminating region of the fundus oculi Ef.

The aperture mirror 112 is an optical element to combine an optical axis of the illuminating optical system 100 and an optical axis of the photographing optical system 120. In the center region of the aperture mirror 112 an aperture part 112a is opened. The light axis of the illuminating optical system 100 and the light axis of the photographing optical system 120 are to be crossed at a substantially central location of this aperture part 112a. The objective lens 113 is installed in the objective lens part 8a of the main body part 8.

The illuminating optical system 100 having such a composition illuminates a fundus oculi Ef in the following manner. First, the observation illumination light is output when the halogen lamp 101 is lit during fundus observation. This observation illumination light irradiates the ring transparent plate 107 through the capacitor lenses 102 and 104. The light passed through the ring transparent part 107a of the ring transparent plate 107 is reflected by the mirror 108 and is reflected along the optical axial direction of the photographing optical system 120 due to the aperture mirror 108 through the liquid crystal display 109, the illumination diaphragm 110 and the relay lens 111, then is converged by the objective lens 113, to be made incident onto the eye to be examined E, and illuminates the fundus oculi Ef.

Then, the ring transparent plate 107 is disposed in a conjugating location with the pupil of the eye to be examined E, and on the pupil a ring shaped image of the entering observation illumination light is formed. The fundus reflection light of the entered observation illumination light is to be emitted from the eye to be examined E through a central dark part of the ring image on the pupil.

On the other hand, when photographing the fundus oculi Ef, flush light is emitted from the xenon lamp 103 and the photographing illumination light is irradiated onto the fundus oculi Ef through the same path. In the event of photofluorographing, either the exciter filter 105 or the exciter filter 106 is disposed selectively on the optical path depending on whether FAG photographing or ICG photographing is required.

Whereas, photographing optical system 120 comprises: an objective lens 113, an aperture mirror 112 (an aperture part 112a thereof), a photographing diaphragm 121, a barrier filter 122 and 123, a variable magnifying lens 124, a relay lens 125, a photographing lens 126, a quick return mirror 127 and a photographing media 9a. Furthermore, the photographing media 9a is a photographing media (CCD, camera film, instant film, etc.) of a still camera 9.

The fundus reflection light of the illumination light emitted through the central dart part of the ring shaped image center formed on the pupil of the eye to be examined E, enters the photographing diaphragm 121 through the aperture part 112a of the aperture mirror 112. The aperture mirror 112 reflects cornea reflection light of the illumination light and acts so as not to mix the cornea reflection light into the fundus reflection light made incident onto the photographing diaphragm 121. As a result, the generation of flare on the observation images or photographic images is prevented.

The photographing diaphragm 121 is a plate shaped member at which a plurality of circular light transparent parts of different sizes are formed. A plurality of the light transparent parts constitutes different diaphragms with different diaphragm values (F value), and are to be disposed alternatively on the optical path by a drive mechanism not illustrated herein.

The barrier filters 122 and 123 are to be removable on the optical path by a drive mechanism such as a solenoid, etc. In the event of FAG photographing, the barrier filter 122 is disposed on the optical path while in the event of ICG photographing the barrier filter 123 is inserted onto the optical path. Furthermore, when taking color images the barrier filters 122 and 123 are to be retracted from the optical path.

The variable magnifying lens 124 is to be movable in the light axial direction of the photographing optical system 120 by a drive mechanism not illustrated herein. This makes it possible to change the magnifying ratio of an observation and the magnifying ratio in photographing, and to focus images of a fundus oculi. The photographing lens 126 is a lens to form an image of the fundus reflection light from an eye to be examined E on the photographing media 9a.

The quick return mirror 127 is disposed rotatably around a rotary shaft 127a by a drive mechanism not illustrated herein. In the event of photographing a fundus oculi Ef with the still camera 9, the fundus reflection light is supposed to be guided to the photographing media 9a by springing up the quick return mirror 127 that is obliquely mounted on the optical path. Whereas, in the event of photographing a fundus oculi with an imaging device 10 or of observing the fundus oculi with the naked eye of the examiner, the quick return mirror 127 is to be obliquely mounted on the optical path to upwardly reflect the fundus reflection light.

The photographing optical system 120 is further provided with a field lens (eye vision lens) 128 for guiding the fundus reflection light reflected by the quick return mirror 127, a switching mirror 129, an eyepiece 130, a relay lens 131, a reflection mirror 132, a photographing lens 133 and an image pick up element 10a. The image pick up element 10a is an image pick up element such as CCD, etc. installed internally in the imaging device 10. On the touch panel monitor 11 a fundus oculi image Ef' photographed by the image pick up element 10a is be displayed.

The switching mirror 129 is to be rotatable around the rotary shaft 129a as well as the quick return mirror 127. This switching mirror 129 is obliquely disposed on the optical path during observation with the naked eye and guides reflected light on the fundus oculi to the eyepiece 130.

Furthermore, when a fundus image is photographed by the imaging device 10, the switching mirror 129 is retracted from the optical path. The fundus reflection light forms an image on the image pick up element 10a through the relay lens 131, the mirror 132, the photographing lens 133 and then the fundus image Ef' is be displayed on the touch panel monitor 11.

Such a fundus camera 1000 is a fundus observation apparatus to be used for observing the state of the surface of a fundus oculi Ef, that is, the retina. Whereas, in the deep layer of retina tissues such as where the choroidea or sclera are found, in recent years, devices for observing these deep layer tissues have been practically implemented (e.g. ref JP Patent laid-open No. 2003-000543 and JP Patent Application No. 2004-52195)

The fundus observation apparatus disclosed in JP Patent laid-open No. 2003-000543 and JP Patent Application No. 2004-52195 are devices to which so called OCT (Optical Coherence Tomography) technology is applied. With such fundus observation devices, low coherence light is split into two, one of which (signal light) is guided to a fundus oculi and the other one (reference light) is guided to a given reference object, while at the same time this is a device to form a tomographic image of the surface and the deep layer tissue of a fundus oculi, based on the interference light obtained by overlaying the signal light that has passed through the fundus oculi and the reference light that has been reflected by the reference object In order to capture the state of a fundus oculi (presence/absence of a disease or the progressing state, the degree of a therapy effect or a recovery state, etc.) in detail, it is desirable to consider both the state of fundus surface (retina) and the state of deep layer tissues (choroidea or sclera). However, by just observing an image of the fundus surface obtained from a fundus camera, it is difficult to capture the state of the deep layer tissues in detail, while, with tomographic images of the fundus oculi obtained from an optical image measuring device, it was difficult to capture the detailed state of the fundus surface or the entire retina.

Furthermore, in order to determine the state of fundus oculi comprehensively, it is considered to be desirable to determine the state of a disease by taking both the state of the retina and the state of deep layer tissues into consideration.

For that purpose, it is necessary to present a fundus image from a fundus camera and a fundus image from an optical image measuring device in a mutually comparable display manner. For example, it is desirable to make an attempt to make comparisons easier by presenting both fundus images at the same time.

Furthermore, it is desirable to be able to perform comparisons easily by adopting a display method capable of capturing the interrelationship between the fundus image from a fundus camera and the fundus image from an optical image measuring device.

Particularly, when an attention area such as a diseased part in one of the fundus images is discovered, there may be many cases in which one wishes to capture more details of the state of the attention area by referring to the state of the attention area of the other fundus images.

However, with the conventional fundus observation device, it was difficult to capture the state of the attention area in detail, as the positional relation to each other between a 2-dimensional surface image of the fundus of an eye to be examined by a fundus camera and a tomographic image of the fundus by an optical image measuring device was not easy to capture.

The present invention has been conducted in order to solve such a problematic point, and with the purpose of providing a fundus observation device, a fundus image display device, and a fundus observation program capable of easily capturing the positional relation between a plurality of fundus images, particularly the positional relation between the 2-dimensional image and the tomographic image of the surface of a fundus oculi.

SUMMARY OF THE INVENTION

In order to achieve above purpose, the first aspect of the invention is a fundus observation device that is characterized in comprising: a first image forming means for forming a 2-dimensional image of the surface of a fundus oculi of an eye to be examined; a second image forming means for forming a tomographic image of said fundus oculi, a display means, a controlling means for displaying said 2-dimensional image formed by said first image forming means and said tomographic image formed by said second image forming means in parallel on said display means, while at the same time, for displaying the cross-sectional position information indicating the cross-sectional position of said tomographic image on the surface of said fundus oculi, so as to be overlapped with said 2-dimensional image.

Furthermore, the second aspect of the invention is a fundus image display device that is characterized in being connected to a first image forming means for forming a 2-dimensional image of the surface of the fundus oculi of an eye to be examined and to a second image forming means, comprising a display means and a controlling means for displaying said 2-dimensional image formed by said first image forming means and said tomographic image formed by said second image forming means in parallel on said display means, while at the same time, for displaying the cross-sectional position information indicating the cross-sectional position of said tomographic image at the surface of said fundus oculi, so as to be overlapped with said 2-dimensional image.

Furthermore, the third aspect of the invention is a fundus observation program that is characterized in making a computer, which is connected to a first image forming means for forming a 2-dimensional image of the surface of a fundus oculi of an eye to be examined and to a second image forming means for forming a tomographic image of said fundus oculi, and which is equipped with a display means, function as a controlling means for displaying said 2-dimensional image formed by said first image forming means and said tomographic image formed by said second image forming means in parallel on said display means, while at the same time displaying the cross-sectional position information indicating the cross-sectional position of said tomographic image on the surface of said fundus oculi, so as to be overlapped with said 2-dimensional image.

EFFECTS OF THE INVENTION

According to the present invention, as it is configured in a manner such that the 2-dimensional image formed by a first image forming means and the tomographic image formed by a second image forming means are to be displayed in parallel, and at the same time, the cross-sectional position information indicating the cross-sectional position of the tomographic image of the surface of a fundus oculi is displayed so as to be overlapped with the 2-dimensional image, the examiner can easily capture the position of the tomographic image on the 2-dimensional image at a glance, and therefore, the positional relation of the 2-dimensional image and the tomographic image to each other may easily be captured.

BRIEF DESCRIPTION OF THE DRAWINGS

In the accompanying drawings:

FIG. 6 is a schematic diagram representing one example of scanning features of signal light in a favorable embodiment of the fundus observation device related to the present invention.

DETAILED DESCRIPTION OF THE REFERENCE EMBODIMENTS

Figure 42:
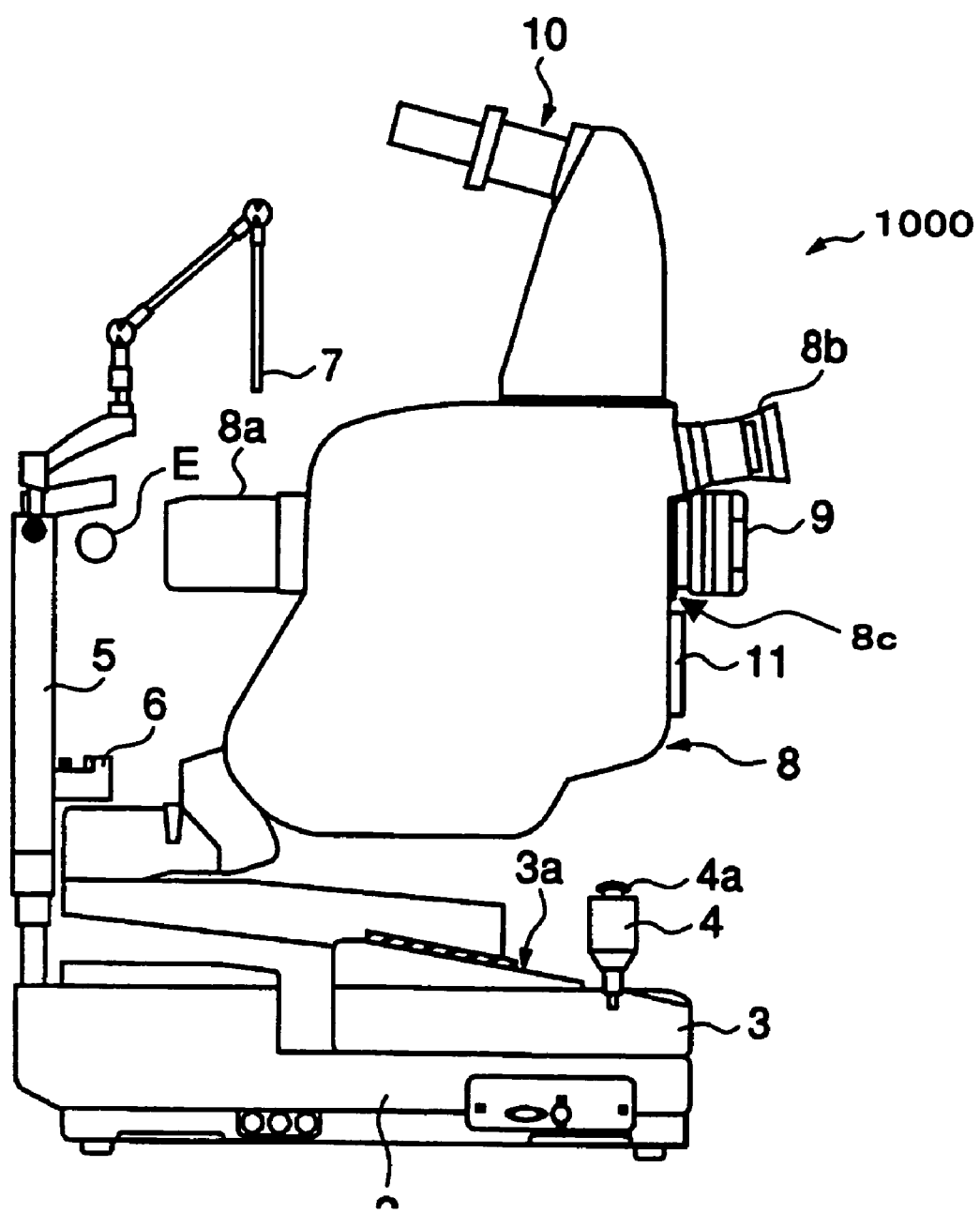
FIG. 42 is a schematic side view representing an appearance constitution of a conventional fundus observation device (fundus camera).
Figure 43:
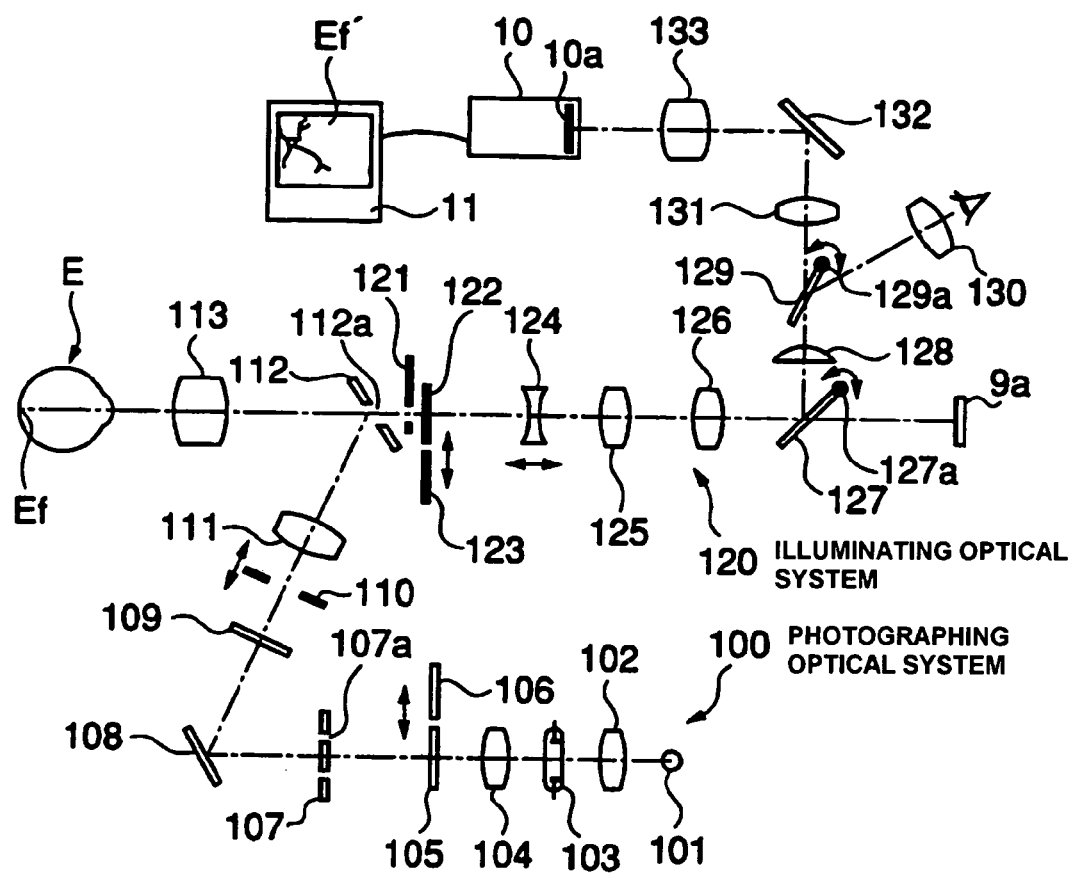
FIG. 43 is a schematic diagram representing one example of an internal constitution (an optical system constitution) of a conventional fundus observation device (fundus camera).

One example of favorable embodiments of a fundus observation device, a fundus image display device and a fundus observation program, related to the present invention is described in detail referring to figures. Furthermore, for compositional parts that are the same as conventional ones, the same numeric symbols used in FIG. 42 and FIG. 43 are used.

Embodiment 1

Figure 1:
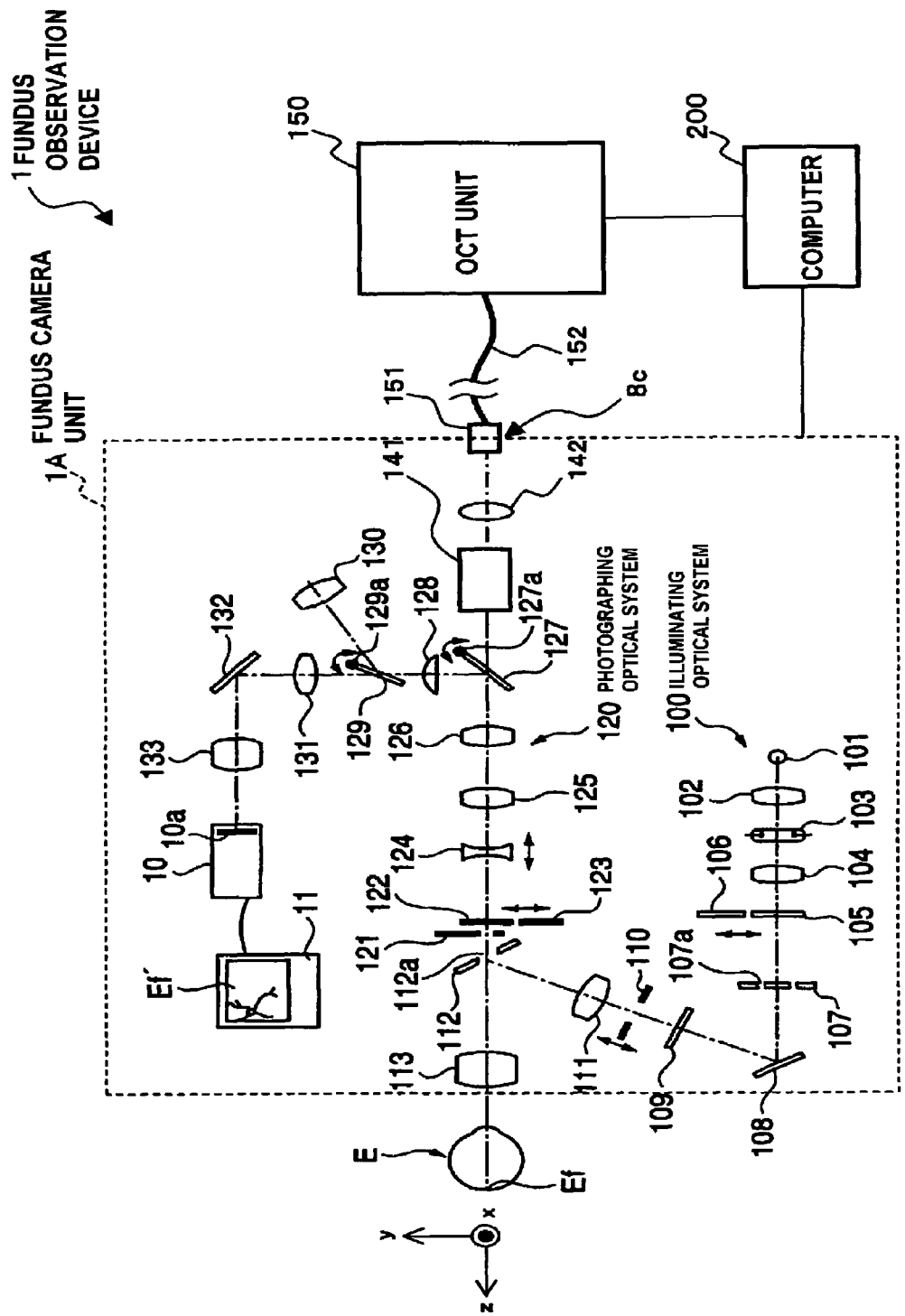
FIG. 1 is a schematic diagram representing one example of the entire constitution in a favorable embodiment of the fundus observation device related to the present invention.
Figure 2:
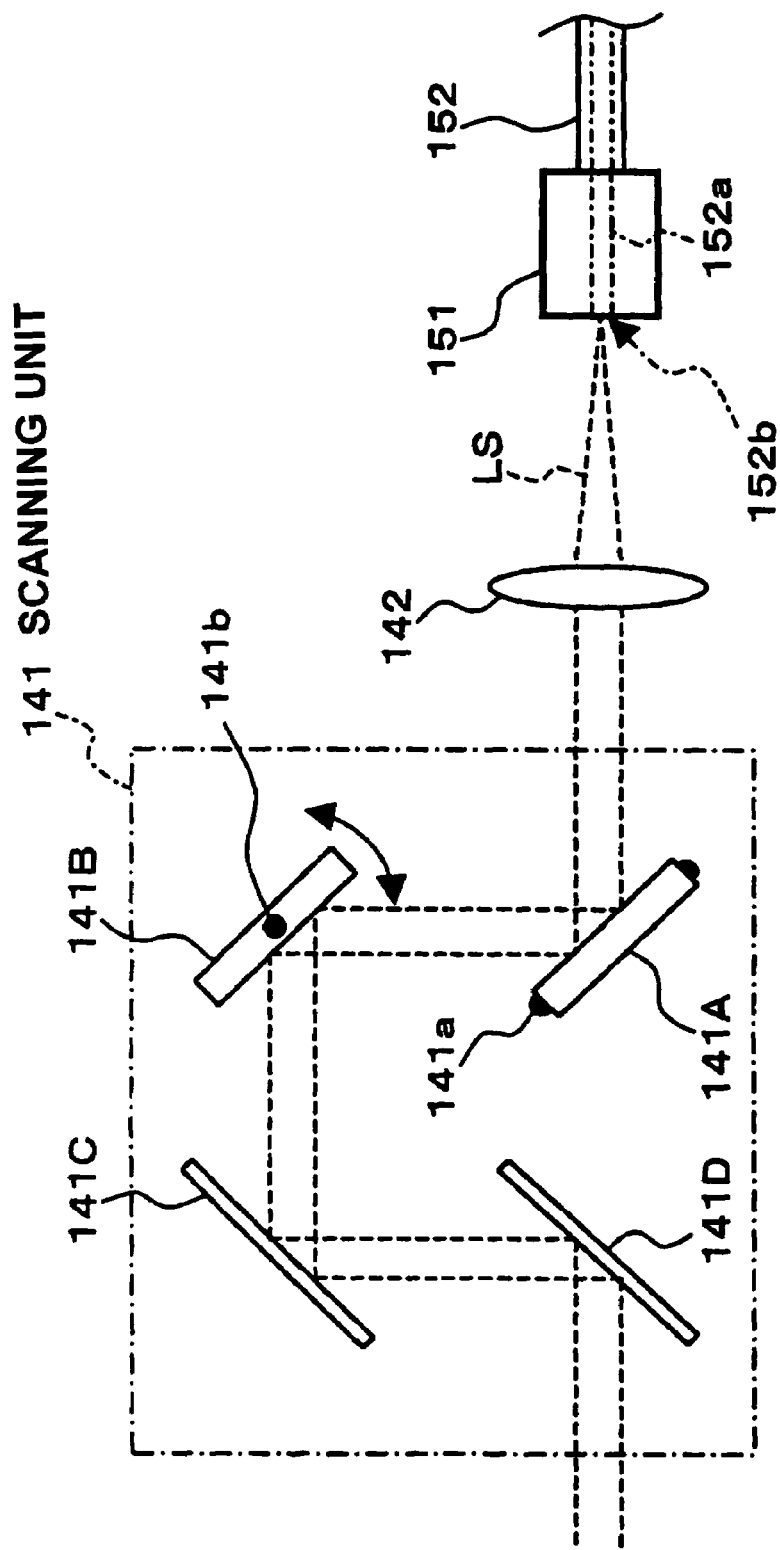
FIG. 2 is a schematic diagram representing one compositional example of a scanning unit installed in a fundus camera unit in a favorable embodiment of the fundus observation device related to the present invention.
Figure 3:
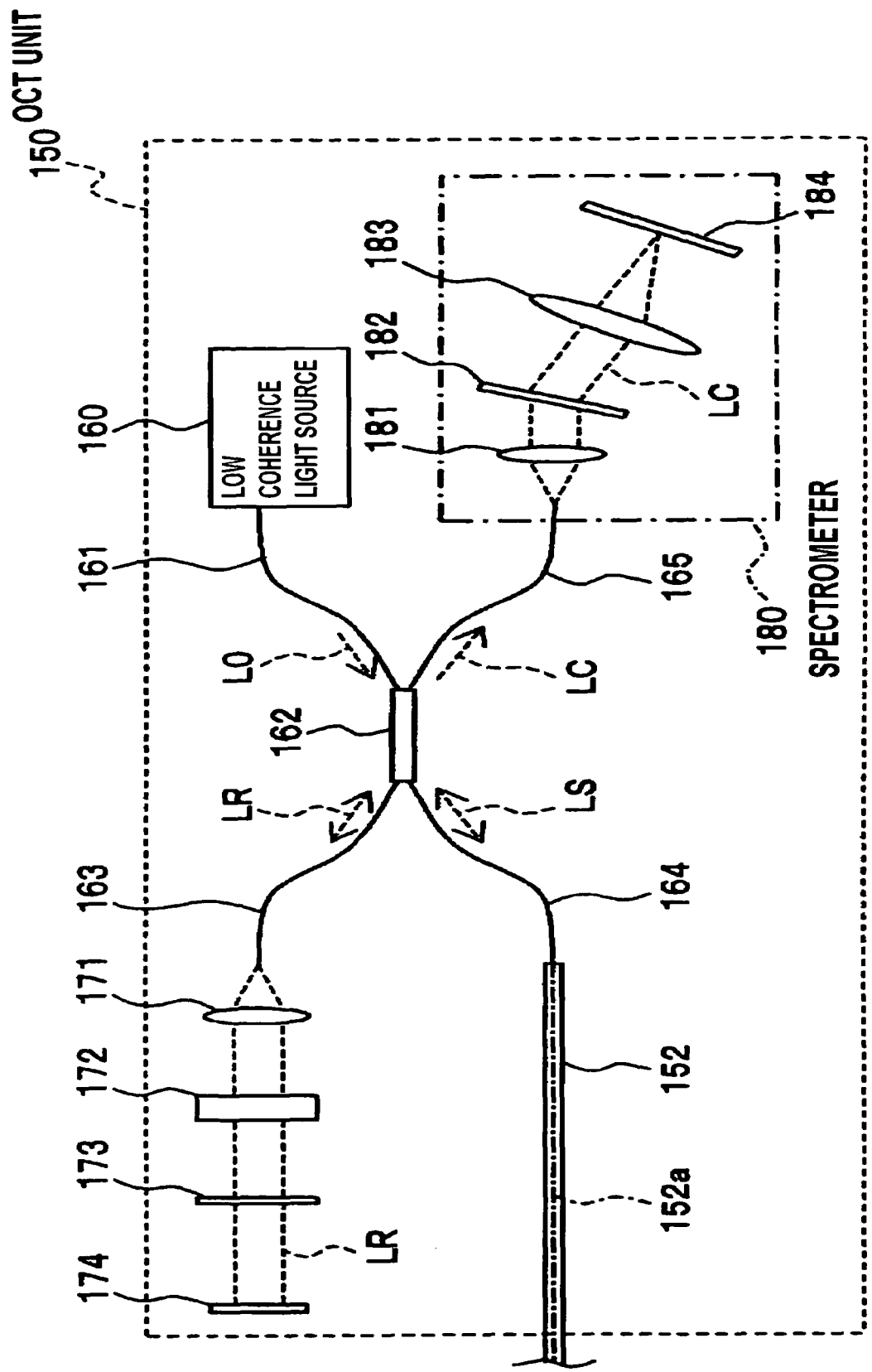
FIG. 3 is a schematic diagram representing one compositional example of an OCT unit in a favorable embodiment of the fundus observation device related to the present invention.
Figure 4:
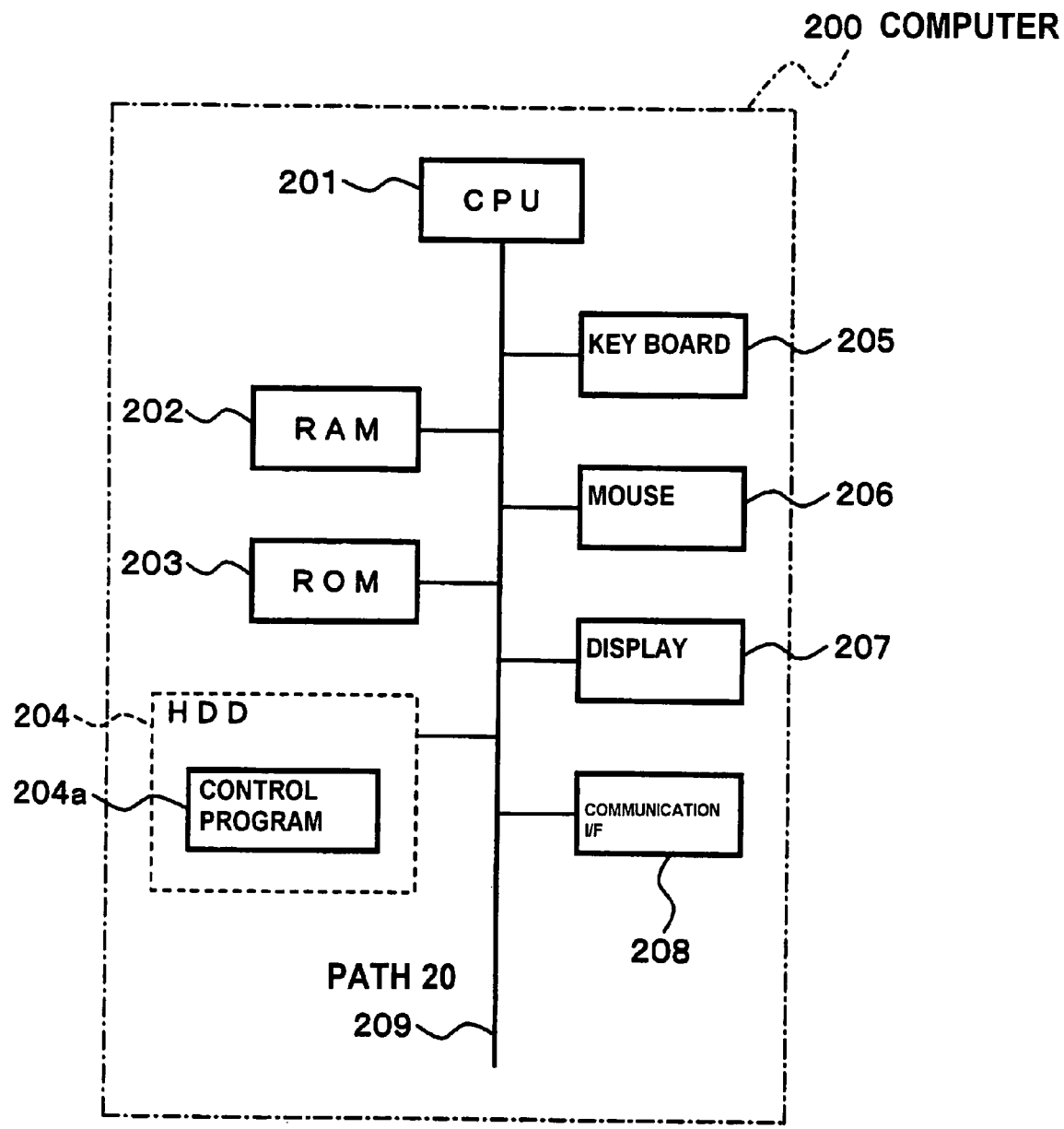
FIG. 4 is a schematic block diagram representing one example of hardware configurations of a computer in a favorable embodiment of the fundus observation device related to the present invention.
Figure 5:
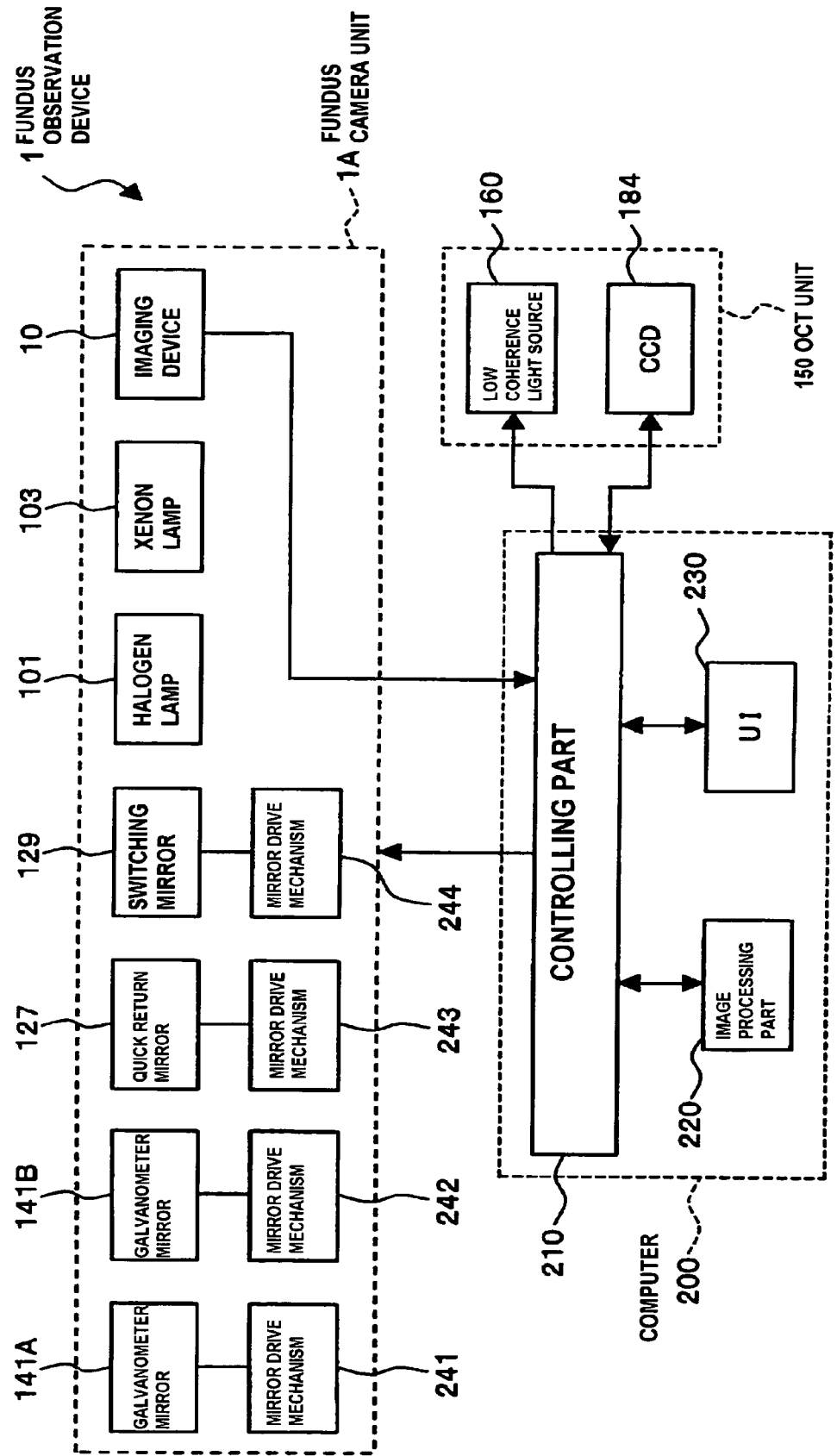
FIG. 5 is a schematic block diagram representing one compositional example of a control system in a favorable embodiment of the fundus observation device related to the present invention.

First, by referring to FIGS. 1 through 5, the composition of Embodiment 1 of the fundus observation device related to the present invention is described. FIG. 1 shows the entire constitution of the fundus observation device 1 related to the present invention. FIG. 2 shows a composition of a scanning unit 141 in a fundus camera unit 1A. FIG. 3 shows a composition of an OCT unit 150. FIG. 4 shows a hardware configuration of a computer 200. FIG. 5 shows a configuration of a control system of the fundus observation unit 1.

[The Entire Constitution]

As shown in FIG. 1, the fundus observation device 1 is comprised of a fundus camera unit 1A that functions as a fundus camera, an OCT unit 150 accommodating the optical system of an optical image measuring device (OCT device), and a computer 200 that executes various control processes, etc.

This fundus camera unit 1A constitutes the "first image forming means" and "fundus camera" of the present invention. Furthermore, the OCT unit 150 and the computer 200 (image processing part 220 thereof) constitute one example of the "second image forming means" and "optical measuring device" of the present invention. Moreover, the "second image forming means" and "optical measuring device" include a scanning unit 141 installed in the fundus camera unit 1A. In addition, the computer 200 is an equivalent of one example of the "fundus image display device" of the present invention.

To the OCT unit 150, one end of a connection line 152 is attached. To the other end of this connection line 152, a connector part 151 is attached. This connector part 151 is attached to a mounting part 8c shown in FIG. 42. Furthermore, a conductive optical fiber runs through the inside of the connection line 152. The OCT unit 150 and the fundus camera unit 1A are optically connected through the connection line 152. The composition details of the OCT unit 150 are to be described later referring to FIG. 3.

(Constitution of Fundus Camera Unit)

The fundus camera unit 1A has substantially the same appearance as the conventional fundus camera 1000 shown in FIG. 42. Furthermore, as in the conventional optical system shown in FIG. 43, the fundus camera unit 1A is provided with an illuminating optical system 100 to light a fundus oculi Ef of an eye to be examined E, and a photographing optical system 120 for guiding the fundus reflection light of the illumination light to an eyepiece 8b, an imaging device 10, and an OCT unit 150.

Also, the illuminating optical system 100 is comprised as in conventional ones including: a halogen lamp 101, a capacitor lens 102, a xenon lamp 103, a capacitor lens 104, an exciter filter 105 and 106, a ring transparent plate 107, a mirror 108, a liquid crystal display 109, an illumination diaphragm 110, a relay lens 111, an aperture mirror 112, and an objective lens 113.

While, as in conventional ones, the photographing optical system 120 comprises: an objective lens 113, an aperture mirror 112 (aperture part 112a thereof), a photographing diaphragm 121, a barrier filter 122 and 123, a variable magnifying lens 124, a relay lens 125, a photographing lens 126, a quick return mirror 127, a field lens (eye vision lens) 128, a switching mirror 129, an eyepiece 130, a relay lens 131, a reflection mirror 132, a photographing lens 133 and an image pick up element 10a.

The image pick up element 10a is an image pick up element such as CCD, etc. installed internally in the imaging device 10 such as a TV camera. A 2-dimensional image (fundus oculi image Ef') of the surface of a fundus oculi Ef photographed by the imaging device 10 is displayed on display devices such as on the touch panel monitor 11, or on a display (to be described later) of the computer 200.

Furthermore, the photographing optical system 120 of the present embodiment is provided with a scanning unit 141 and a lens 142. The scanning unit 141 is equipped with a constitution to scan the light output (signal light LS; to be described later) from the OCT unit 150 on a fundus oculi Ef.

The lens 142 incidents the signal light LS from the OCT unit 150 in the form of parallel light flux onto the scanning unit 141. Furthermore, the lens 142 acts so as to converge the fundus reflection light of the signal light LS that has reached through the scanning unit 141.

In FIG. 2, one example of a concrete composition of the scanning unit is shown. The scanning unit 141 is comprised including Galvanometer mirrors 141A, 141B, and reflection mirrors 141C, 141D.

The Galvanometer mirrors 141A and 141B are to be rotatable centering around rotary shafts 141a and 141b respectively. The rotary shaft 141a and 141b are arranged perpendicular to each other. In FIG. 2, the rotary shaft 141a of the Galvanometer mirror 141A is arranged parallel to the paper face on the same figure, while the rotary shaft 141b of the Galvanometer mirror 141B is arranged perpendicular to the paper face in the same figure. That is, the Galvanometer mirror 141B is to be rotatable in the directions indicated by an arrow pointing in both directions in FIG. 2, while the Galvanometer mirror 141A is to be rotatable in the directions perpendicular to the arrow pointing in both directions. As a result, this pair of Galvanometer mirrors 141A and 141B act so that the reflecting direction of the signal light LS changes to a direction perpendicular to each other. Furthermore, the rotary movement of the Galvanometer mirror 141A and 141B respectively is driven by a drive mechanism to be described later.

The signal light LS reflected by the Galvanometer mirrors 141A and 141B is to be reflected by reflection mirrors 141C and 141D, and is to advance in the same direction as having entered into the Galvanometer mirror 141A.

As described previously, a conductive optical fiber 152a runs inside the connection line 152, and the end face 152b of the optical fiber 152a is arranged opposing the lens 142. The signal light LS emitted from this end face 152b advances while gradually expanding its beam diameter toward the lens 142 until being converged to a parallel light flux by this lens 142. On the contrary, the fundus reflection light of the signal light LS is converged toward the end face 152b by this lens 142.

(Constitution of OCT Unit)

Next, referring to FIG. 3, the constitution of an OCT unit 150 is described. The OCT unit 150 shown in the same figure has substantially the same optical system as a conventional optical image measuring device, and is equipped with an interferometer that splits the light output from a light source into reference light and signal light, and generates interference light by the reference light that has passed through a reference object and the signal light that has passed through an object to be measured (fundus oculi Ef), and at the same time, is configured to form images of the object to be measured by analyzing the detection result of this interference light.

A low coherence light source 160 is composed of a broad band light source such as super luminescent diode (SLD) that outputs low coherence light L0 or a light emitting diode (LED), etc. This low coherence light L0, for instance, has a wave length in the near-infrared region and is supposed to be light having a time wise coherence length of approximately several tens of micro-meters.

The low coherence light L0 output from the low coherence light source 160 is guided to an optical (coupler) 162 through an optical fiber 161 composed of, e.g. a single mode fiber, and then split into reference light LR and signal light LS.

Furthermore, the optical coupler 162 has both actions, i.e. a means for splitting the light (splitter), and a means for overlaying the light (coupler); however, herein conventionally referred to as an "optical coupler".

The reference light LR is guided by an optical fiber 163 and emitted from the end face of the fiber. The emitted reference light LR is reflected by a reference mirror 174 (reference object) through a glass block 172 and a density filter 173 after having been converged into a parallel light flux by a collimator lens 171.

The reference light LR reflected by the reference mirror 174 is converged to the end face of the fiber of the optical fiber 163 by the collimator lens 171 again through the density filter 173 and the glass block 172. The converged reference light LR is guided to the optical coupler 162 through the optical fiber 163.

Furthermore, the glass block 172 and the density filter 173 act as a delaying means to match the optical path length (optical distance) between the reference light LR and the signal light LS, and as a means to match the dispersion characteristics of reference light LR and the signal light LS.

Whereas, the signal light LS is guided to the end part of the connection line 152 by an optical fiber 164. A conductive optical fiber 152a runs inside the connection line 152. Herein, the optical fiber 164 and the optical fiber 152a may be composed of a single optical fiber, or may be jointly formed by connecting each end. In either case, it is sufficient as long as the optical fiber 164 and 152a are composed so as to be capable of transferring the signal light LS between the fundus camera unit 1A and the OCT unit 150.

The signal light LS is guided within the connection line 152 to the fundus camera unit 1A. Then, the signal light LS enters into the eye to be examined E through the lens 142, the scanning unit 141, the photographing lens 126, the relay lens 125, the variable magnifying lens 124, the photographing diaphragm 121, the aperture part 112a of an aperture mirror 112, and the objective lens 113 (then, as described later, the barrier filter 122 and 123 as well as the quick return mirror 127 are retracted from the optical path respectively).

The signal light LS that has entered into the eye to be examined E forms an image on a fundus oculi (retina) Ef and is then reflected. Then, the signal light LS is not only reflected on the surface of the fundus oculi Ef, but is also scattered at the refractive index boundary reaching the deep area region of the fundus oculi Ef. As a result, the fundus reflection light of the signal light LS becomes a light containing the information reflecting the surface state of the fundus oculi Ef and the information reflecting the scattered state in the rear at the refractive index boundary of the deep area tissue. The light is simply referred as "fundus reflection light (signal light LS thereof).

The fundus reflection light of the signal light LS advances reversely on the above route and converges at the end face 152b of the optical fiber 152a, then enters into the OCT unit 150 through this optical fiber 152, and returns to the optical coupler 162 through the optical fiber 164. The optical coupler 162 overlays this signal light LS and the reference light LR reflected at the reference mirror 174 to generate interference light LC. The generated interference light LC is guided into a spectrometer 180 through an optical fiber 165.

Herein, the "interference light generating means" in the present invention is comprised of an interferometer including at least an optical coupler 162, an optical fiber 163 and 164, and a reference mirror 174. Furthermore, although a Michelson type interferometer has been adopted in the present embodiment, for instance, a Mach Zender type, etc. or any optional type of interferometer may be adopted appropriately.

The spectrometer 180 is comprised of a collimator lens 181, a diffraction grating 182, an image forming lens 183, and a CCD (Charge Coupled Device) 184. The diffraction grating 182 in the present embodiment is a transmission type diffraction grating; however, needless to say, a reflection type diffraction grating may also be used. Furthermore, needless to say, in place of CCD 184, it is also possible to adopt other photo-detecting elements (detecting means).

The interference light LC made incident onto the spectrometer 180 is to be split (spectral resolution) by the diffraction grating 182 after having been converged into a parallel light flux by the collimator lens. The split interference light LC forms an image on the image pick up surface of the CCD 184 by the image forming lens 183. The CCD 184 receives this interference light LC that is to be converted to an electrical detection signal, and outputs this detection signal to the computer 200.

(Computer Configuration)

Next, the configuration of the computer 200 is described referring to FIG. 4. This computer 200 analyzes the detection signal input from the CCD 184 and performs a process of forming tomographic images of a fundus oculi Ef of an eye to be examined E. The analysis technique then is the same technique as the conventional Fourier domain OCT technique. Furthermore, the computer 200 executes the control of each part of the fundus camera unit 1A and the control of each part of the OCT unit 150.

As for the control of the fundus camera unit 1A, to be controlled is, for example: controlling the output of illumination light by the halogen lamp 101 or the xenon lamp 103; controlling the insertion/retraction operation of the exciter filters 105, 106, or the barrier filters 122, 123 on the optical path; controlling the display operation of the liquid crystal display 109; controlling the shift of the illumination diaphragm 110 (controlling the diaphragm value); controlling the diaphragm value of the photographing diaphragm 121; controlling the shift of the variable magnifying lens 124 (controlling the magnification); and controlling the insertion/retraction operation of the quick return mirror 127 or the switching mirror 129 on the optical path (switching the optical path), etc. Furthermore, the computer performs a control of rotary operations of the Galvanometer mirrors 141A, 141B within the scanning unit 141.

Whereas, as for the control of the OCT unit 150, output control of the low coherence light by a low coherence light source 160, or control of accumulated time of the CCD 184, etc. are to be performed.

The hardware configuration of the computer 200 that acts as described above is explained referring to FIG. 4. The computer 200 is provided with a hardware configuration that is the same as conventional computers. To be specific, the configuration includes: a CPU201 (a type of microprocessor), a RAM202, a ROM203, a hard disk drive (HDD) 204, a key board 205, a mouse 206, a display 207 and a communication interface (I/F) 208. Each part of these is connected through a bus 209.

The CPU 201 executes operations characteristic to the present invention by rolling out a control program 204a that has been stored in the hard disk drive 204, on the RAM 202. This control program 204a is the equivalent of one example of "fundus observation program" in the present invention.

Furthermore, the CPU201 executes control of each part of the devices that have previously been described or various arithmetic processes, etc. Moreover, control of each part of the devices that respond to an operation signal from the key board 205 or the mouse 206, control of display processes by the display 207, and control of transmitting/receiving processes of various types of data or control signals, etc. by the communication interface 208.

The key board 205, the mouse 206 and the display 207 are used as a user interface of the fundus observation device 1. The key board 205 is used as a device for entering letters or figures, etc. by typing. The mouse 206 is used as a device to perform various entry operations with respect to the display screen of the display 207.

Furthermore, the display 207 being an optional display device such as LCD (Liquid Crystal Display) or CRT (Cathode Ray Tube), etc. displays images of a fundus oculi Ef formed by the fundus observation device 1 and displays various operation screens or set up screens, etc.

Furthermore, the user interface of the fundus observation device 1 is not limited to such a configuration but may be configured by using an optional user interface means equipped with a function to display and output various information such as track ball, joystick, touch panel type LCD, control panel for ophthalmology examinations, and with a function to input various information.

The communication interface 208 performs the process of sending control signals from the CPU 201 to each part of the fundus camera unit 1A or of the OCT unit 150, or the process of receiving detection signals output from the CCD 184.

Moreover, when the computer 200 is connected to a network such as LAN (Local Area Network) or Internet, etc., the communication interface 208 may be configured to be equipped with a network adopter such as LAN card, etc. or a communication equipment such as modem, etc. so as to be able to perform data communication through the network. In this case, a server accommodating the control program 204a may be installed, and at the same time, the computer 200 may be configured as a client terminal of the server.

[Control System Configuration]

The configuration of the control system of the fundus observation device 1 having the configuration described above is explained referring to FIG. 5. FIG. 5 shows a part related to the operations or processes of the present invention that has been particularly selected from among constituents composing the fundus observation device 1.

The control system of the fundus observation device 1 is configured having a controlling part 210 of the computer 200 in the center. The controlling part 210 is an equivalent of one example of a "controlling means" of the present invention and is comprised including: a CPU201, a RAM202, a ROM203, a hard disk drive 204 (control program 204a), and a communication interface 208.

The controlling part 210 executes said controlling processes by the CPU201 that is operated based on the control program 204a. Particularly, by controlling the mirror drive mechanisms 241, 242, 243, 244 of the fundus camera unit 1A respectively, the Galvanometer mirrors 141A, 141B, the quick return mirror 127, and the switching mirror 129 respectively may be operated independently.

Furthermore, although the details are to be described later, the controlling part 210 executes control for displaying two kinds of images photographed by the fundus observation device 1: that is, a 2-dimensional image (fundus image Ef') of the surface of a fundus oculi Ef by the fundus camera unit 1A, and an image of a fundus oculi Ef formed based on the detection signal obtained by the OCT unit 150, parallel to each other on the display 207 of the user interface 230.

The user interface (UI) 230 is equipped with operational devices such as a key board 205 or a mouse 206, etc. and with a display device such as a display 207, etc. This user interface 230 constitutes one example of the "operating means" and "display means" of the present invention.

The controlling feature of scanning signal light LS by the controlling part 210 and the image forming process feature by the image processing part 220 are respectively described below.

(Regarding the Signal Light Scanning)

Scanning of signal light LS is performed by changing the facing direction of the reflecting surfaces of the Galvanometer mirrors 141A and 141B of the scanning unit 141 in the fundus camera unit 1A. By controlling the mirror drive mechanisms 241 and 242 respectively, the controlling part 210 changes the facing direction of the reflecting surfaces of the Galvanometer mirror 141A and 141B, and scans the signal light LS on the fundus oculi Ef.

Once the facing direction of the reflecting surface of the Galvanometer mirror 141A is changed, the signal light LS is scanned in a horizontal direction (x-direction in FIG. 1) on the fundus oculi Ef. Whereas, once the facing direction of the reflecting surface of the Galvanometer mirror 141A is changed, the signal light LS is scanned in a vertical direction (y-direction in FIG. 1) on the fundus oculi Ef. Furthermore, by changing the facing direction of the reflecting surfaces of both Galvanometer mirrors 141A and 141B simultaneously, the signal light LS may be scanned in the combined x-direction and y-direction. That is, by controlling these two Galvanometer mirrors 141A and 141B, the signal light LS may be scanned in an arbitrarily direction on the xy plane.

Figure 6A:
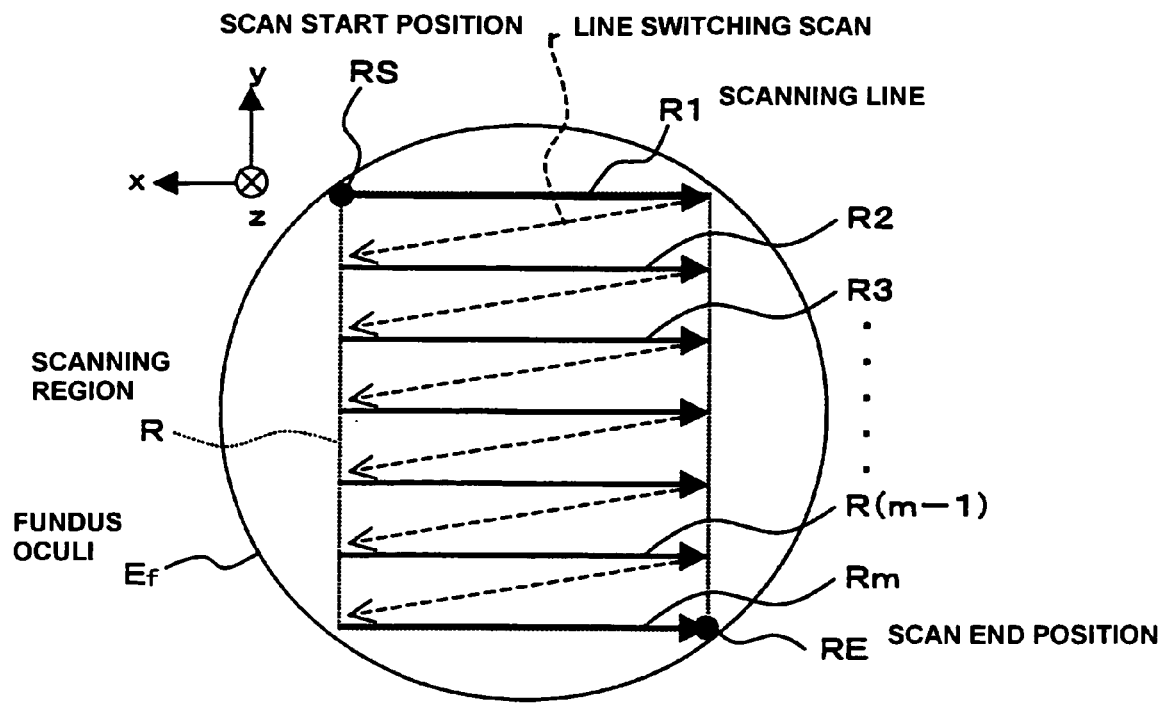
FIG. 6A represents one example of the scanning features of signal light when a fundus oculi is seen from the incident side of the signal light with respect to an eye to be examined. In addition.
Figure 6B:
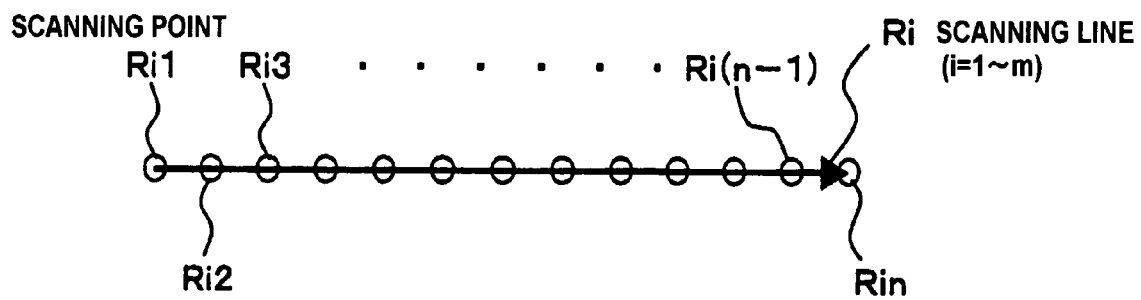
FIG. 6B represents one example of arrangement features of scanning points of each scanning line.

FIG. 6 represents one example of scanning features of signal light LS for forming images of a fundus oculi Ef. FIG. 6 (A) represents one example of scanning features of the signal light LS, when the signal light LS sees the fundus oculi Ef from an incident direction onto the eye to be examined E (that is, +direction of z is seen from −direction of z in FIG. 1). Furthermore, FIG. 6 (B) represents one example of arrangement features of scanning points on each scanning line on the fundus oculi Ef.

As shown in FIG. 6 (A), the signal light LS is scanned within a rectangular shaped scanning region R that has been preset. Within this scanning region R, a plurality of (m number of) scanning lines R1 through Rm have been set in the x-direction. When the signal light LS is scanned along each scanning line Ri (i=1 through m), detection signals of interference light LC are to be generated.

Herein, the direction of each scanning line Ri is referred as the "main scanning direction" and the orthogonally crossing direction is referred as the "sub-scanning direction". Therefore, the scanning of the signal light LS in a main scanning direction is performed by changing the facing direction of the reflecting surface of the Galvanometer mirror 141A, and the scanning in a sub-scanning direction is performed by changing the facing direction of the reflecting surface of the Galvanometer mirror 141B.

On each scanning line Ri, as shown in FIG. 6 (B), a plurality (n number of) of scanning points Ri1 through Rin have been preset.

In order to execute the scanning shown in FIG. 6, the controlling part 210 controls the Galvanometer mirrors 141A and 141B to set the incident target of the signal light LS with respect to a fundus oculi Ef at a scan start position RS (scanning point R11) on the first scanning line R1. Subsequently, the controlling part 210 controls the low coherence light source 160 to flush the low coherence light L0 for emitting the signal light LS to the scan start position RS. The CCD 184 receives the interference light LC based on the fudus reflection light of this signal light LS at the scan start position RS, and outputs detection signals to the controlling part 210.

Next, by controlling the Galvanometer mirror 141A the controlling part 210 scans the signal light LS in a main scanning direction and sets the incident target at a scanning point R12, triggering a flush emission of the low coherence light L0 for making the signal light LS incident onto the scanning point R12. The CCD 184 receives the interference light LC based on the fundus reflection light of this signal light LS at the scanning point R12, and then outputs the detection signal to the controlling part 210.

Likewise, the controlling part 210 obtains detection signals output from the CCD 184 responding to the interference light LC with respect to each scanning point, by flush emitting the low coherence light L0 at each scanning point while shifting the incident target of the signal light LS from scanning point R13, R14, - - -, R1 (n–1), R1n in order.

Once the measurement at the last scanning point R1n of the first scanning line R1 is finished, the controlling part 210 controls the Galvanometer mirrors 141A and 141B simultaneously and shifts the incident target of the signal light LS to the first scanning point R21 of the second scanning line R2 following a line switching scan r. Then, by conducting the previously described measurement with regard to each scanning point R2j (j=1 through n) of this second scanning line R2, a detection signal corresponding to each scanning point R2j is obtained.

Likewise, by conducting a measurement with respect to the third scanning line R3, - - -, the m–1th scanning line R (m–1), the mth scanning line Rm respectively to obtain the detection signals corresponding to each scanning point. Furthermore, the symbol RE on a scanning line Rm is a scan end position in accordance with a scanning point Rmn.

As a result, the controlling part 210 obtains m×n number of detection signals corresponding to m×n number of scanning points Rij (i=1 through m, j=1 through n) within the scanning region R. Hereinafter, a detection signal corresponding to the scanning point Rij may be represented as Dij.

Such interlocking control of such shifting of scanning points and the output of the low coherence light L0 may be realized by synchronizing, for instance, the transmitting timing of control signals with respect to the mirror drive mechanisms 241, 242 and the transmitting timing of control signals (output request signal) with respect to the low coherence light source 160.

As described, when each Galvanometer mirror 141A and 141 B is being operated, the controlling part 210 stores the position of each scanning line Ri or the position of each scanning point Rij (coordinate on the xy coordinate system) as information indicating the content of the operation. This stored content (scan positional information) is used in an image forming process as was conducted conventionally.

(Regarding Image Forming Processes)

With regard to the image forming processes by an image processing part 220, one example is explained. This image processing part 220 is an equivalent of one example of "a second image processing means" in the present invention, and is comprised including a CPU 201 that is operated based on a control program 204a.

The image processing part 220 executes the formation process of tomographic images of a fundus oculi Ef along each scanning line Ri (main scanning direction), and the formation process of a 3-dimensional image of the fundus oculi Ef based on these tomographic images.

The formation process of a tomographic image along the main scanning direction is configured as was conventionally done including a 2-step arithmetic process. In the first step of the arithmetic process, based on a detection signal Dij corresponding to each scanning point Rij, an image in the depth direction (z-direction in FIG. 1) of a fundus oculi Ef at the scanning point Rij is formed.

Figure 7:
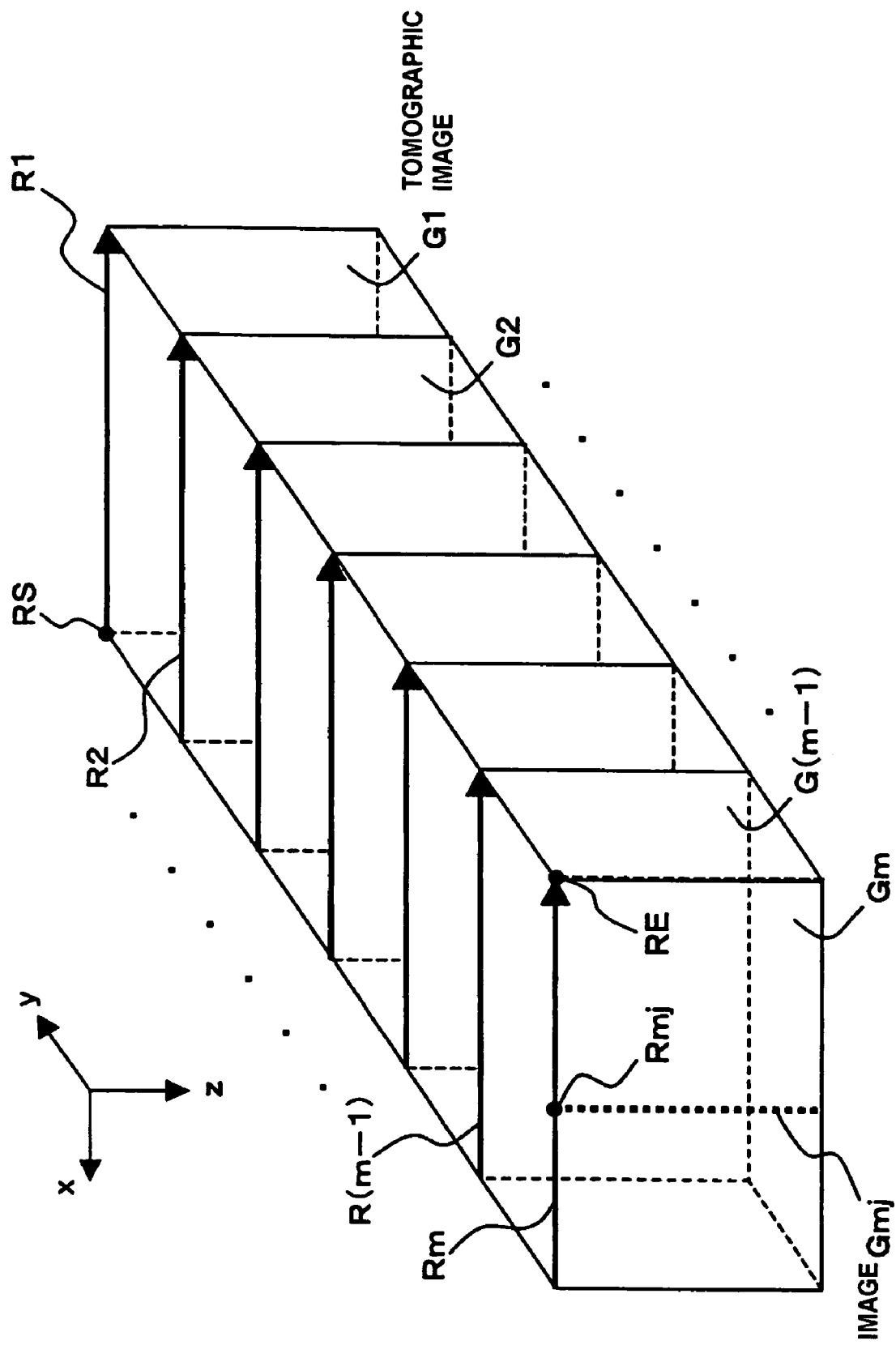
FIG. 7 is a schematic diagram representing one example of the scanning features of signal light and tomographic image features formed along each scanning line in a favorable embodiment of the fundus observation device related to the present invention.

FIG. 7 represents a feature of a tomographic image formed by the image processing part 220. In the second step of the arithmetic process, with regard to each scanning line Ri, based on the images in the depth direction at the n number of scanning points Ri1 through Rin thereon, a tomographic image Gi of a fundus oculi Ef along this scanning line Ri is formed. Then, the image processing part 220 determines the arrangement and the distance of each scanning point Ri1 through Rin while referring to the positional information (said scan positional information) of each scanning point Ri1 through Rin, and forms this scanning line Ri. Due to the above process, m number of tomographic images G1 through Gm at different positions of the sub-scanning direction (y-direction) are obtained.

Next, the formation process of a 3-dimensional image of a fundus oculi Ef is explained. A 3-dimensional image of a fundus oculi Ef is formed based on the m number of tomographic images obtained by the above arithmetic process. The image forming part 220 forms a 3-dimensional image of the fundus oculi Ef by performing a publicly known interpolating process to interpolate an image between the adjacent tomographic images Gi and G (i+1).

Then, the image processing part 220 determines the arrangement and the distance of each scanning line Ri while referring to the positional information of each scanning line Ri to form this 3-dimensional image. For this 3-dimensional image, a 3-dimensional coordinate system (x,y,z) is set up, based on the positional information (said scan positional information) of each scanning point Rij and the z coordinate in the images of the depth direction.

Furthermore, based on this 3-dimensional image, the image processing part 220 is capable of forming a tomographic image of the fundus oculi Ef at a cross-section in an arbitrary direction other than the main scanning direction (x-direction). Once the cross-section is designated, the image processing part 220 determines the position of each scanning point (and/or an image in the depth direction that has been interpolated) on this designated cross-section, and extracts an image (and/or image in the depth direction that has been interpolated) in the depth direction at each determined position to form a tomographic image of the fundus oculi Ef at the designated cross-section by arranging a plurality of extracted images in the depth direction.

Furthermore, the image Gmj in FIG. 7 represents an image in the depth direction (z-direction) at the scanning point Rmj on the scanning line Rm. Likewise, an image in the depth direction at each scanning point Rij on the scanning line Ri formed by the arithmetic process of said first step may be represented as "image Gij."

[Operational Feature 1]

Figure 8:
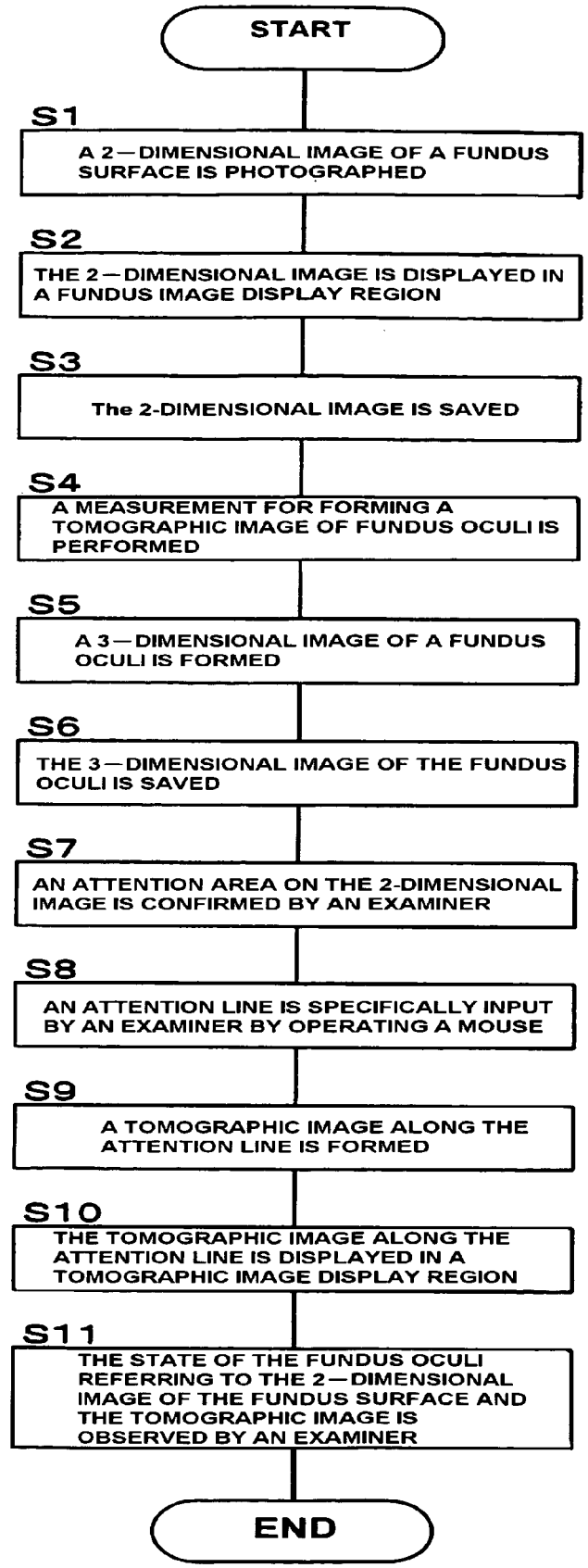
FIG. 8 is a flow chart representing one example of the operations in a favorable embodiment of the fundus observation device related to the present invention

The operations of such a fundus observation device 1 described above are explained referring to the flow chart shown in FIG. 8. This flow chart represents one feature of the obtaining processes of images of a fundus oculi Ef using a fundus observation device 1 and observations of the obtained images, particularly, representing one example of the display processes of the fundus images on a display 207 of a user interface 230.

First, using a fundus camera unit 1A, a 2-dimensional image of the surface of a fundus oculi Ef is photographed by an imaging device 10 (S1). The controlling part 210 of a computer 200 displays the 2-dimensional image that has been photographed on the user interface 230 (S2), and at the same time saves the image data of this 2-dimensional image in a storing device such as a hard disk drive 204, etc (S3).

Figure 9:
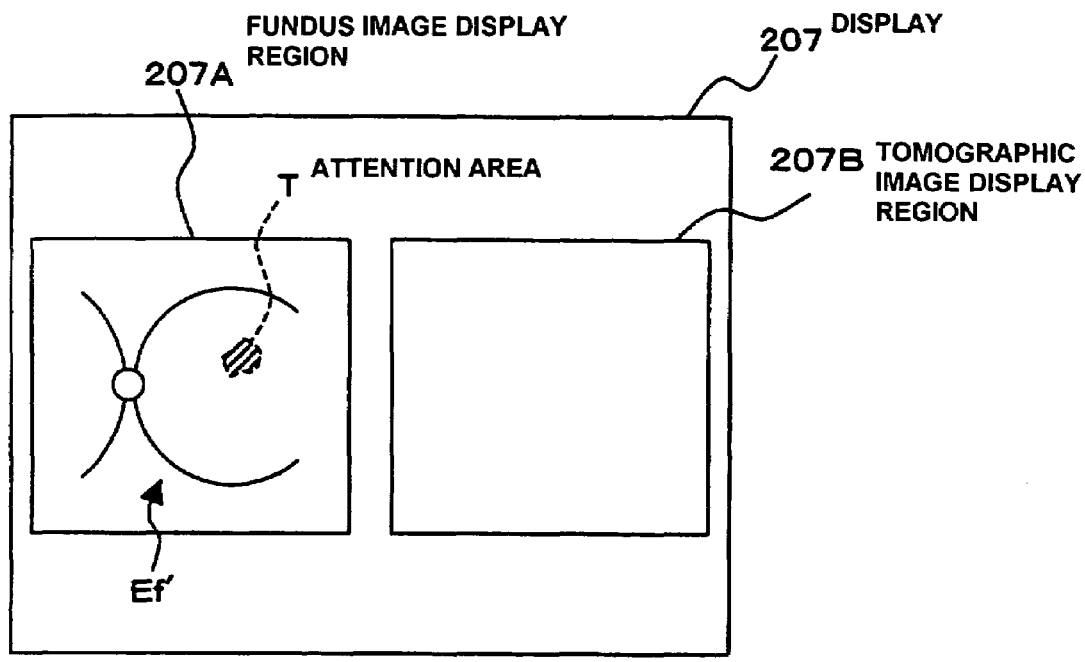
FIG. 9 is a schematic diagram representing one example of the display features of a fundus image in a favorable embodiment of the fundus observation device related to the present invention

FIG. 9 represents one example of the 2-dimensional images of a fundus oculi Ef to be displayed on the display 207 of the user interface 230. The controlling part 210 displays a fundus image display region 207A and a tomographic image display region 207B in parallel on the display 207 screen. In the fundus image display region 207A, the 2-dimensional image (fundus image Ef') of the fundus oculi Ef that has been photographed in Step 1 is displayed.

Furthermore, in the fundus image display region 207A, the coordinate system $(\xi,\eta)$ representing the position in this region 207A has been preset. For this coordinate system $(\xi,\eta)$, a 2-dimensional coordinate system representing the position of each pixel on the display 207 screen may be applied.

This coordinate system $(\xi,\eta)$ is used as image positional information representing the position on the 2-dimensional image (fundus image Ef') in the fundus image display region 207A. Furthermore, the coordinate system $(\xi,\eta)$ has been pre-associated with scan positional information (xy) in said xy coordinate system. As a result, the position within the fundus image display region 207A (particularly on the fundus image Ef') and the position in the partial coordinate system (xy) of said 3-dimensional coordinate (x,y,z) that has been set in a 3-dimensional image and is obtainable by using an OCT unit 150, etc. become associated to each other. Moreover, since a fundus image Ef' and a tomographic image are configured to be formed based on the light obtained through the same photographing optical system 120 (the optical axis thereof), the xy coordinate system in the xyz coordinate system is also defined with respect to the fundus image Ef'. Furthermore, the coordinate system $(\xi,\eta)$ is defined on the display 207 screen, and thus also defined in a tomographic image display region 207B. And the coordinate system $(\xi,\eta)$ in the tomographic display region 207B is associated with the xyz coordinate system of a tomographic image (3-dimensional image G).

Furthermore, an attention area T shown in FIG. 9 is indicating an area such as a lesion to which the examiner must pay attention for diagnosis. Whereas, the tomographic image display region 207B is a region for displaying the tomographic image of the fundus oculi Ef to be described later, which is formed, based on the detection signals obtained by the OCT unit 150.

Next, using the OCT unit 150 and the fundus camera unit 1A, a measurement to form a tomographic image of a fundus oculi Ef is conducted (S4). Then, the controlling part 210 controls the Galvanometer mirrors 141A and 141B and scans signal light LS on the fundus oculi Ef.

The image processing part 220: forms images Gij in the depth direction of the fundus oculi Ef at each scanning point Rij based on the detection signals that are output in order from the OCT unit 150; forms tomographic images Gi along each scanning line Ri based on these images Gij; and forms a 3-dimensional image of the fundus oculi Ef based on these tomographic images Gi (S5). The controlling part 210 saves the image data of (at least) this 3-dimensional image in a storing device such as a hard disk drive 204, etc.

The obtaining process of an image of a fundus oculi Ef of an eye to be examined E is now completed. Furthermore, the order of the obtaining process of a 2-dimensional image of the surface of a fundus oculi Ef (step S1 through S3) and the obtaining process of the tomographic image of the fundus oculi Ef (step S4 through S6) can be any, whichever comes first or later. Then, subsequently the examiner observes the fundus oculi Ef using these 2 types of images.

Figure 10:
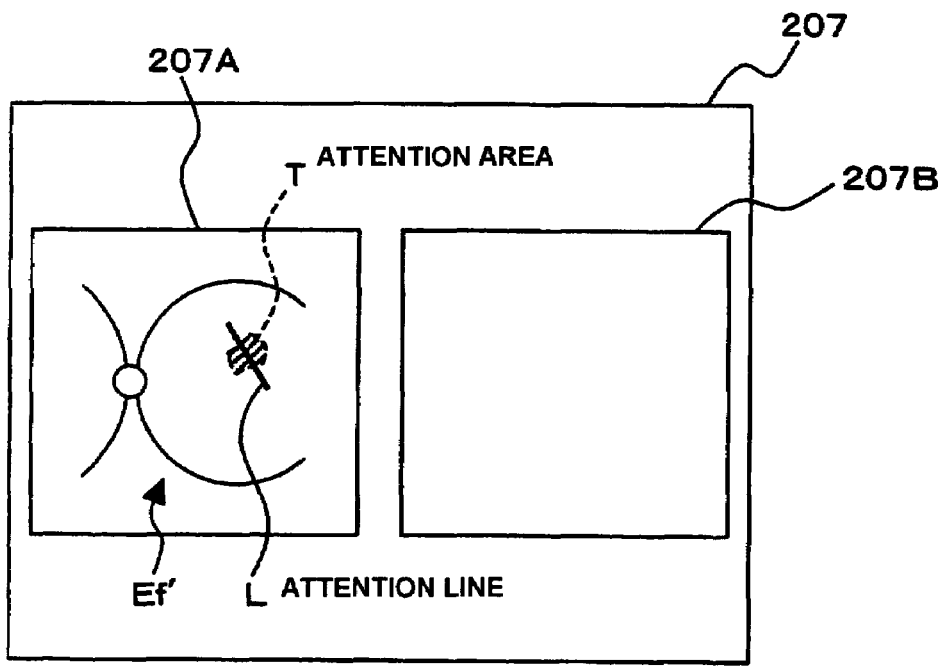
FIG. 10 is a schematic diagram representing one example of the display features of a fundus image in a favorable embodiment of the fundus observation device related to the present invention

First, the examiner observes the 2-dimensional image Ef' (ref. FIG. 9) displayed in the fundus image display region 207A of the display 207 to confirm the attention area T such as a lesion (S7), and specifically inputs a line (referred as an attention line) so as to pass this attention area as shown in FIG. 10 by operating e.g. a mouse 206 of the user interface 230 (S8).

The image processing part 220 forms a tomographic image along the attention line L based on the image data of the 3-dimensional image that has been saved in step S6 while referring to the associated information between said image positional information $(\xi,\eta)$ and said scan positional information (xy) (S9). The controlling part 210 displays the tomographic image along this attention line L in a tomographic image display region 207B (S10). Then, the fundus image display region 207A maintains the state in which the fundus image Ef' and the attention line L are displayed as in FIG. 10.

Figure 11:
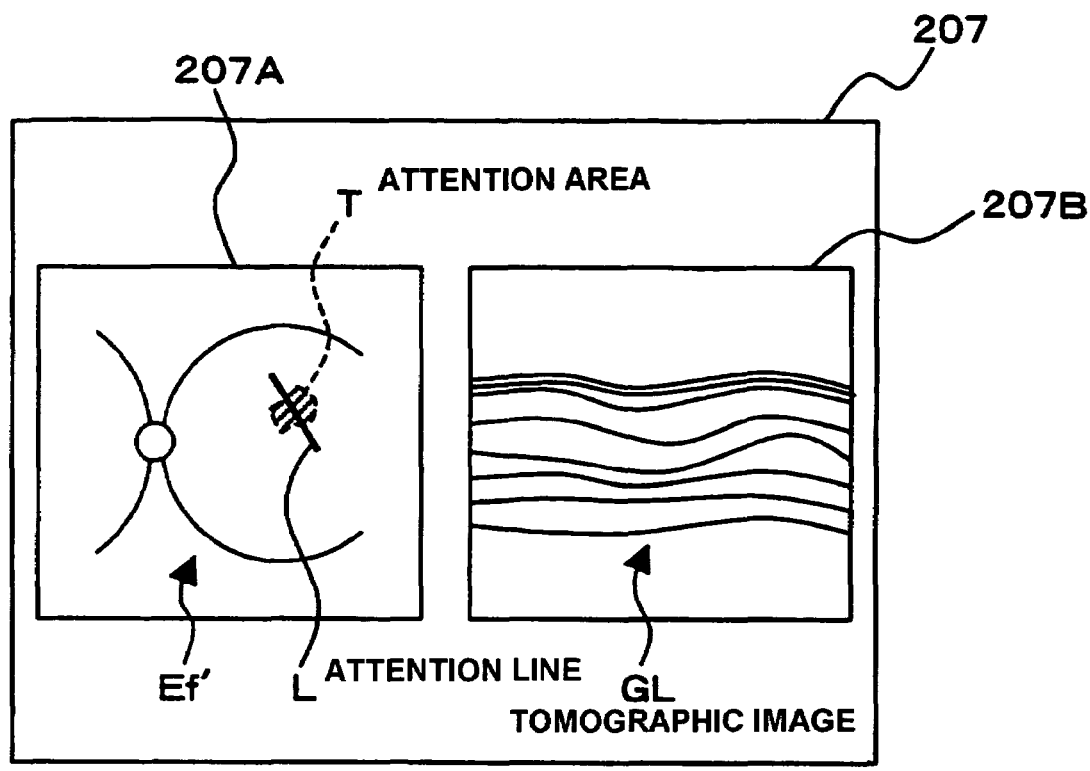
FIG. 11 is a schematic diagram representing one example of the display features of a fundus image in a favorable embodiment of the fundus observation device related to the present invention

FIG. 11 represents one example of display contents of the display 207 as in step S10. As shown in the same figure, a fundus image Ef' and an attention line L are shown in the fundus image display region 207A, and a tomographic image GL of the fundus oculi Ef whose cross-sectional position is the attention line L is shown in the tomographic image display region 207B. The examiner observes the state of the fundus oculi Ef referring to two types of images displayed in parallel (S11).

Furthermore, if one wishes to observe tomographic images at other cross-sectional positions, a new attention line L' (not illustrated) is specifically input on the fundus image Ef'. Accordingly, the display content in the fundus image display region 207A is shifted to the fundus image Ef' and the attention line L', and the display content in the tomographic image display region 207B is shifted to a tomographic image GL' whose cross-sectional position is the attention line L'.

[Operational Feature 2]

The operation of the fundus observation device 1 related to the present embodiment is not limited to the one described above; for example, the operation described below may be executable.

Figure 12:
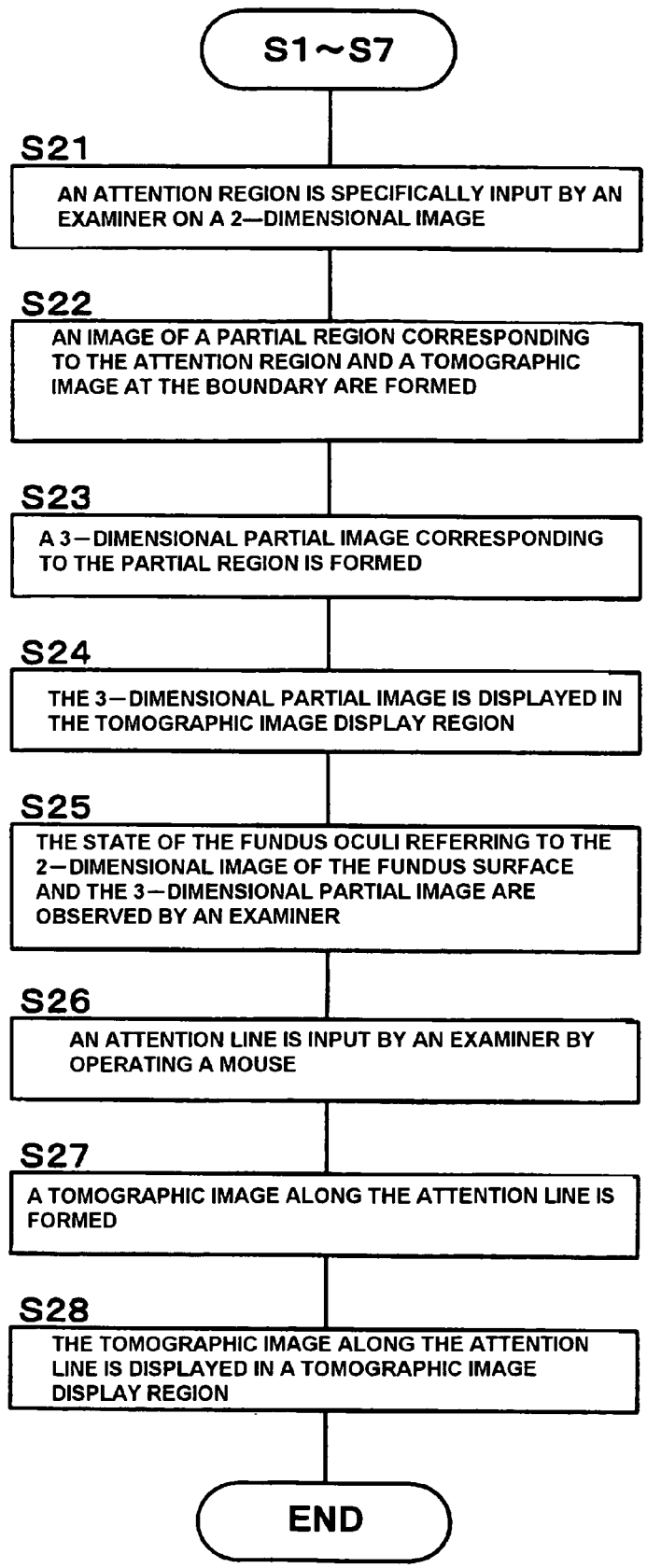
FIG. 12 is a flow chart representing one operational example in a favorable embodiment of the fundus observation device related to the present invention.

The flow chart shown in FIG. 12 represents an example of other operational features of the fundus observation device 1. Regarding the operational feature shown in the figure, the steps (step S1 through S7 in the flow chart of FIG. 8) up to the confirmation of an attention area on the 2-dimensional image (fundus image Ef') by the examiner are the same as the above Operational Feature 1.

After the examiner confirms an attention area T (ref. FIG. 9) on the 2-dimensional image (fundus image Ef') of the surface of a fundus oculi Ef (S7), the attention region including at least a part of this attention area T is input (S21). In capturing the sate of the attention area T, this attention region is a region to which the examiner wishes to pay particular attention.

Figure 13:
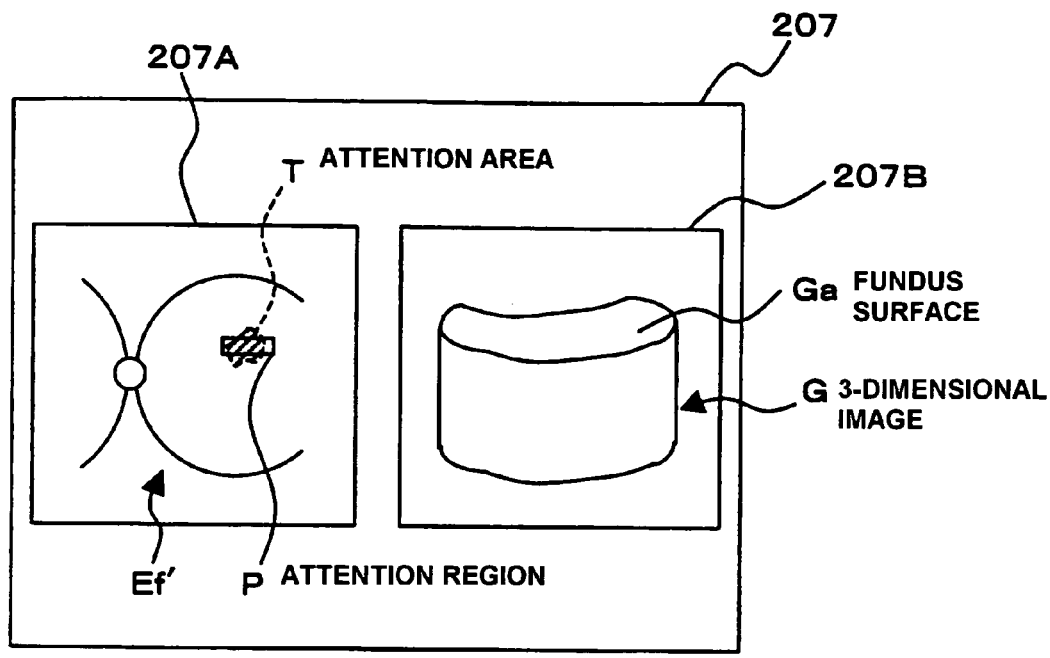
FIG. 13 is a schematic diagram representing one example of the display features of a fundus image in a favorable embodiment of the fundus observation device related to the present invention.

FIG. 13 represents one example of designated features of this attention region. The attention region P specifically input with respect to the attention area T of a fundus image Ef' designated in the fundus image display part 207A in the same figure is supposed to be a rectangular shaped region.

In order to designate such an attention region P, the examiner, for example, designates a position (one point) indicated by a mouse pointer by pressing the mouse button when the mouse pointer is pointing at the desired position on the fundus image display region 207A by operating the mouse 206 of the user interface 230, and while maintaining the pressed state, designates the other point by moving the mouse pointer to the other point and releasing the mouse button from the state of being pressed (the same operation generally know as "drag"). As a result, a rectangular shaped region with these two points as both ends of the diagonal is specifically input.

Furthermore, the attention region, in general, is not limited to a rectangular shaped region as shown in FIG. 13, the region can be any arbitrary shape such as a circular shape or an oval shape. Moreover, the operational method of specifically inputting an attention region does not have to be limited to the operational method described above, for example, handwritten input using an inputting device such as a pentablet, or any arbitrary method may be used appropriately.

Furthermore, in the tomographic image display region 207B of FIG. 13, a 3-dimensional image G formed in step S5 is displayed. A fundus surface Ga of this 3-dimensional image G is an equivalent of a fundus image Ef'.

Once the attention region P is specifically input by the examiner (S21), an image processing part 220 forms an image of the partial region of the 3-dimensional image corresponding to this attention region P and a tomographic image at the boundary of this partial region, based on the 3-dimensional images of a fundus oculi Ef formed in step S5 (S22).

Herein, the partial region of the 3-dimensional image corresponding to the attention region P means a collection of images in the depth direction of each point within this attention region P. That is, in the entire 3-dimensional image, only the 3-dimensional region extending in the depth direction (z-direction) of the 2-dimensional attention region P is extracted to form an image.

Figure 14:
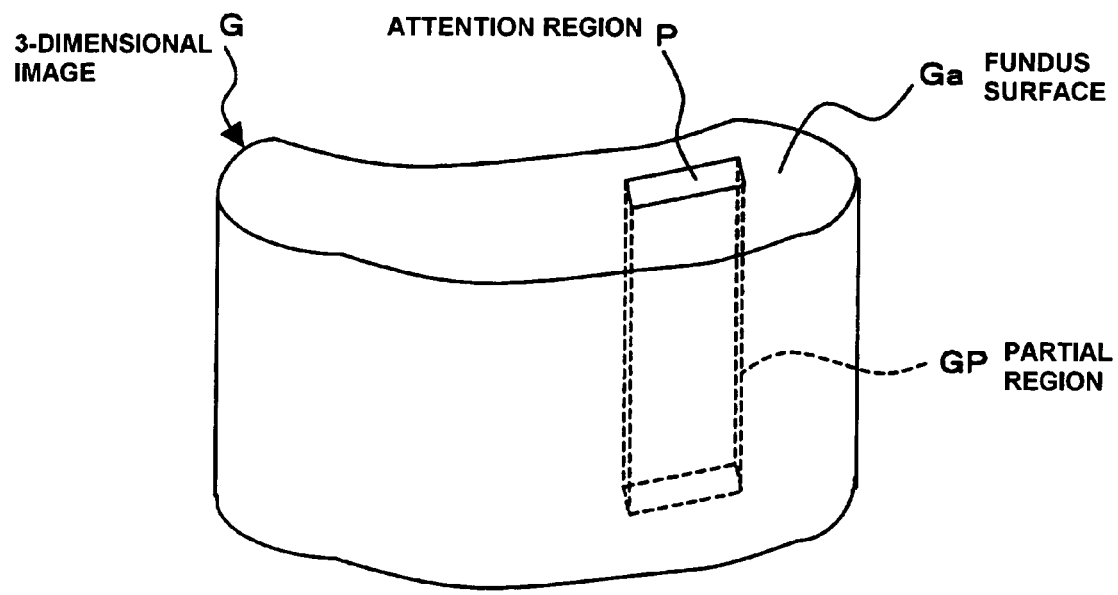
FIG. 14 is a schematic diagram to explain a partial region of a 3-dimensional image formed by a favorable embodiment of the fundus observation device related to the present invention.

FIG. 14 shows one example of a partial region GP of a 3-dimensional image G, that corresponds to the attention region P on the fundus image Ef'. Furthermore, this partial region GP includes not only the area indicated by the dotted line, but also the attention region P itself.

Such a partial image may be formed, for instance, by extracting images in the depth direction at each point within the attention region P from the entire 3-dimensional image.

Moreover, a tomographic image at the boundary position of a partial region means, in the entire 3-dimensional image, a tomographic image of the boundary that divides the internal region and the external region of the partial image. Such a tomographic image, for example, may be formed by extracting the image in the depth direction at each point of the boundary of an attention region P At the boundary of a partial region corresponding to the attention region P that is formed in step S22, by synthesizing the tomographic images formed in step 22, the image processing part 220 forms an image representing the state when the partial region is cut out from the entire 3-dimensional image S23). This image is a 3-dimensional image and is the equivalent of one example of a "3-dimensional partial image" referred to in the present invention.

Figure 15:
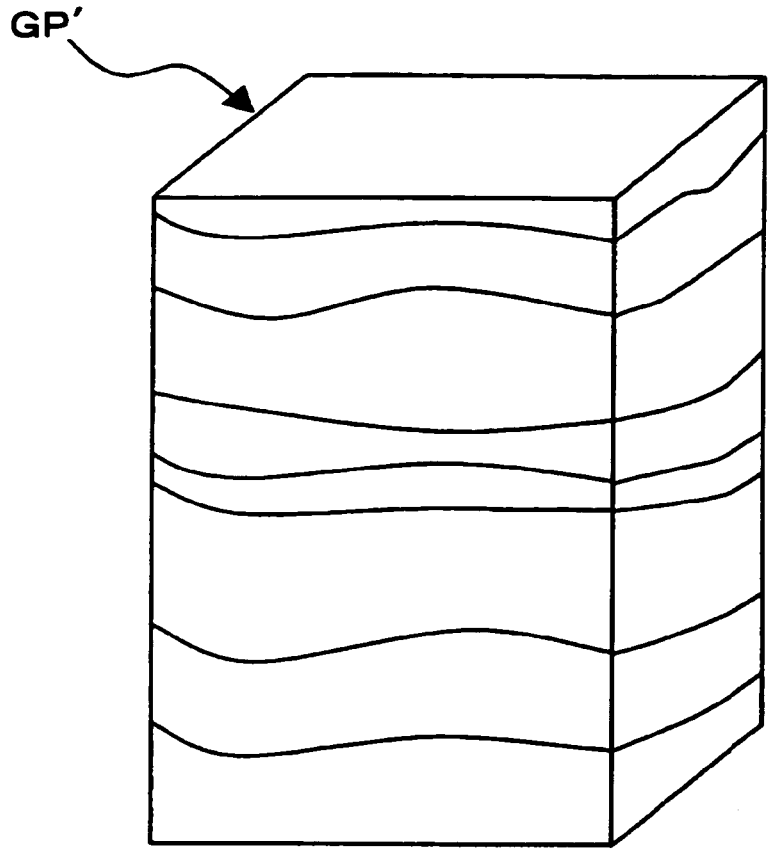
FIG. 15 is a schematic diagram to explain a 3-dimensional partial image formed in a favorable embodiment of the fundus observation device related to the present invention.

In FIG. 15, one example of the formation of a 3-dimensional partial image is shown. The 3-dimensional partial image GP' shown in the figure is a 3-dimensional partial image corresponding to the partial region GP in FIG. 14. The side face (boundary face) of this 3-dimensional partial image GP' has a synthesized tomographic image respectively.

A controlling part 210 displays the 3-dimensional partial image formed in step S23 in the tomographic image display region 207B. Then, in the fundus image display region 207A, as in FIG. 13, a fundus image Ef' and an attention region P are displayed.

Figure 16:
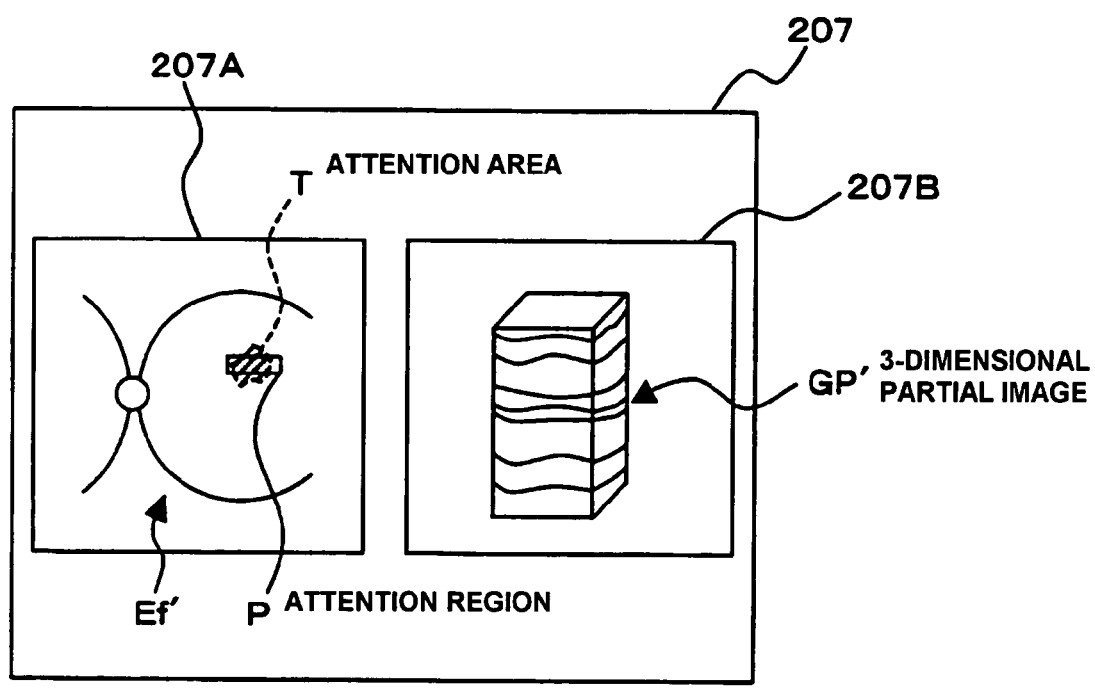
FIG. 16 is a schematic diagram representing one example of the display features of a fundus image in a favorable embodiment of the fundus observation device related to the present invention.

FIG. 16 shows one example of display contents of the display 207 as of step S24. As shown in the figure, in the fundus image display region 207A, a fundus image Ef' and an attention region P are displayed, while in the tomographic image display region 207B, a 3-dimensional partial image GP' of the fundus oculi Ef, corresponding to the attention region P is displayed. The examiner observes the state of the fundus oculi Ef referring to the 2 types of images displayed in parallel (S25).

Moreover, when one wishes to observe a tomographic image at a certain cross-sectional position of this 3-dimensional partial image GP', as in Operational Feature 1 that has been previously described (ref. step S8 in FIG. 8), by operating the mouse 206 of the user interface 230 the attention line on the attention region P of a fundus image Ef' is specifically entered (S26).

The image processing part 220 forms a cross-sectional image along with this attention line, based on the image data of the 3-dimensional partial image GP' (S27). The controlling part 210 displays a tomographic image along this attention line in the tomographic image display region 207B (S28). Then, in the fundus image display region 207A, a fundus image Ef', an attention region P and the attention line is displayed (the illustration omitted).

Furthermore, when one wishes to observe a 3-dimensional partial image in other attention regions, the examiner specifically inputs a new attention region Q (not illustrated) on the fundus image Ef'. Accordingly, the display contents of the fundus image display region 207A is shifted to the fundus image Ef' and the attention region Q, the display contents of the tomographic image display region 207B is shifted to a 3-dimensional partial image GQ' corresponding to the attention region Q.

Moreover, when one wishes to observe a tomographic image along the other attention line, the tomographic image is displayed, when the desired attention line is specifically input as in the above Operational Feature 1.

[Action Effect]

According to the above fundus observation device 1 related to the present embodiment, the following actions and effects are expected.

This fundus observation device 1 is characterized in comprising: (1) a fundus camera unit 1A for forming a 2-dimensional image Ef' of the surface of a fundus oculi Ef of an eye to be examined E, (2) an OCT unit 150 and an image processing part 220 of a computer 200 for forming a tomographic image Gi, etc. of the fundus oculi Ef, (3) a display 207 of the computer 200, (4) a controlling part 211 for displaying the 2-dimensional image Ef' formed by the fundus camera unit 1A and the tomographic image Gi formed by the image processing part 220, etc. in parallel on the display 207, and at the same time for displaying the cross-sectional position information (attention line L, attention region P) indicating the cross-sectional position of the tomographic image Gi, etc. on the surface of the fundus oculi Ef, so as to be overlapped with the 2-dimensional image Ef'.

Therefore, according to this fundus oculi observation device 1, a 2-dimensional image Ef' of the surface of a fundus oculi Ef and a tomographic image Gi, etc. of the fundus oculi Ef are displayed in parallel on the display 207, while the cross-sectional position information indicating the cross-sectional position of the tomographic image Gi, etc. is displayed on the 2-dimensional image Ef' (ref. FIG. 11, FIG. 16), and thus the examiner can capture the position of the tomographic image Gi, etc, on the 2-dimensional image Ef' easily at a glance. As a result, the positional relation of the 2-dimensional image Ef' and the tomographic image Gi, etc. to each other may be captured easily.

Furthermore, as shown in FIG. 1, the fundus observation unit 1 is configured so as to emit the signal light LS from the OCT unit 150 to the fundus oculi Ef through an optical path (a part thereof) of the photographing optical system 120 of the fundus camera unit 1A, and guide the fundus reflection light of the signal light to the OCT unit 150 again through the optical path (a part thereof) of the photographing optical system 120.

Therefore, due to the configuration, both the 2-dimensional image Ef' of the surface of the fundus oculi Ef to be photographed by the fundus camera unit 1A and the tomographic image Gi, etc. of the fundus oculi Ef formed by the OCT unit 150, etc. may be obtained based on the fundus reflection light having been guided along the same optical path so as to be able to map the positional relation of both images easily. Furthermore, in the present embodiment, according to the xy coordinate plane in the xyz coordinate system shown in FIGS. 1, 6 and 7, the positional relation of the 2-dimensional image Ef' of the surface of the fundus oculi Ef and the tomographic image Gi, etc. are made to be associated to each other.

Furthermore, the fundus observation device 1 is further provided with a user interface 230 (a mouse 206 thereof) and with a scanning unit 141 in the fundus camera unit 1A for scanning the incident position of signal light LS with respect to the fundus oculi Ef in a main scanning direction (x-direction) and in a sub-scanning direction (y-direction) respectively. Moreover, the image processing part 220 of the computer 200 forms: tomographic images G1 through Gm along the main scanning direction corresponding to the scanning line R1 through Rm of a plurality of positions in different sub-scanning direction respectively; a 3-dimensional image of the fundus oculi Ef based on the tomographic images G1 through Gm; a tomographic image GL at a position based on the 3-dimensional image, when the cross-sectional position (attention line L) is designated (ref. FIG. 10) by the user interface 230 on the 2-dimensional image Ef' displayed on the display 207. Then, the controlling part 210 displays this tomographic image GL and the 2-dimensional image Ef' in parallel, and at the same time displays the cross-sectional position information (attention line L) indicating the cross-sectional position L, so as to be overlapped with the 2-dimensional image Ef' (re. FIG. 11).

Thus, in accordance with the desired cross-sectional position having been designated on the 2-dimensional image Ef' of the fundus oculi Ef displayed on the display 207, the tomographic image at this cross-sectional position is displayed on the display 207 parallel to the 2-dimensional image Ef', and additionally, the information indicating the cross-sectional position is displayed on the 2-dimensional image Ef'. Therefore, the state of the cross-section at the desired position of the fundus oculi Ef may be observed in detail, and at the same time, the position of the cross-section of the fundus oculi Ef may be captured easily.

Furthermore, as shown in FIG. 14, the image processing part 220 of the computer 200 forms an image of an arbitrary partial region GP of the 3-dimensional image G of the fundus oculi Ef and a tomographic image at the boundary of this partial region GP, and forms a 3-dimensional partial image GP'' corresponding to the partial region GP (ref. FIG. 15) based on the image of the partial region GP and the tomographic image at the boundary. As shown in FIG. 16, the controlling part 210 displays the formed 3-dimensional partial image GP on the display 207 parallel to the 2-dimensional image Ef', and at the same time, displays the cross-sectional position information (attention region P) indicating the boundary of the partial region GP so as to be overlapped with the 2-dimensional image Ef.

As a result, the state of an arbitrary partial region GP of a 3-dimensional image G of a fundus oculi Ef may be observed easily, and also the position of the partial region GP on a 2-dimensional image Ef' may be captured easily.

Moreover, the fundus observation device 1 is provided with a user interface 230 (a mouse 206 thereof) for designating a partial region GP of the 3-dimensional image G of a fundus oculi Ef. By specifically designating an attention region P on a 2-dimensional image Ef' by operating the mouse 206, the examiner may designate the partial region GP that corresponds to this attention region P. Accordingly, the desired position in the 3-dimensional image G may be observed in detail, and at the same time, the position on the 2-dimensional image Ef' of the desired position may be captured easily.

Furthermore, the fundus observation device 1 displays a tomographic image at a cross-sectional position in the partial region GP of a 3-dimensional image G parallel to a 2-dimensional image Ef', and also the cross-sectional position information indicating the cross-sectional position is displayed on the 2-dimensional image Ef, and thus the state of an arbitrary cross-section in the partial region GP may be observed in detail.

[Modified Example]

The constitution described in detail thus far in the Embodiment 1 is only an example of concrete constitutions to favorably implement the fundus observation device, the fundus image display device, and the fundus observation program, related to the present invention. That is, the fundus observation device, the fundus image display device, and the fundus observation program, related to the present invention are not limited to the constitution described above, but for example, the following arbitrary modification described below may be implemented appropriately.

A first image forming means of the fundus observation device related to the present invention is not limited to a fundus camera (unit), an arbitrary photographing device capable of forming a 2-dimensional image of a fundus surface may also be applied. For example, a slit lamp (slit lamp microscopic device) may be used as a first image forming means.

Likewise, the second image forming means is not limited to Optical Coherence Tomography (OCT device, OCT unit); for example, a transillumination CT device, a Photoacoustic Tomography device, a Confocal Microscope, etc. may also be used.

Furthermore, in the embodiment above, the constitution is adopted so that the signal light LS from the OCT unit 150 (a second image forming means) is guided to the eye to be examined E through a part of the optical path of the photographing optical system 120 of the fundus camera unit 1A (a first image forming means); however, in the present invention, generally this is not required. That is, it is also possible to adopt a constitution so as to obtain the position of cross-sectional position information on a 2-dimensional image, by arranging each unit (device) individually and calculating the positional relations among images to be formed, based on the positional relations among the units. However, the above embodiment seems to be simpler in terms of the device constitution, and more favorable as the processing time by the time the image is displayed is short.

Moreover, in the above embodiment, it is configured so that one computer 200 executes both image forming processes (image processing part 220) and display controlling process (controlling part 210); however, it is also possible to apply a configuration in which these processes may be executed by a separate computer respectively.

Embodiment 2

Embodiment 2 of the fundus observation device related to the present invention is described.

In this embodiment, when an examiner designates one point on one of two images displayed in parallel, the information (designated positional information) is displayed on the other image at a position corresponding to this designated one point.

Moreover, in the present embodiment, when one point on the display image is designated, the other image including this designated one point is formed, and the information (designated positional information) is displayed at a position corresponding to the one point on the other image. In addition,

[Constitution]

Figure 17:
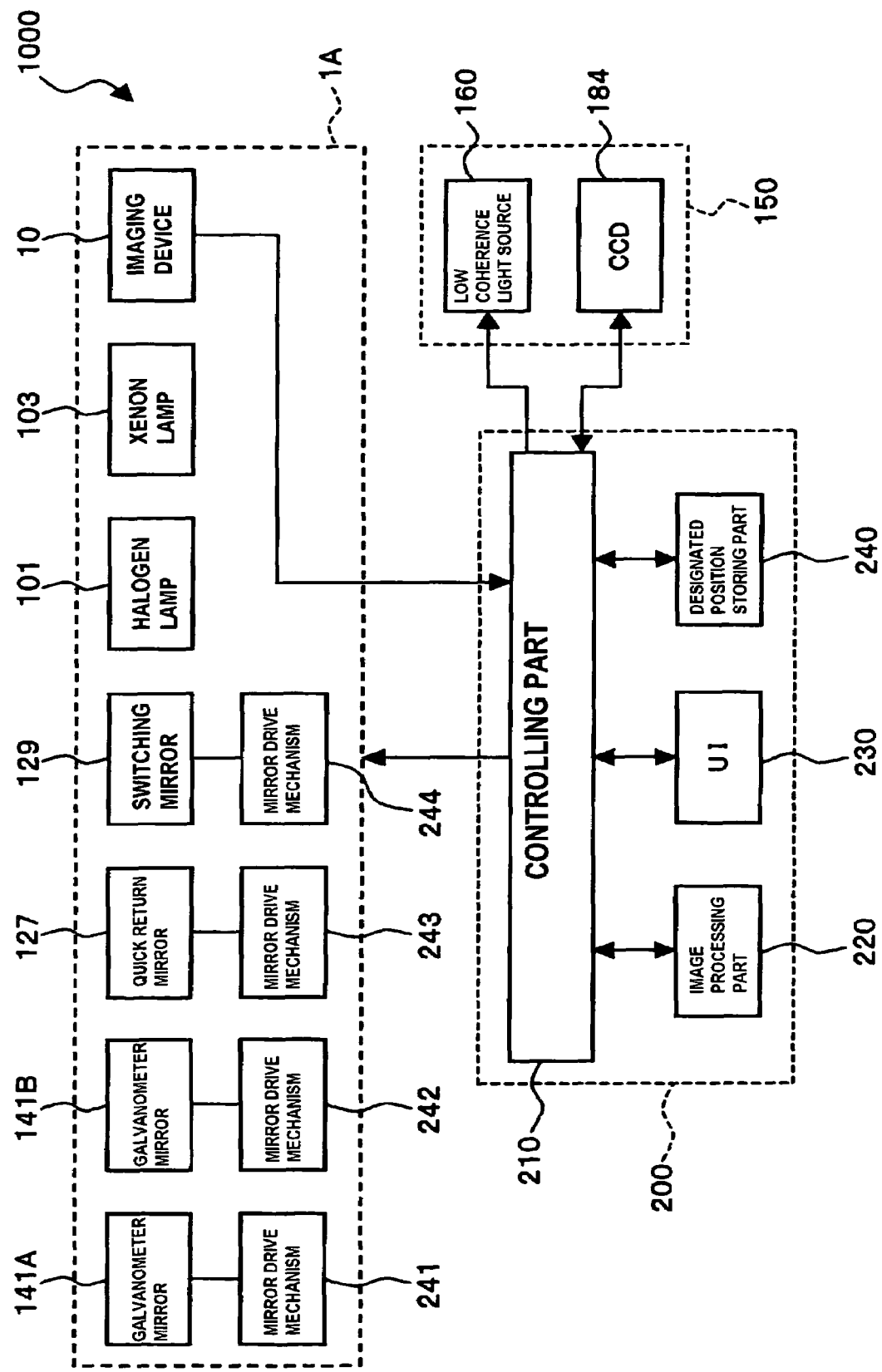
FIG. 17 is a schematic block diagram representing one compositional example of a control system in a favorable embodiment of the fundus observation device related to the present invention.

One configuration example of the control system of the fundus observation device related to the present embodiment is shown in FIG. 17. This fundus observation device 1000 is provided with an optical system, hardware, and an appearance as in Embodiment 1 (ref. FIGS. 1 through 4, FIG. 42). Furthermore, the fundus observation device 1000 is provided with a fundus camera unit 1A, an OCT unit 150 and a computer 200 as in Embodiment 1.

The computer 200 of the fundus observation device 1000 is equipped with a designated position storing part 240 for storing coordinate values of the position (one point) designated by the examiner with respect to the image displayed on a display 207 (display means). This designated position storing part 240 functions as one example of a "storing means" in the present invention and comprises a storing device, for example, a hard disk drive 204, etc. The storing process of the information with respect to the designated position storing part 240 and the read-out process of the information from the designated position storing part 240 are executed by a controlling part 210 (CPU 201).

While the operations of the controlling part 210 are mainly explained below, the operational features (Operational Features 1 though 8) and their action effects of the fundus observation device 1000 related to the present embodiment are also described. Furthermore, each operational feature is executed following a control program 204a shown in FIG. 4.

[Operational Feature 1]

Figure 18:
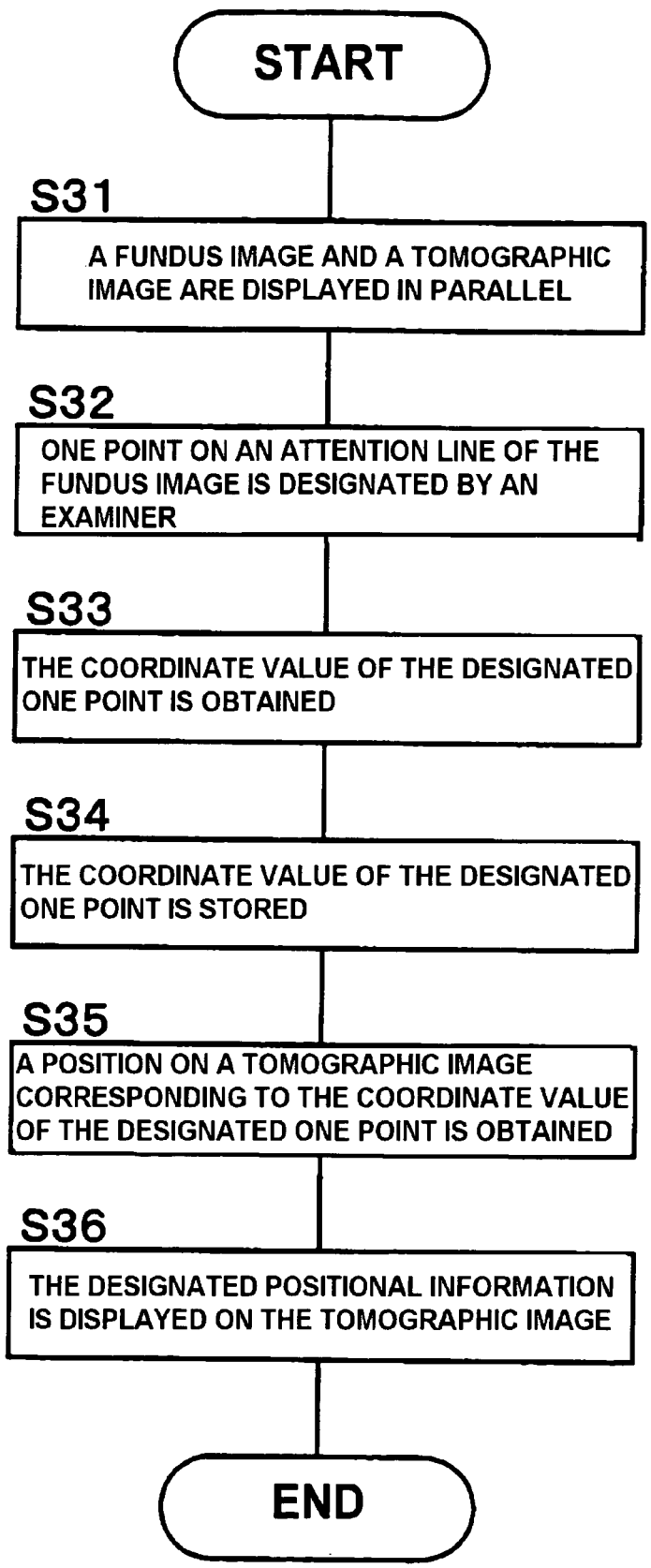
FIG. 18 is a flow chart representing one operational example in a favorable embodiment of the fundus observation device related to the present invention.

The first operational feature of this fundus observation device 1000 is described referring to the flow chart shown in FIG. 18. With this operational feature, one example of the operations of the fundus observation device 1000 is explained for the case when the examiner designates one point on a 2-dimensional image, while a 2-dimensional image (fundus image) of a fundus surface and a tomographic image of the fundus oculi are displayed on a display 207 (S31).

Figure 19:
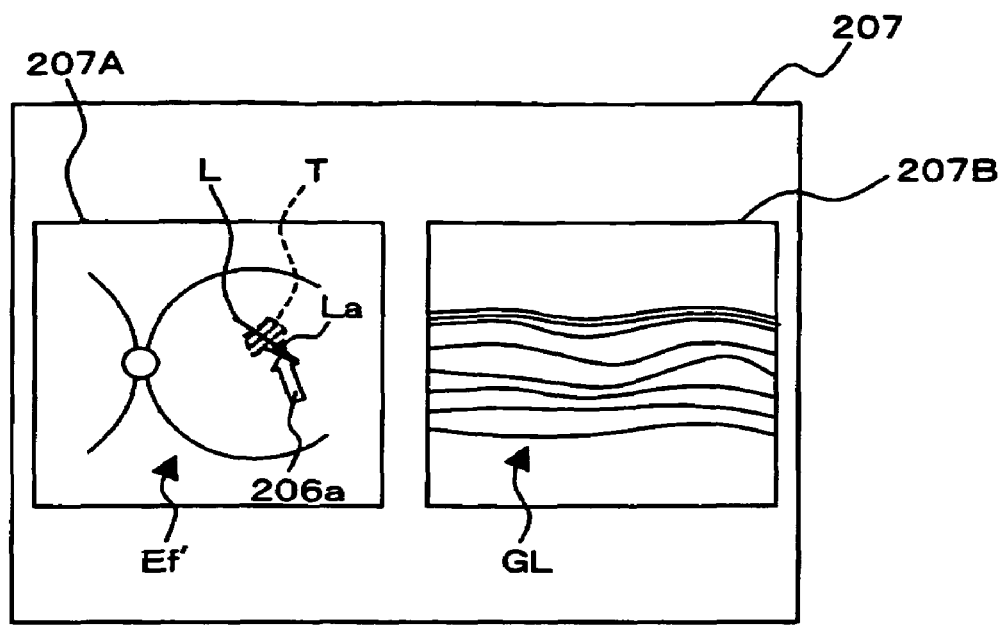
FIG. 19 is a schematic diagram representing one example of the display features of a fundus image in a favorable embodiment of the fundus observation device related to the present invention.

FIG. 19 represents one example of the display features of a 2-dimensional image (fundus image Ef) and a tomographic image of a fundus surface. These images are displayed, for example, on the display 207 in accordance with the procedure that was explained in Embodiment 1 (ref. FIG. 11).

For this display 207, a fundus image display region 207A and a tomographic image display region 207B are provided. In the fundus image display region 207A, a fundus image Ef and an attention line L are displayed. Furthermore, in the tomographic display region 207B, a tomographic image GL of a fundus oculi Ef, whose cross-sectional position is the attention line L on the fundus image Ef, is displayed.

On the display 207 shown in FIG. 19 is a mouse pointer 206a that moves a display position through operation of the mouse 206.

As shown in FIG. 19, by operating the mouse 206 to point to one point (an area to be focused on particularly) La on the attention line L and then clicking, the one point La is designated (S32). The information (coordinate value) indicating the position of the designated one point La is sent to the controlling part 210 from a user interface 230.

The coordinate value of the one point La on the attention line L is, for example, a coordinate value $(\xi a, \eta a)$ represented by the 2-dimensional coordinate system $(\xi, \eta)$ that shows a pixel position on the display 207 as explained in Embodiment 1.

The controlling part 210 converts the coordinate value $(\xi a, \eta a)$ of the one point to obtain a coordinate value (xa,ya) of the one point La in the xy coordinate system defined in the fundus image Ef (the image data thereof) (S33). Then, the controlling part 210 stores the coordinate value (xa,ya) of this one point La in the designated position storing part 240 (S34). Then, also with regard to the z coordinate value za (z coordinate value equivalent of the surface of a fundus oculi Ef) of the one point La, the arithmetic may be performed so as to be stored.

Additionally, the controlling part 210 obtains a position on a tomographic image GL that corresponds to the coordinate value (xa,ya) of the one point La obtained in step S33 (S35). For this, for example, a straight line {(xa,ya,z):z=any} that passes through the coordinate value (xa,ya) and yet extends in the z-direction (depth direction) is obtained (this straight line becomes a position on the tomographic image GL, that corresponds to the coordinate value (xa,ya).

Figure 20:
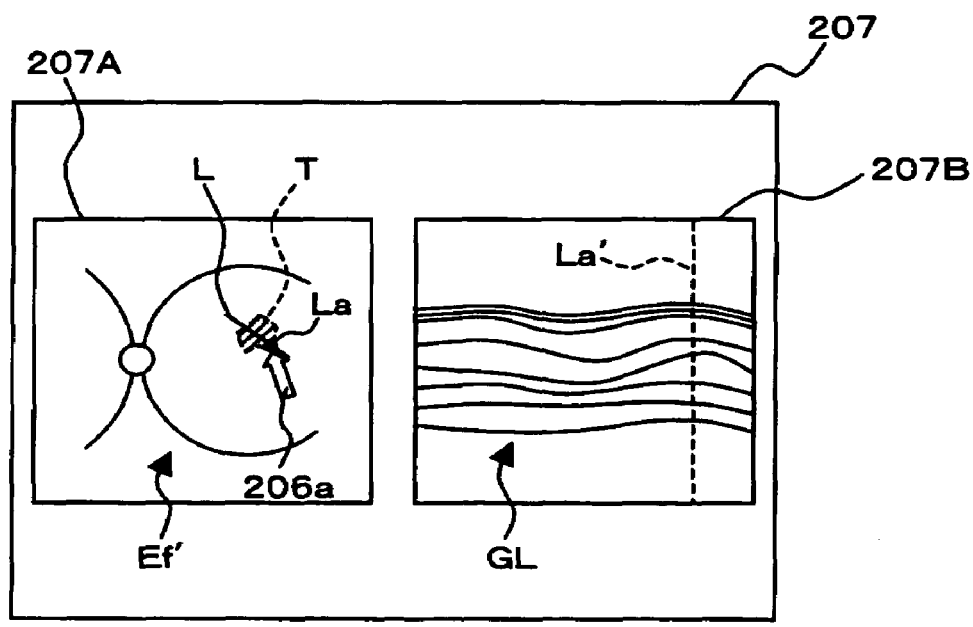
FIG. 20 is a schematic diagram representing one example of the display features of a fundus image in a favorable embodiment of the fundus observation device related to the present invention.

Moreover, the controlling part 210 displays the designated positional information indicating a position on the tomographic image GL that corresponds to the one point La that was obtained in step S35, so as to be overlapped with the tomographic image GL displayed in the tomographic image display region 207B (S36). Then, based on the association of the xyz coordinate system explained in Embodiment 1 and the $\xi\eta$ coordinate system, the controlling part 210 converts the straight line {(xa,ya,z):z=any} obtained in step S35 to the $\xi\eta$ coordinate system (the $\xi\eta$ coordinate system defined in the tomographic image display region 207B) and displays a designated positional information La' along the straight line obtained thereby. FIG. 20 represents one example of the display features of the designated positional information La' obtained accordingly.

Furthermore, the information (coordinate value) indicating the designated position (one point La) stored in the designated position storing part 240 in step S34 is read-out by the controlling part 210 when the image is observed later (e.g. when comparing with past images, for example, in follow-up observations). Then, based on the information that has been read-out, the designated positional information (La') is displayed on the tomographic image GL.

In the present operational feature, the designated positional information is displayed only on the tomographic image GL; however, it may also be configured to display the designated positional information on the fundus image Ef'. For example, in step S32 when one point La on the fundus image Ef' is designated, the designated positional information may be displayed at this one point La.

Moreover, in the present operational feature, after moving the mouse pointer 206a to the desired position on a fundus Ef', by clicking, the designated position is confirmed (ref. step S32); however, for example, it may also be configured to display the designated positional information on the tomographic image GL following the movement of the mouse pointer 206a on the fundus image Ef'.

According to the present operational feature, with respect to the fundus image Ef' and the tomographic image GL to be displayed in parallel, once the position (one point La) on the fundus image Ef' is designated, the designated positional information (La') is displayed on the tomographic image GL at a position corresponding to the designated position, and therefore, the examiner may easily capture the relation of the position on the fundus image Ef' and the position on the tomographic image GL.

[Operational Feature 2]

Figure 21:
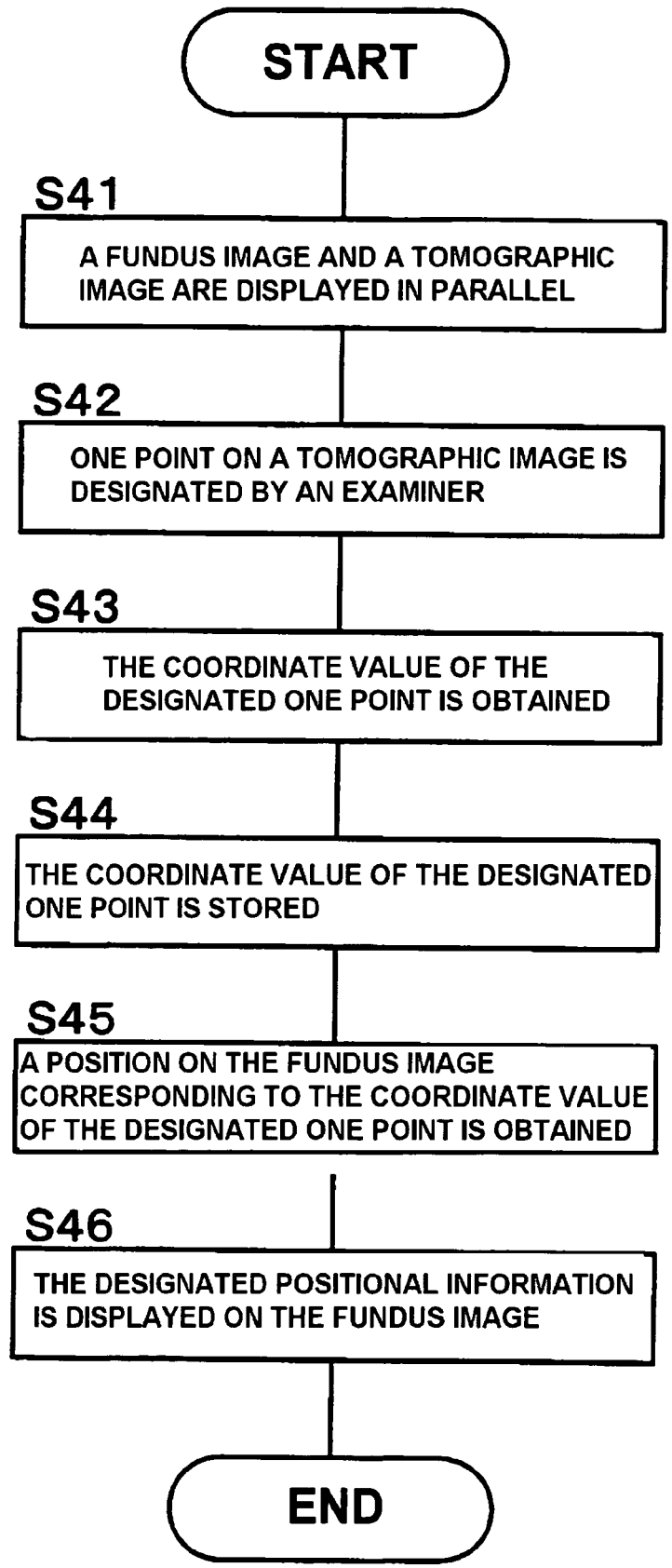
FIG. 21 is a flow chart representing one operational example in a favorable embodiment of the fundus observation device related to the present invention.

Next, the second operational feature of the fundus observation device 1000 is described referring to the flow chart shown in FIG. 21. In this operational feature, one example of the operations of the fundus observation device 1000 is explained in the case when the examiner designates one point on a tomographic image, while a 2-dimensional image (fundus image) of a fundus surface and a tomographic image of the fundus are displayed in parallel on the display 207 (S41).

Figure 22:
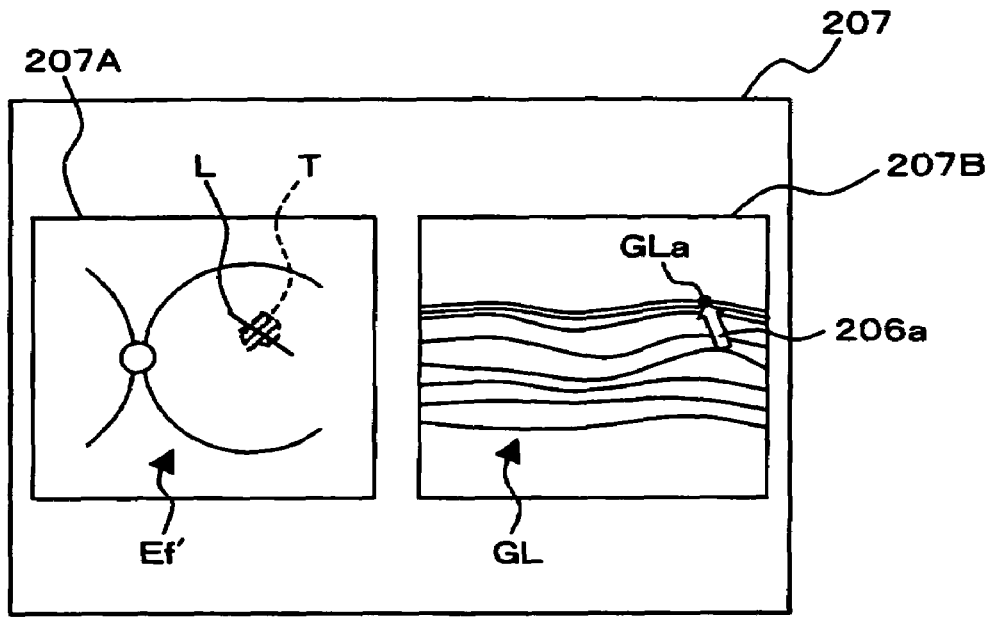
FIG. 22 is a schematic diagram representing one example of the display features of a fundus image in a favorable embodiment of the fundus observation device related to the present invention.

FIG. 22 represents one example of the display features of a fundus image Ef' and a tomographic image GL. These images are displayed, for example, on the display 207 in accordance with the procedure that was explained in Embodiment 1 (ref. FIG. 11).

As shown in FIG. 22, by operating the mouse 206 with the mouse pointer 206a to point to one point GLa on an image region that is an equivalent of the fundus surface in a tomographic image GL and clicking, the one point GLa is designated (S42). The information indicating the position of the designated one point GLa (coordinate value) is sent to the controlling part 210 from the user interface 230.

The coordinate value of the one point GLa on the tomographic image GL is represented by a coordinate value ($\xi b$, $\eta b$) in the $\xi\eta$ coordinate system.

The controlling part 210 converts the coordinate value ($\xi b,\eta b$) of the one point GLa to obtain a coordinate value (xb,yb,zb) of the one point GLa in the xyz coordinate system defined in the tomographic image GL (3-dimensional image G) (S43). Then, the controlling part 210 stores the coordinate value (xb,yb,zb) of this one point GLa in the designated position storing part 240 (S44).

Furthermore, the controlling part 210 obtains a position on a fundus image Ef' that corresponds to the coordinate value (xb,yb,zb) of the one point GLa obtained in step S43. For this, for example, based on the fact that in the fundus image Ef' the z coordinate value in the xyz coordinate system is not taken into a consideration, the coordinate value (xb,yb) is to be obtained by projecting the coordinate value (xb,yb,zb) of the one point GLa onto a xy coordinate plane (parallel to the face equivalent of the fundus surface) (this coordinate value becomes a position on the fundus image corresponding to the coordinate value (xb,yb,zb) of the one point GLa.

Figure 23:
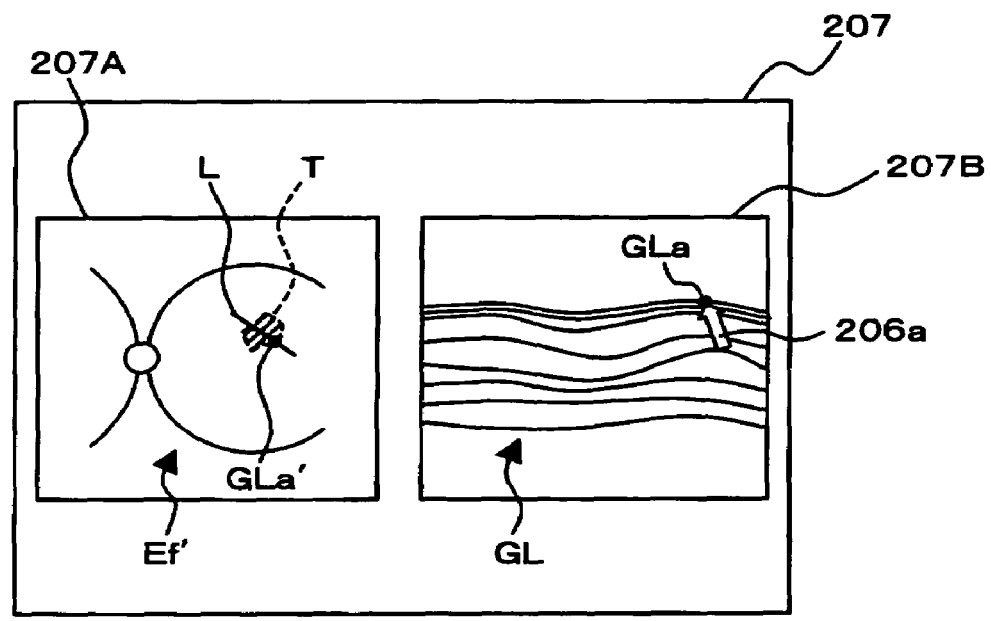
FIG. 23 is a schematic diagram representing one example of the display features of a fundus image in a favorable embodiment of the fundus observation device related to the present invention.

Furthermore, the controlling part 210 displays a designated positional information GLa' indicating a position on the fundus image Ef', that corresponds to the one point GLa obtained in step S45, so as to be overlapped with the fundus image Ef' displayed in the fundus image display region 207 (S46). Then, based on the association of the xyz coordinate system explained in Embodiment 1 and the $\xi\eta$ coordinate system, the controlling part 210 converts the coordinate value (xb,yb) obtained in step S45 to the $\xi\eta$ coordinate system (the $\xi\eta$ coordinate system defined in the fundus image display region 207A), and displays the designated positional information GLa' on the fundus image Ef' at a position to be specified by a coordinate value ($\xi b'$,$\eta b'$) that has been obtained accordingly. FIG. 23 represents one example of the display features of the designated positional information GLa' obtained as described.

Furthermore, the information (coordinate value) indicating the designated position (one point GLa) stored in the designated position storing part 240 in step S44, is read-out later when the image is observed, and the designated positional information (GLa') is displayed on the fundus image Ef'.

In the present operational feature, the designated positional information is displayed only on a fundus image Ef'; however, it may also be configured to display the designated positional information at a designated position (position of one point La) on a tomographic image GL.

Additionally, in the present operational feature, after moving the mouse pointer 206a to a desired position on the tomographic image GL by clicking, the designated position is confirmed (ref. step S42); however, for example, it may also be configured to display the designated positional information on the fundus image Ef' following the movement of the mouse pointer 206a on the tomographic image GL.

Furthermore, in the present operational feature, a process to be executed has been explained in the case when one point on an image region equivalent of a fundus surface in a tomographic image GL is designated; however, the same process may be executed in the case when a position (one point) deeper than the fundus surface is designated. For example, By presetting the $\eta$ coordinate value $\eta 0$ of a position equivalent of a fundus surface, when the position equivalent of a deep area of the fundus oculi in a tomographic image GL is designated, by executing the above process with respect to the ($\xi b,\eta 0$)) to be obtained from converting the coordinate value $\eta b$ of a coordinate value ($\xi b$, $\eta b$) of the designated position to $\eta 0$, the same result may be obtained.

According to the present operational feature, with respect to the fundus image Ef' and the tomographic image GL to be displayed in parallel, once the position (one point GLa) on the tomographic image GL is designated, the designated positional information (GLa') is displayed on the fundus image Ef' at a position corresponding to the designated position, and therefore, the examiner may easily capture the relation of the position on the fundus image Ef' and the position on the tomographic image GL.

[Operational Feature 3]

Figure 24:
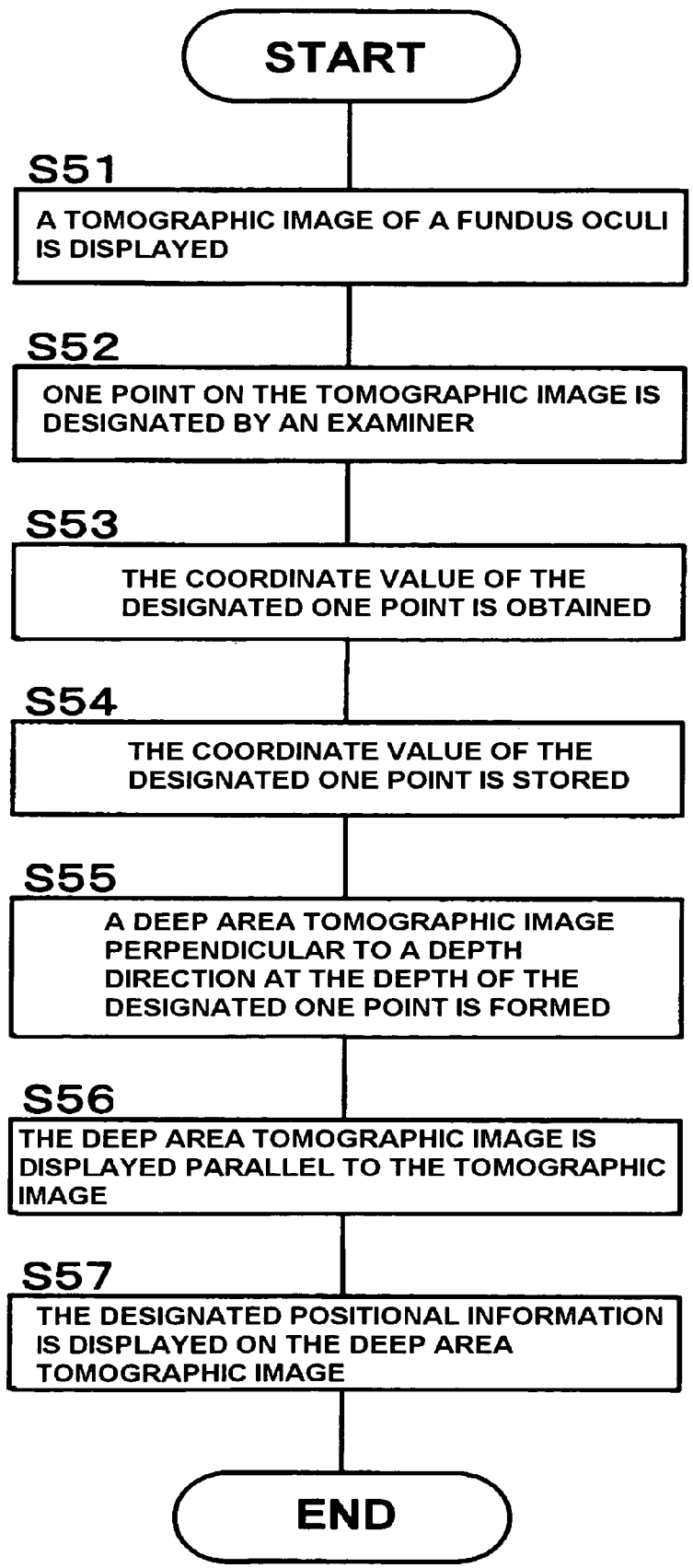
FIG. 24 is a flow chart representing one operational example in a favorable embodiment of the fundus observation device related to the present invention.

Next, the third operational feature of the fundus observation device 1000 is described referring to the flow chart shown in FIG. 24. In this operational feature, one example of the operations of the fundus observation device 1000 is explained in the case when the examiner designates a position deeper than the fundus surface of a tomographic image, while a tomographic image of (at least) a fundus oculi Ef is displayed on the display 207 (S51).

Figure 25:
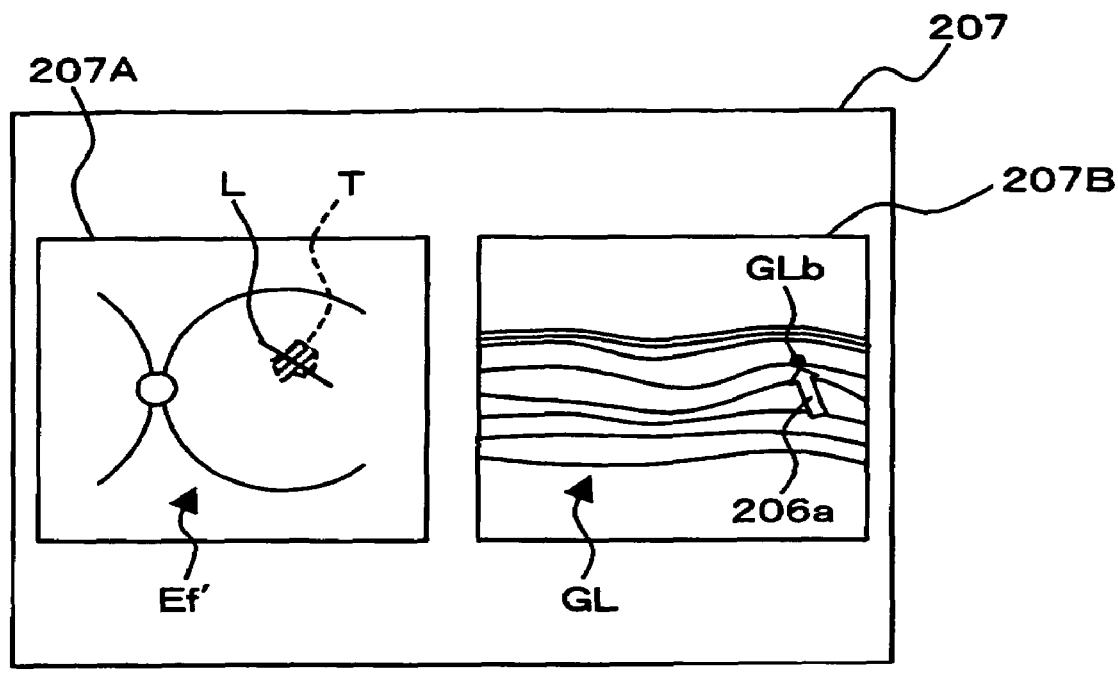
FIG. 25 is a schematic diagram representing one example of the display features of a fundus image in a favorable embodiment of the fundus observation device related to the present invention.

FIG. 25 represents one example of the display features of a tomographic image GL (and a fundus image Ef). As shown in the drawing, by operating the mouse 206 with the mouse pointer 206a to point to one point GLb on an image region equivalent of the deep area of a fundus oculi in the tomographic image GL, the examiner designates the one point GLb (S52). The information indicating the position of the designated one point GLb (coordinate value) is sent to the controlling part 210 from the user interface 230.

The coordinate value of the one point GLb on the tomographic image GL is represented by a coordinate value ($\xi c$, $\eta c$) in the $\xi\eta$ coordinate system.

The controlling part 210 converts the coordinate value ($\xi c, \eta c$) of the one point GLb to obtain a coordinate value (xc,yc,zc) of the one point GLb in the xyz coordinate system defined in the tomographic image GL (3-dimensional image G) (S53). The controlling part 210 stores the coordinate value (xc,yc,zc) of this one point in the designated position storing part 240.

Furthermore, the controlling part 210 sends the z coordinate value zc of this coordinate value (xc,yc,zc) to an image processing part 220. Once this z coordinate value zc is received, based on an image data (ref. Embodiment 1) of the 3-dimensional image of a fundus oculi Ef, the image processing part 220 forms image data of the tomographic image (deep area tomographic image) at a cross-sectional position of z=zc (S55). This deep area tomographic image GD is a 2-dimensional image parallel to the xy coordinate plane; in other words, a 2-dimensional image perpendicular to a z-direction (depth direction), and at the same time, the coordinate value (xc,yc,zc) of the one point GLb is included therein.

Figure 26:
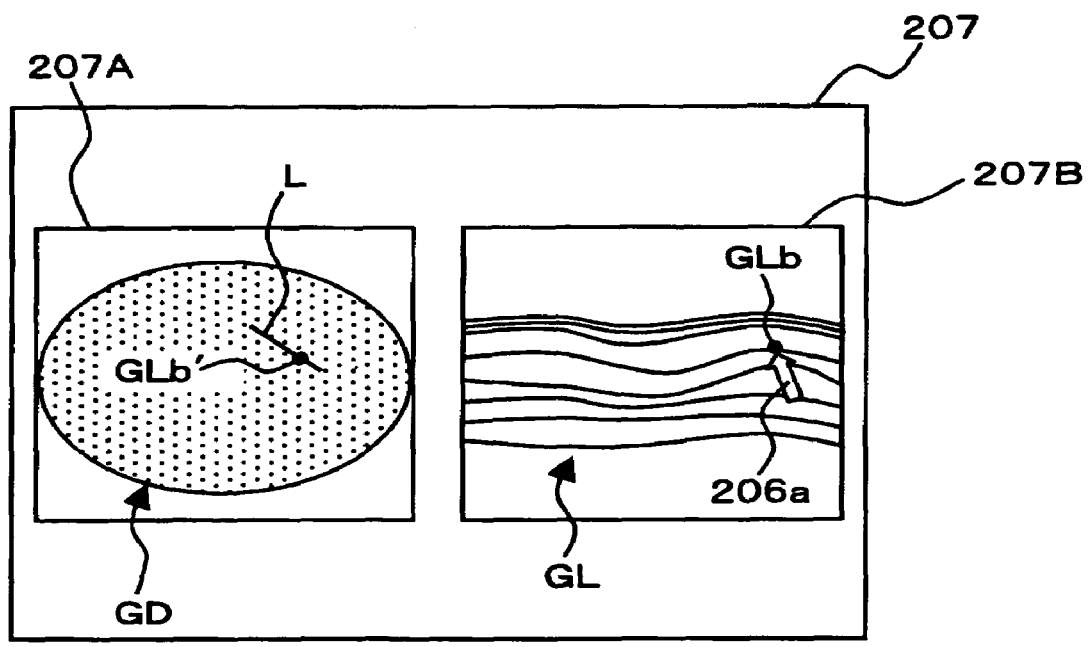
FIG. 26 is a schematic diagram representing one example of the display features of a fundus image in a favorable embodiment of the fundus observation device related to the present invention.

Furthermore, the controlling part 210 displays the deep area tomographic image GD formed in step S55 in the fundus image display region 207A (as a result, to be displayed parallel to the tomographic image GL), and at the same time, displays the designated positional information GLb' indicating a position on the deep area tomographic image GD, that corresponds to the coordinate value (xc,yc,zc) obtained in step S53, so as to be overlapped with this deep area tomographic image GD (S57). Then, based on the association of the xyz coordinate system explained in Embodiment 1 and the $\xi\eta$ coordinate system, the controlling part 210 converts the coordinate value (xc,yc,zc) to the $\xi\eta$ coordinate system (the $\xi\eta$ coordinate system defined in the fundus image display region 207A), and displays the designated positional information GLb' on the deep area tomographic image GD at a position to be specified by a coordinate value ($\xi c', \eta c'$) that has been obtained accordingly. FIG. 26 represents one example of the display features of the designated positional information GLb' obtained as described. Moreover, as shown in FIG. 26, it is preferable to display the attention line L indicating the tomographic position of a tomographic image GL in the deep area tomographic image GD.

Furthermore, the information (coordinate value (xc,yc,zc)) indicating the designated position (one point GLb) stored in the designated position storing part 240 in step S54 is read-out later when the image is observed, and the designated positional information (GLb') is displayed on the deep area tomographic image GD. Moreover, in the event of displaying a fundus image Ef, the designated positional information may be displayed on the fundus image Ef at a position to be specified by the coordinate value (xc,yc) that has been obtained by projecting the coordinate value (xc,yc,zc) on the xy coordinate plane.

In the operational feature described above, the designated positional information is displayed only on the deep area tomographic image GD; however it may also be configured to display the designated positional information at a designated position (position of one point GLb) on the tomographic image GL.

Furthermore, in the operational feature described above, after moving the mouse pointer 206a to a desired position on the tomographic image GL by clicking, the designated position is confirmed (ref. step S52); however, for example, it may also be configured to execute the formation process as well as the display process of a deep area tomographic image, and the display process of designated positional information following the movement of the mouse pointer 206a on the tomographic image GL.

According to the present operational feature, once the position (one point GLb) on the tomographic image GL is designated, a 2-dimensional image (deep area tomographic image) perpendicular to the z-direction, whose cross-sectional position is the depth of the designated position, is formed and displayed parallel to the tomographic image GL, and at the same time, the designated positional information (GLb') is displayed on the deep area tomographic image at a position corresponding to the designated position on the cross-sectional position, and therefore, the examiner can easily capture the relation of the position on the tomographic image GL and the position on the deep area tomographic image.

[Operational Feature 4]

Figure 27:
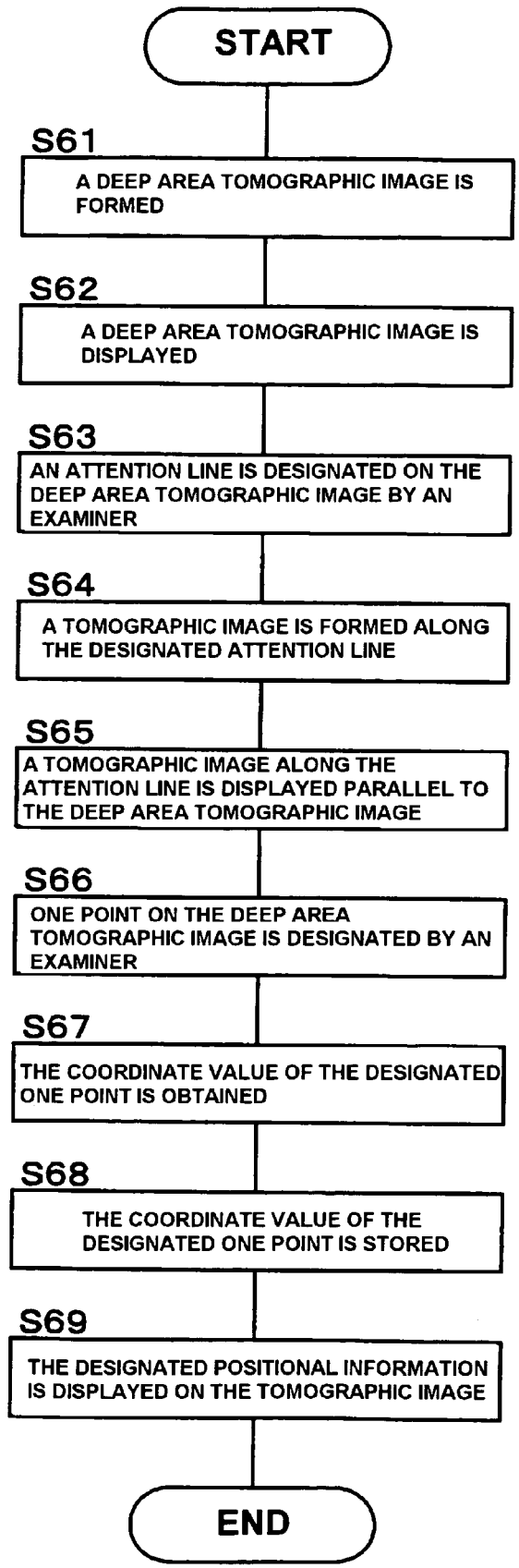
FIG. 27 is a flow chart representing one operational example in a favorable embodiment of the fundus observation device related to the present invention.

Next, the fourth operational feature of the fundus observation device 1000 is described referring to the flow chart shown in FIG. 27.

First, based on the image data of the 3-dimensional image of a fundus oculi Ef that has been described in Embodiment 1, the image processing part 220 forms image data for a tomographic image (deep area tomographic image) GD perpendicular to the depth direction at a given depth (z coordinate value z=zd) of a fundus oculi Ef (S61). The depth z=zd of this deep area tomographic image GD is, for example, to be designated by an examiner. Based on the formed image data, the controlling part 210 displays this deep area tomographic image GD on the display 207 (S62).

Figure 28:
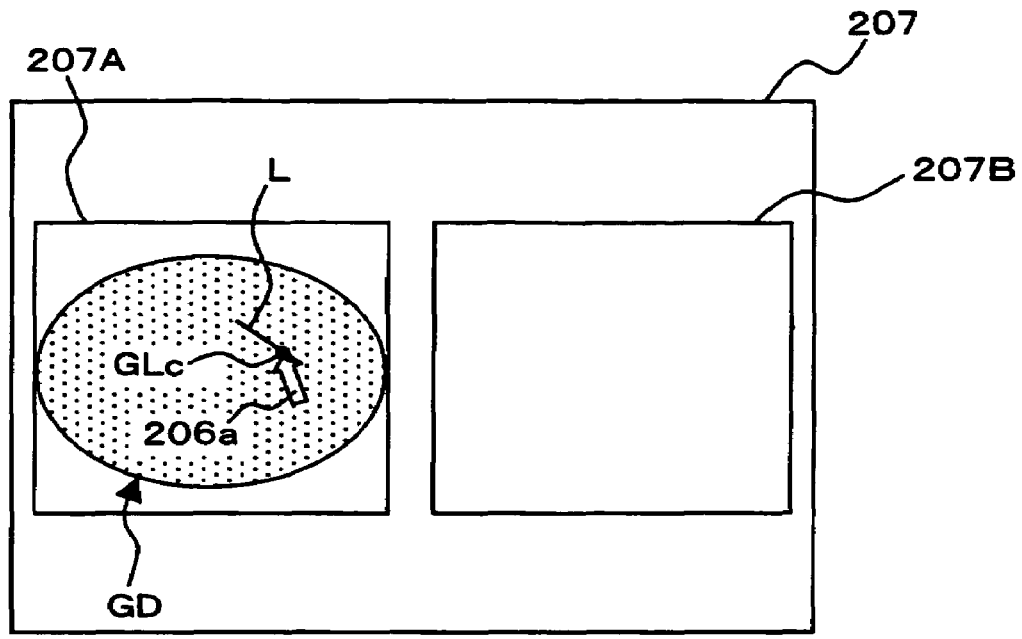
FIG. 28 is a schematic diagram representing one example of the display features of a fundus image in a favorable embodiment of the fundus observation device related to the present invention.

FIG. 28 represents one example of the display features of a deep area tomographic image GD. In the figure, the deep area tomographic image GD is displayed in the fundus image display region 207A of the display 207. By operating the mouse 206, the examiner designates the attention line L (ref. FIG. 28) on the deep area tomographic image GD (S63).

Figure 29:
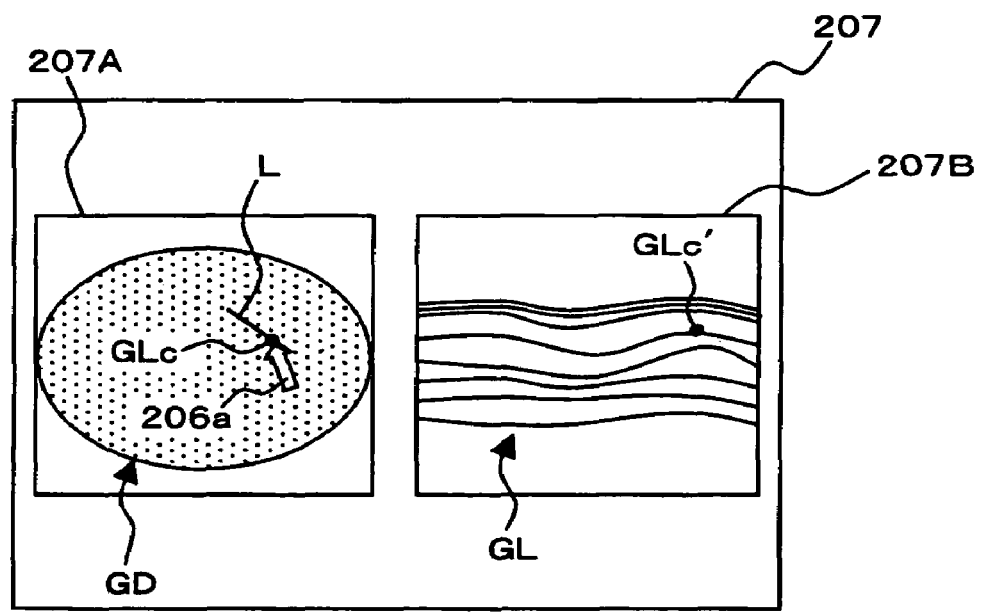
FIG. 29 is a schematic diagram representing one example of the display features of a fundus image in a favorable embodiment of the fundus observation device related to the present invention.

The controlling part 210 performs the same process as in Embodiment 1 to obtain the coordinate value of the designated attention line L to be sent to the image processing part 220. The image processing part 220 forms image data of the tomographic image GL (a tomographic image having a cross-section in the depth direction) along with this attention line (S64). As shown in FIG. 29, the controlling part 210 displays this tomographic image GL in the tomographic image display region 207B (S65). As a result, on the display 207, the deep area tomographic image GD and the tomographic image GL are displayed in parallel.

Further, as shown in FIG. 28, by moving the mouse pointer 206a to one point GLc on the deep area tomographic image GD and clicking, the examiner designates the one point GLc (S66). The controlling part 210 receives a coordinate value ($\xi c, \eta c$) indicating the position of the designated one point GLc, and converts this to obtain (xd,yd,zd) in the xyz coordinate system (S67), and at the same time, stores this coordinate value (xd,yd,zd) in the designated position storing part 240.

Furthermore, the controlling part 210 displays a designated positional information GLc' indicating a position on the tomographic image GL that corresponds to the coordinate value (xd,yd,zd) that was obtained in step S67, so as to be overlapped with this tomographic image GL (S69). Then, based on the association of the xyz coordinate system explained in Embodiment 1 and the ξη coordinate system, the controlling part 210 converts the coordinate value (xd,yd,zd) to the ξη coordinate system (the ξη coordinate system defined in the tomographic image display region 207B), and displays the designated positional information GLc' on the tomographic image GL at a position to be specified by a coordinate value (ξc',ηc') that has been obtained accordingly. The FIG. 29 represents one example of the display features of a designated positional information GLc' obtained as described.

Furthermore, the information (coordinate value (xd,yd, zd)) indicating the designated position (one point GLc) stored in the designated position storing part 240 in step S68 is read-out later when the image is observed and the designated positional information (GLc') is displayed on the tomographic image GL.

In the operational feature described above, the designated positional information is displayed only on the tomographic image GL; however, for example, it may also be configured to display the designated positional information at a designated position (position of one point GLc) on the deep area tomographic image GD.

Furthermore, in the present operational feature described above, after moving the mouse pointer 206a to a desired position on the deep area tomographic image GD by clicking, the designated position is confirmed (ref. step S66); however, for example, it may also be configured to execute the formation process as well as the display process of the tomographic image, and the display process of the designated positional information following the movement of the mouse pointer 206a on the deep area tomographic image GL.

Moreover, in the present operational feature, responding to the examiner having specifically input an attention line L on the deep area tomographic image GD, a tomographic image GL, whose cross-sectional position is the attention line, is formed and displayed; however, the present invention is not limited to this configuration. For example, responding to the examiner having designated one point GLc on the deep area tomographic image GD, it may also be configured to set up the attention line L passing this one point GLc appropriately, so as to form a tomographic image GL, whose cross-sectional position is this attention line L that has been automatically set. The automatic setting process of this attention line L may be configured, for example, so as to read-out the saved information regarding the direction or the size (length) of the attention line L used in the past examinations so as to be set up automatically. Furthermore, it is also possible to configure in a manner such that the direction (for example, x-direction, y-direction, etc.) and the size of the attention line L is preset, and the attention line L is also set automatically so as to arrange the designated one point GLc, for example, in the mid. point.

According to the present operational feature, once the position (one point GLc) on the deep area tomographic image GD is designated, a tomographic image GL having a cross-sectional position including the designated position is formed and displayed parallel to the deep area tomographic image GD, and at the same time, the designated positional information (GLc') is displayed on the tomographic image at a position corresponding to the designated position, and therefore, the examiner can easily capture the relation of the position on the deep area tomographic image and the position on the tomographic image GL.

[Operational Feature 5]

Figure 30:
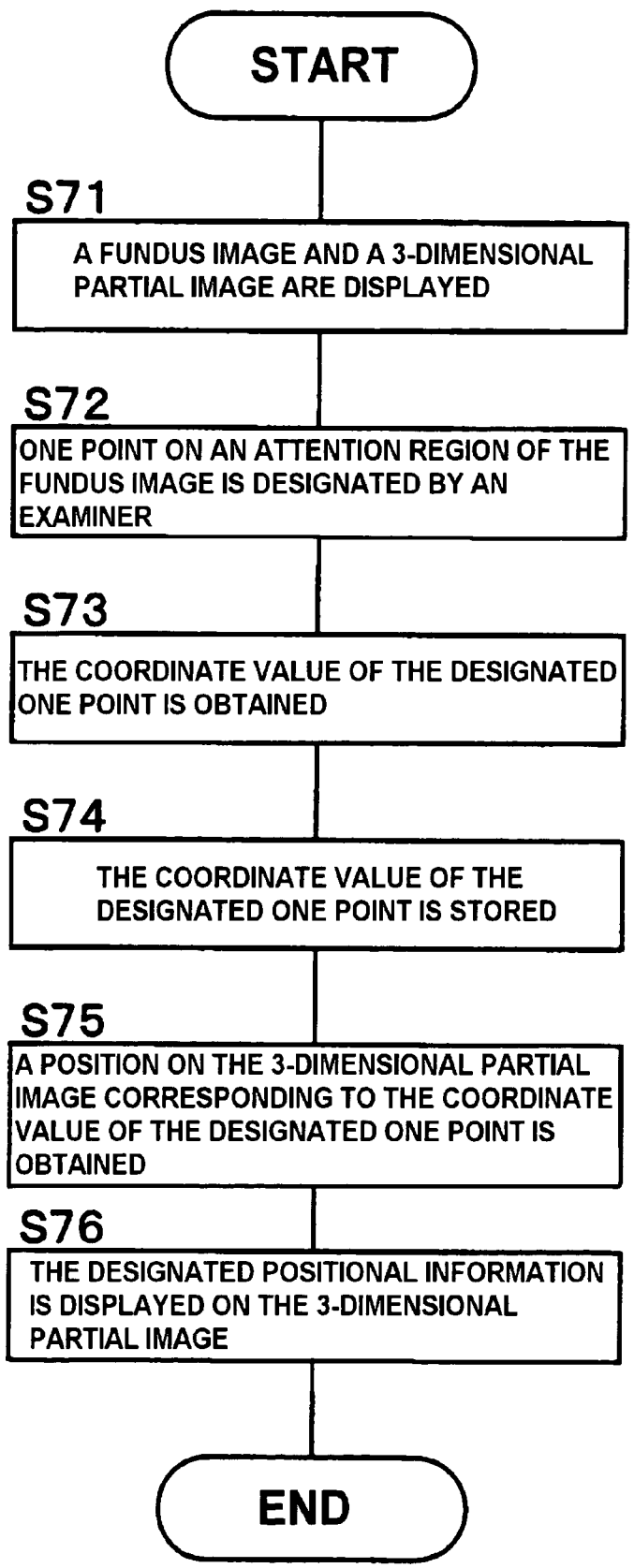
FIG. 30 is a flow chart representing one operational example in a favorable embodiment of the fundus observation device related to the present invention.

Next, the fifth operational feature of the fundus observation device 1000 is described referring to the flow chart shown in FIG. 30. With this operational feature, one example of operations of the fundus observation device 1000 is explained for the case when the examiner designates one point on a 2-dimensional image while a 2-dimensional image (fundus image) of a fundus surface and a 3-dimensional (partial) image of the fundus are displayed in parallel on the display 207 (S71).

Figure 31:
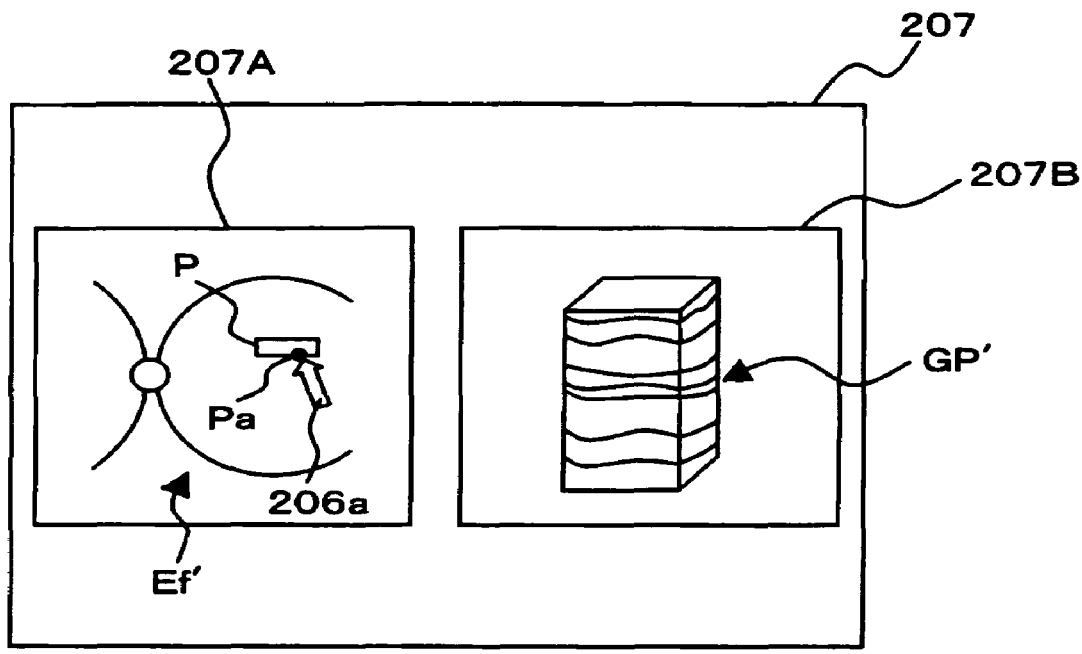
FIG. 31 is a schematic diagram representing one example of the display features of a fundus image in a favorable embodiment of the fundus observation device related to the present invention.

FIG. 31 represents one example of the display features of a 2-dimensional image (fundus image Ef') and a 3-dimensional image of the surface of a fundus oculi Ef. These images, for example, are displayed on the display 207 in accordance with the procedure that was explained in Embodiment 1 (ref. FIG. 16).

As shown in FIG. 31, by operating the mouse 206 with the mouse pointer 206a to point to one point (area requiring a particular attention) on an attention region P and clicking, the one point Pa is designated (S72). A coordinate value (ξd,ηd) indicating the position of the designated one point Pa is sent to the controlling part 210 from the user interface 230.

The controlling part 210 converts the coordinate value (ξd,ηd) of the one point Pa to obtain a coordinate value (xe,ye) of the one point LPa in the xy coordinate system defined in the fundus image Ef' (the image data thereof) (S73). Then, the controlling part 210 stores the coordinate value (xe,ye) of this one point Pa in the designated position storing part 240 (S74). Then, arithmetic may be performed to store the z coordinate value ze of the one point Pa (z coordinate value equivalent of the surface of the fundus oculi Ef).

Furthermore, the controlling part 210 obtains a position on a 3-dimensional partial image GP' that corresponds to the coordinate value (xe,ye) of the one point Pa that was obtained in step S73. For this, for example, a straight line {(xe,ye,z): z=any} that passes through the coordinate value (xe,ye) and yet extends in the z-direction (depth direction) is obtained (this straight line becomes a position on the 3-dimensional partial image GP', that corresponds to the coordinate value (xe,ye)).

Figure 32:
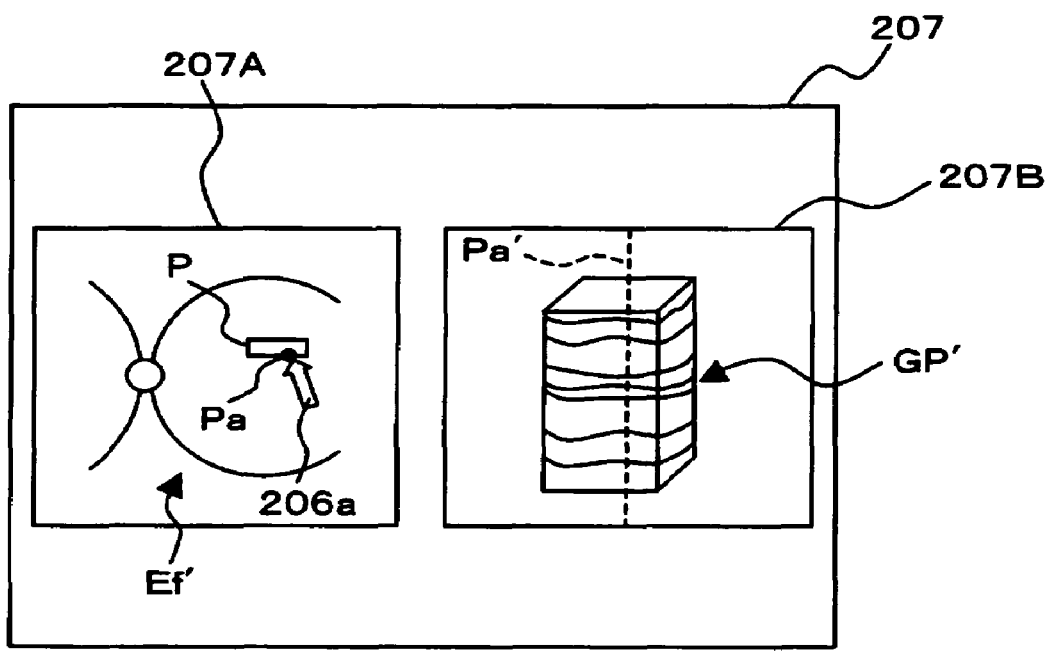
FIG. 32 is a schematic diagram representing one example of the display features of a fundus image in a favorable embodiment of the fundus observation device related to the present invention.

Furthermore, the controlling part 210 displays a designated positional information indicating a position on the 3-dimensional image GP', that corresponds to the one point Pa that was obtained in step S75, so as to be overlapped with the 3-dimensional partial image GP' displayed in the tomographic image display region 207B (S76). Then, based on the association of the xyz coordinate system explained in Embodiment 1 and the ξη coordinate system, the controlling part 210 converts the straight line {(xe,ye,z):z=any} obtained in step S75 to the ξη coordinate system (the ξη coordinate system defined in the tomographic image display region 207B) and displays a designated positional information Pa' along the straight line that has been obtained accordingly. FIG. 32 represents one example of the display features of the designated positional information Pa' obtained as described.

Furthermore, the information (coordinate value) indicating the designated position (one point Pa) stored in the designated position storing part 240 in step S74 is read-out by the controlling part 210 later when the image is observed (e.g. when comparing with past images in a follow-up observation), and the designated positional information (Pa') is displayed on the 3-dimensional partial image GP'.

In the present operational feature, the designated positional information is displayed only on the 3-dimensional partial image GP'; however, it may as well be configured to display the designated positional information also on a fundus image Ef'. For example, in step S72, when one point Pa on the fundus image Ef' is designated, the designated positional information may be displayed at this one point Pa.

Moreover, in the present operational feature, after moving the mouse pointer 206a to a desired position on the fundus image Ef' by clicking, the designated position is confirmed (ref. step S72); however, for example, it may also be configured to display the designated positional information on the 3-dimensional partial image GP' following the movement of the mouse pointer 206a on the fundus image Ef'.

Furthermore, in the present operational feature, the display process of the designated positional information has been explained for the case when the 3-dimensional partial image GP' is displayed on the display 207; however, the same process may be performed for the case when a 3-dimensional image G that was the base of this 3-dimensional partial image GP' is displayed.

Also, the designating position as one point Pa may be a contour region of an attention region P, or an internal region. Moreover, the designated positional information Pa' may consist of only a straight line as in the present operational feature, or may include other information (for example, an image, etc. representing a position where the straight line crosses with a surface (and the bottom) plane of the 3-dimensional partial image GP').

According to the present operational feature, with respect to the fundus image Ef' and the 3-dimensional partial image GP' displayed in parallel, once the position (one point Pa) on the fundus image Ef' is designated, the designated positional information (Pa') is displayed on the 3-dimensional partial image GP' at a position corresponding to the designated position, and therefore, the examiner may easily capture the relation of the position on the fundus image Ef' and the position on the 3-dimensional partial image GP'.

[Operational Feature 6]

Figure 33:
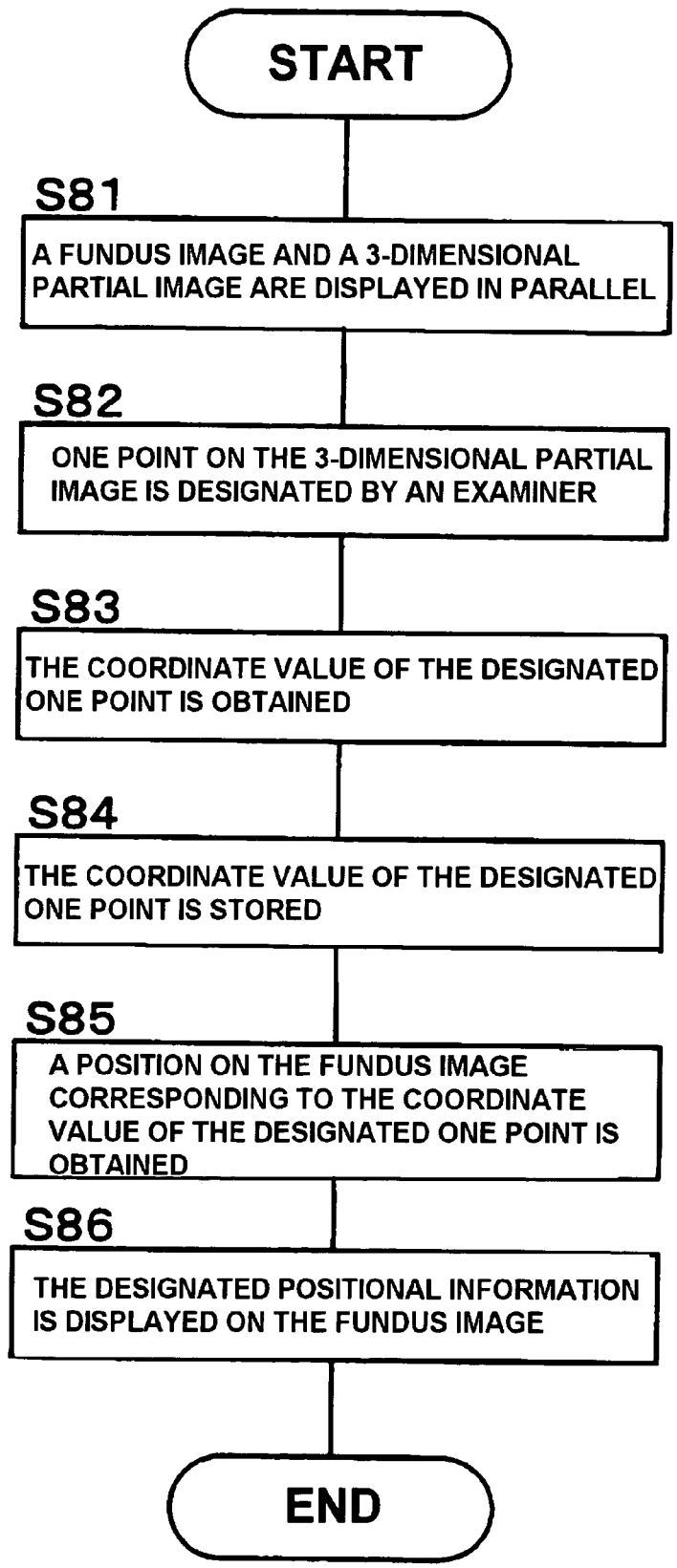
FIG. 33 is a flow chart representing one operational example in a favorable embodiment of the fundus observation device related to the present invention.

Next, the sixth operational feature of the fundus observation device 1000 is described referring to the flow chart shown in FIG. 33. With this operational feature, one example of the operations of the fundus observation device 1000 is explained for the case when the examiner designates one point on a 3-dimensional partial image GP' while a 2-dimensional image (fundus image) and a 3-dimensional partial image of a fundus surface are displayed in parallel on the display 207 (S81).

Figure 34:
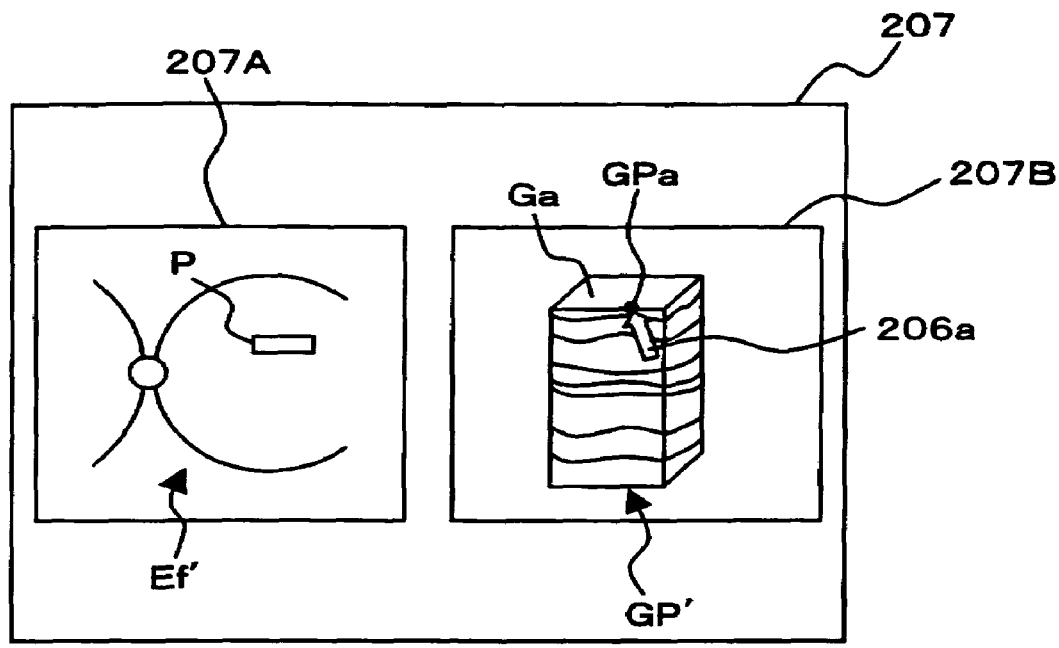
FIG. 34 is a schematic diagram representing one example of the display features of a fundus image in a favorable embodiment of the fundus observation device related to the present invention.

FIG. 34 represents one example of the display features of a fundus image Ef' and a 3-dimensional partial image GP'. These images, for example, are displayed on the display 207 in accordance with the procedure that was explained in Embodiment 1 (ref. FIG. 16).

As shown in FIG. 34, by operating the mouse 206 with the mouse pointer 206a to point to one point on an image region Ga that is an equivalent of a fundus surface in the 3-dimensional partial image GP' and clicking, the one point GPa is designated (S82). The coordinate value ($\xi e, \eta e$) indicating the position of the designated one point GPa is sent to the controlling part 210 from the user interface 230.

The controlling part 210 converts the coordinate value ($\xi d, \eta d$) of the one point GPa to obtain a coordinate value (xf,yf,zf) in the xyz coordinate system (S83). Then, the controlling part 210 stores the coordinate value (xf,yf,zf) of this one point GPa in the designated position storing part 240 (S84).

Furthermore, the controlling part 210 obtains a position on a fundus image Ef' that corresponds to the coordinate value (xf,yf,zf) of the one point GPa that was obtained in step S83. For this process, for example, the coordinate value (xf,yf) is obtained by projecting the coordinate value (Xf,yf,zf) of the one point GPa onto an xy coordinate plane (this coordinate value becomes a position on the fundus image corresponding to the coordinate value (xf,yf,zf) of the one point GPa.

Figure 35:
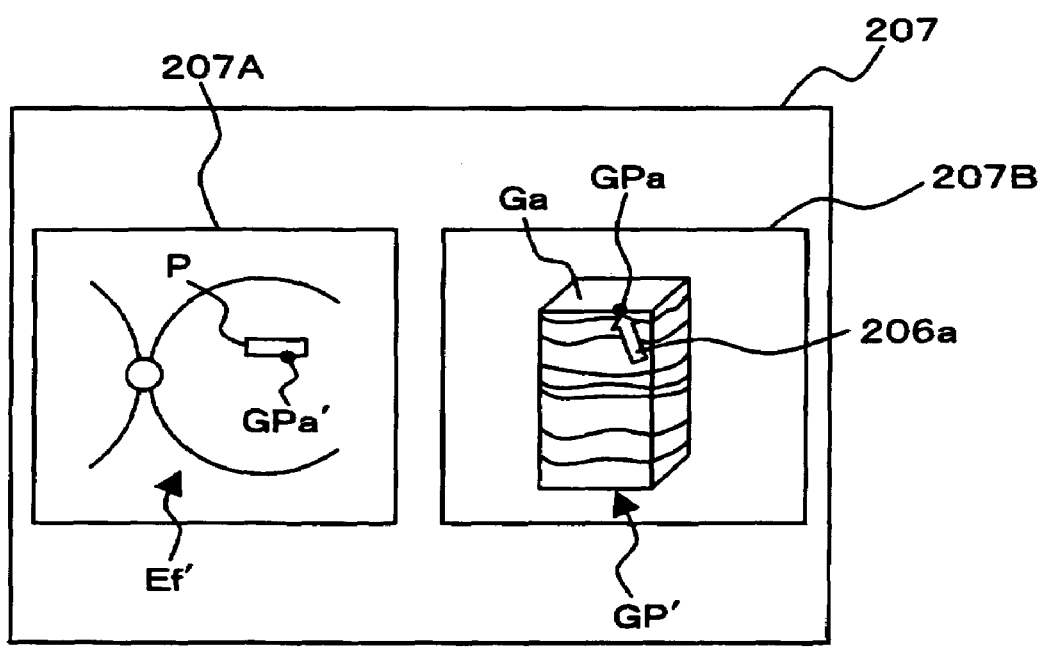
FIG. 35 is a schematic diagram representing one example of the display features of a fundus image in a favorable embodiment of the fundus observation device related to the present invention.

Furthermore, the controlling part 210 displays a designated positional information GPa' indicating a position on the fundus image Ef' that corresponds to the one point GPa that was obtained in step S85, so as to be overlapped with the fundus image Ef' displayed in the fundus image display region 207A (S86). Then, based on the association of the xyz coordinate system explained in Embodiment 1 and the $\xi\eta$ coordinate system, the controlling part 210 converts the coordinate value (xf,yf) that was obtained in step S85 to the $\xi\eta$ coordinate system (the $\xi\eta$ coordinate system defined in the fundus image display region 207A) and displays the designated positional information GPa' on the fundus image Ef' at a position to be specified by a coordinate value ($\xi f', \eta f'$) that has been obtained accordingly. FIG. 35 represents one example of the display features of the designated positional information GPa' obtained as described.

Furthermore, the information (coordinate value) indicating the designated position (one point GPa) stored in the designated position storing part 240 in step S84 is read-out later when the image is observed, and the designated positional information (GPa') is displayed on the fundus image Ef'.

In the present operational feature, the designated positional information is displayed only on the fundus image Ef'; however, it may also be configured to display the designated positional information on the 3-dimensional partial image GP' (position of the one point GPa).

Moreover, in the present operational feature, after moving the mouse pointer 206a to a desired position on a 3-dimensional partial image GP' by clicking, the designated position is confirmed (ref. step S82); however, for example, it may also be configured to display the designated positional information on the fundus image Ef' following the movement of the mouse pointer 206a on the 3-dimensional partial image GP'.

Furthermore, with regard to the present operational feature, although the process to be executed for the case when one point on an image region Ga that is an equivalent of a fundus surface in the 3-dimensional partial image GP' has been explained, the same process may be performed for the case when a position (one point) deeper than the fundus surface is designated. For example, by presetting the $\eta$ coordinate value $\eta 0$ of a position equivalent of a fundus surface, and when a position equivalent of a depth of the fundus oculi of the 3-dimensional partial image GP' is designated, by performing the process described above with respect to the ($\xi b, \eta 0$) that is obtained from converting the $\eta$ coordinate value $\eta b$ of the coordinate value ($\xi f, \eta f$) of the designated position to $\eta 0$, the same result may be obtained.

Furthermore, in the present operational feature, the display process of the designated positional information has been explained for the case when the 3-dimensional partial image GP' is displayed on the display 207; however, the same process may be performed for the case when a 3-dimensional image G that is the base of this 3-dimensional partial image GP' is displayed.

Also, the designated position as one point GPa may be a contour region of the 3-dimensional partial image GP', or be an internal region.

According to the present operational feature, with respect to the fundus image Ef' and the 3-dimensional partial image GP' to be displayed in parallel, once the position (one point GPa) on the 3-dimensional partial image GP' is designated, the designated positional information (GPa') is displayed on the fundus image Ef' at a position corresponding to the designated position, and therefore, the examiner may easily capture the relation of the position on the fundus image Ef' and the position on the 3-dimensional partial image GP'.

[Operational Feature 7]

Figure 36:
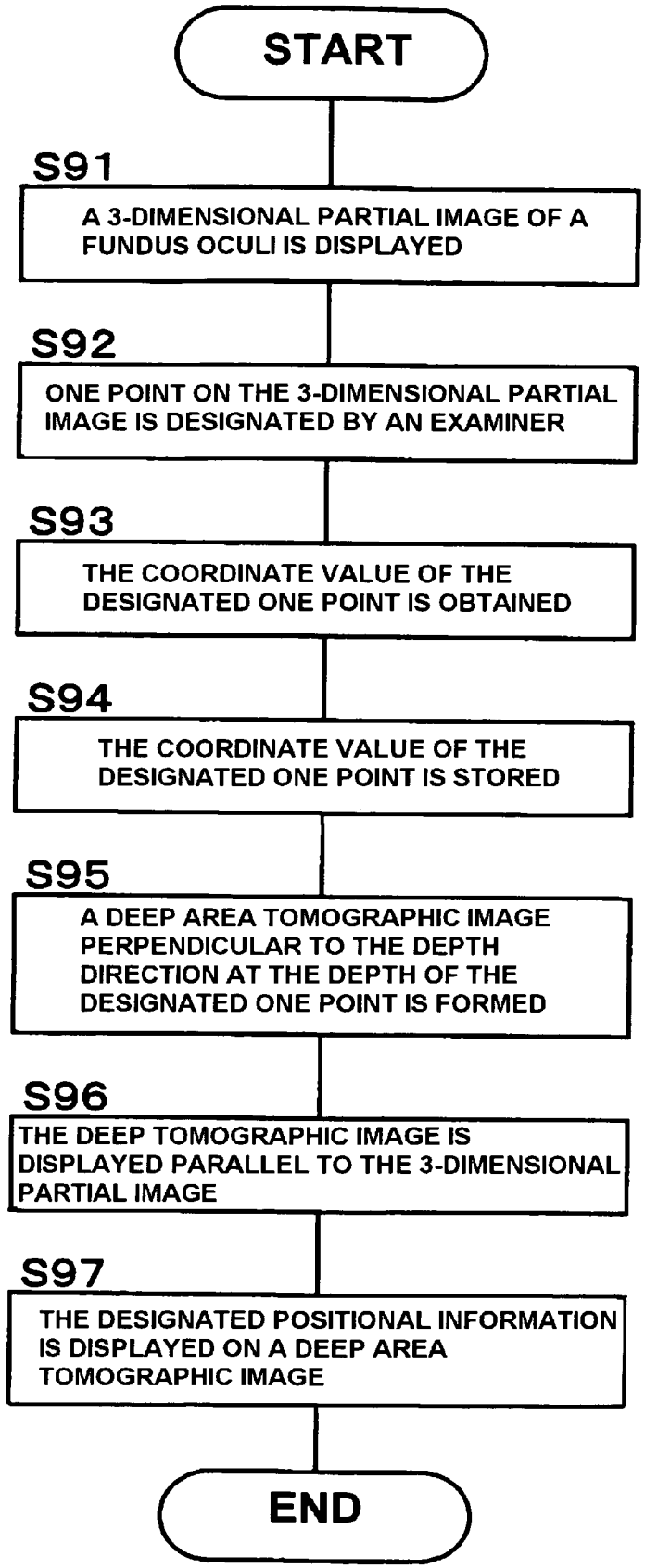
FIG. 36 is a flow chart representing one operational example in a favorable embodiment of the fundus observation device related to the present invention.

Next, the seventh operational feature of the fundus observation device 1000 is described referring to the flow chart shown in FIG. 36. In this operational feature, one example of the operations of the fundus observation device 1000 is explained for the case when the examiner designates a position deeper than the fundus surface of a 3-dimensional partial image GP' while (at least) a 3-dimensional partial image GP' of a fundus oculi Ef is displayed on the display 207 (S91).

Figure 37:
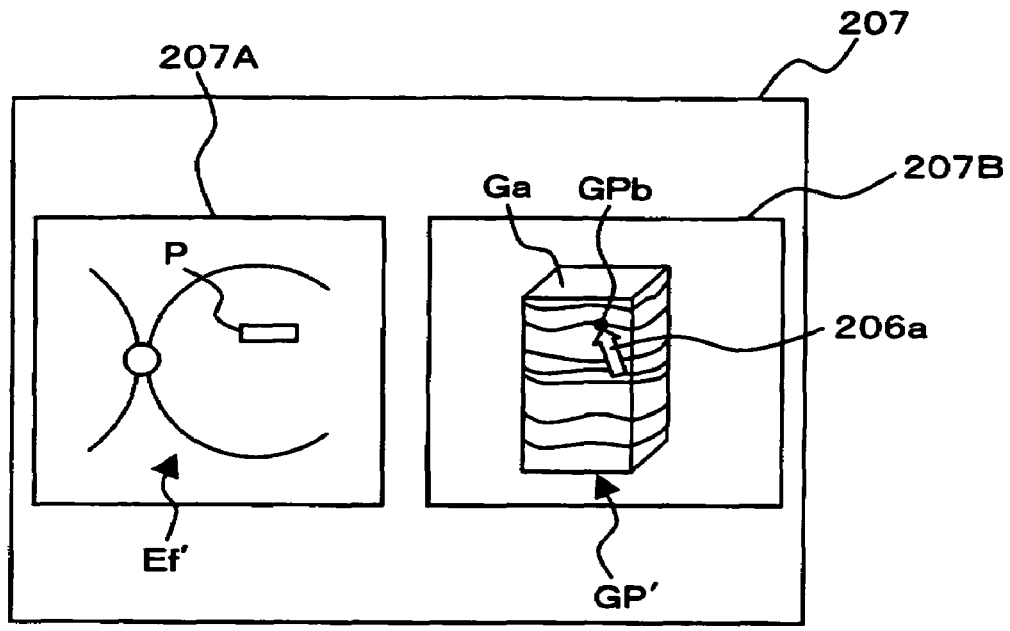
FIG. 37 is a schematic diagram representing one example of the display features of a fundus image in a favorable embodiment of the fundus observation device related to the present invention.

FIG. 37 shows one example of the display features of a 3-dimensional partial image GP' (and a fundus image Ef'). As shown in the figure, by operating the mouse 206 with the mouse pointer 206a to point to one point on an image region GPb (one point GPb located deeper than a fundus surface Ga) that is an equivalent of the deep area of a fundus oculi in the 3-dimensional partial image GP' and clicking, the one point GPb is designated (S92). The coordinate value ($\xi$f,$\eta$f) indicating the position of the designated one point GPb is sent to the controlling part 210 from the user interface 230.

The controlling part 210 converts a coordinate value ($\xi$f, $\eta$f) of the one point GPb to obtain a coordinate value (xg,yg, zg) of the one point in the xyz coordinate system defined in the 3-dimensional partial image GP' (S93). Then, the controlling part 210 stores the coordinate value (xg,yg,zg) of this one point GPb in the designated position storing part 240 (S94).

Furthermore, the controlling part 210 sends the z coordinate value zg of this coordinate value (xg,yg,zg) to the image processing part 220. Upon receipt of this z coordinate value zc, based on the image data (ref. Embodiment 1) of the 3-dimensional image G of a fundus oculi Ef, the image processing part 220 forms the image data of the tomographic image (deep area tomographic image) GE at a cross-sectional position of z=zg (S95). This deep area tomographic image GE is a 2-dimensional image parallel to the xy coordinate plane; that is, a 2-dimensional image perpendicular to the z-direction (depth direction) also including the coordinate value (xg,yg,zg) of the one point GPb.

Figure 38:
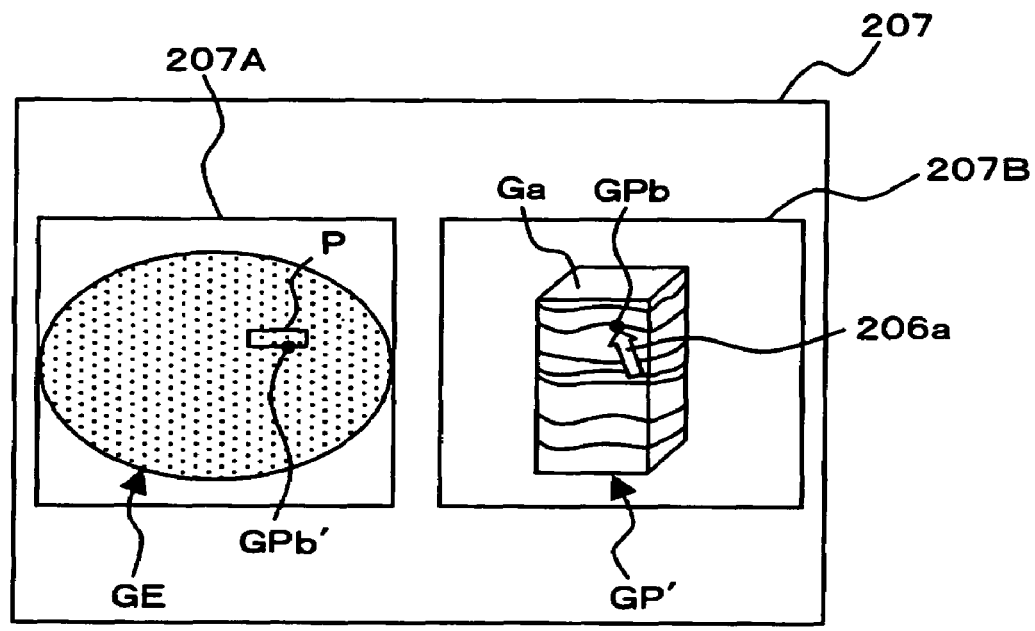
FIG. 38 is a schematic diagram representing one example of the display features of a fundus image in a favorable embodiment of the fundus observation device related to the present invention.

Furthermore, the controlling part 210 displays the deep area tomographic image GE formed in step S95 in the fundus image display region 207A (as a result, to be displayed parallel to the 3-dimensional partial image GP') (S96), and at the same time, displays the designated positional information GPb' indicating the position on the deep area tomographic image GE that corresponds to the coordinate value (xg,yg,zg) that was obtained in step S93, so as to be overlapped with this deep area tomographic image GE (S97). Then, based on the association of the xyz coordinate system explained in Embodiment 1 and the $\xi\eta$ coordinate system, the controlling part 210 converts the coordinate value (xg,yg,zg) to the $\xi\eta$ coordinate system (the $\xi\eta$ coordinate system defined in the fundus image display region 207A) and displays the designated positional information GPb' on the deep area tomographic image GE at a position to be specified by a coordinate value ($\xi$g',$\eta$g') that has been obtained accordingly. FIG. 38 represents one example of the display features of the designated positional information GPb' obtained as described. Moreover, as shown in this FIG. 38, it is preferable to display an attention region P that corresponds to the 3-dimensional partial image GP' in the deep area tomographic image GE.

Furthermore, the information ((coordinate value) xg,yg, zg) indicating the designated position (one point GPb) stored in the designated position storing part 240 in step S94 is read-out later when the image is observed, and the designated positional information (GLPb') is displayed on the deep area tomographic image GE'.

In the present operational feature described above, the designated positional information is displayed only on the deep area tomographic image GE; however, it may also be configured so as to display the designated positional information at a designated position (position of one point GPb) on the 3-dimensional partial image GP'.

Moreover, in the present operational feature, after moving the mouse pointer 206a to a desired position on the 3-dimensional partial image GP' by clicking, the designated position is confirmed (ref. step S92); however, for example, it may also be configured to execute the formation process as well as the display process of the deep area tomographic image, and the display process of the designated positional information following the movement of the mouse pointer 206a on the 3-dimensional partial image GP'.

Furthermore, in the present operational feature, the display process of the designated positional information has been explained for the case when the 3-dimensional partial image GP' is displayed on the display 207; however, the same process may be performed for the case when the 3-dimensional image G that was the base of this 3-dimensional partial image GP' is displayed.

Also, the designated position as one point GPb may be a contour region of the 3-dimensional partial image GP', or an internal region.

According to the present operational feature, once the position (one point GPb) on the 3-dimensional partial image GP' is designated, a 2-dimensional image (deep area tomographic image) perpendicular to direction z, whose cross-sectional position is the depth of the designated position, is to be formed and displayed parallel to the 3-dimensional partial image GP', and at the same time the designated positional information (GPb') is displayed on the deep area tomographic image at a position corresponding to the designated position, and therefore, the examiner may easily capture the relation of the position on the 3-dimensional partial image GP' and the position on the deep area tomographic image.

[Operational Feature 8]

Figure 39:
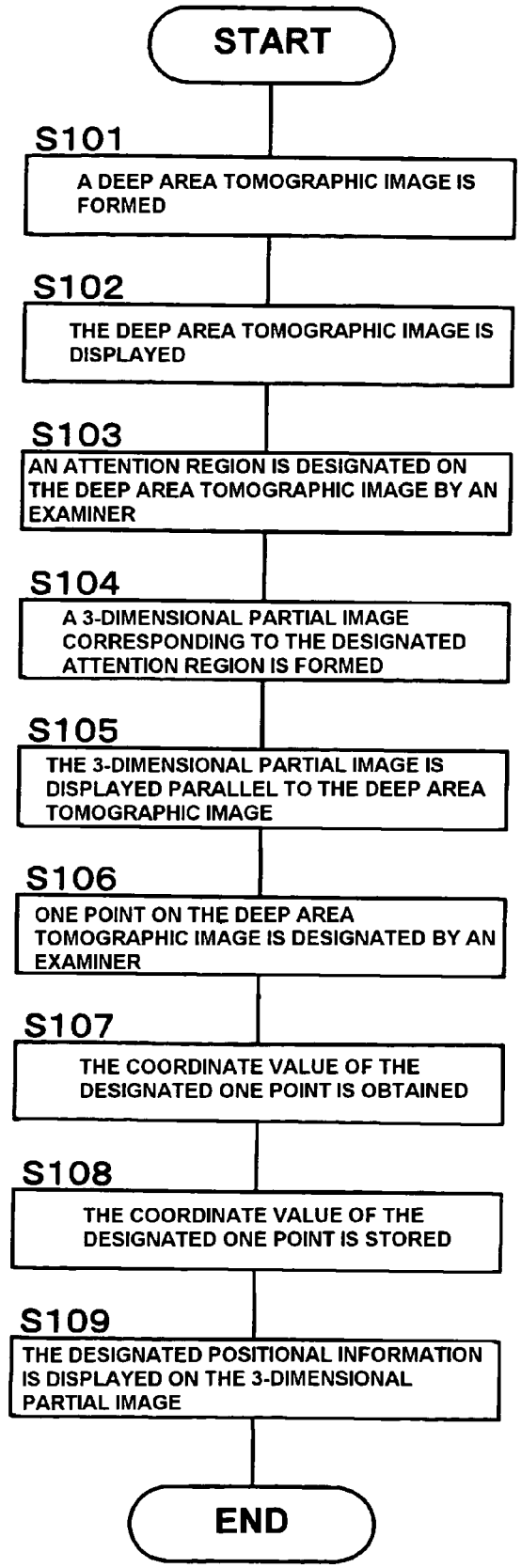
FIG. 39 is a flow chart representing one operational example in a favorable embodiment of the fundus observation device related to the present invention.

Next, the eighth operational feature of the fundus observation device 1000 is described referring to the flow chart shown in FIG. 39.

First, based on the image data of the 3-dimensional image G of the fundus oculi Ef explained in Embodiment 1, the image processing part 220 forms the image data of a tomographic image (deep area tomographic image) GE perpendicular to the depth direction at a given depth (z coordinate value z=zh) of a fundus oculi Ef (S101). The depth z=zh of this deep area tomographic image GE is designated, for example, by an examiner. Based on the formed image data, the controlling part 210 displays this deep area tomographic image GE on the display 207 (S102).

Figure 40:
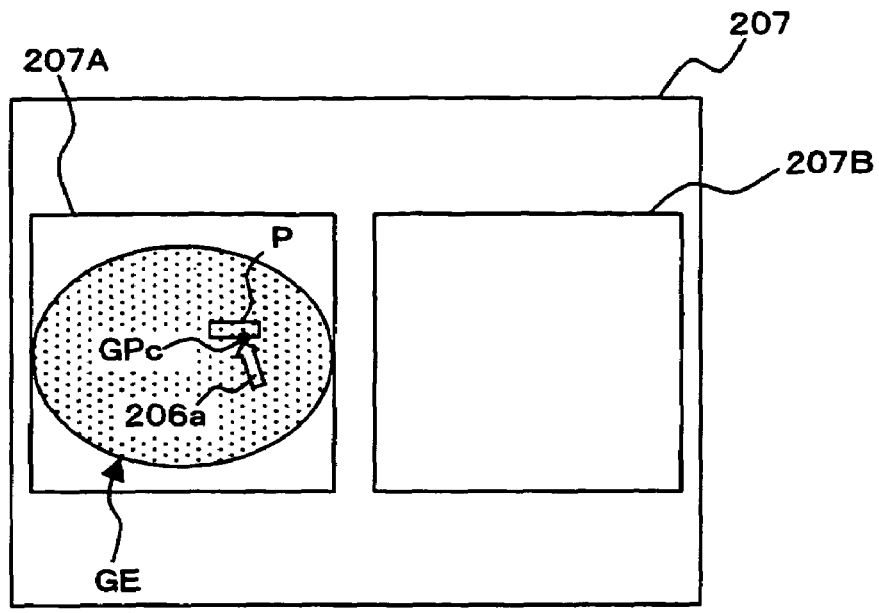
FIG. 40 is a schematic diagram representing one example of the display features of a fundus image in a favorable embodiment of the fundus observation device related to the present invention.

FIG. 40 represents one example of the display features of the deep area tomographic image GE. In the same figure, the deep area tomographic image GE is displayed in the fundus image display region 207A of the display 207. The examiner operates the mouse 206 to designate an attention region P (ref. FIG. 40) on the deep area tomographic image GE (S103).

Figure 41:
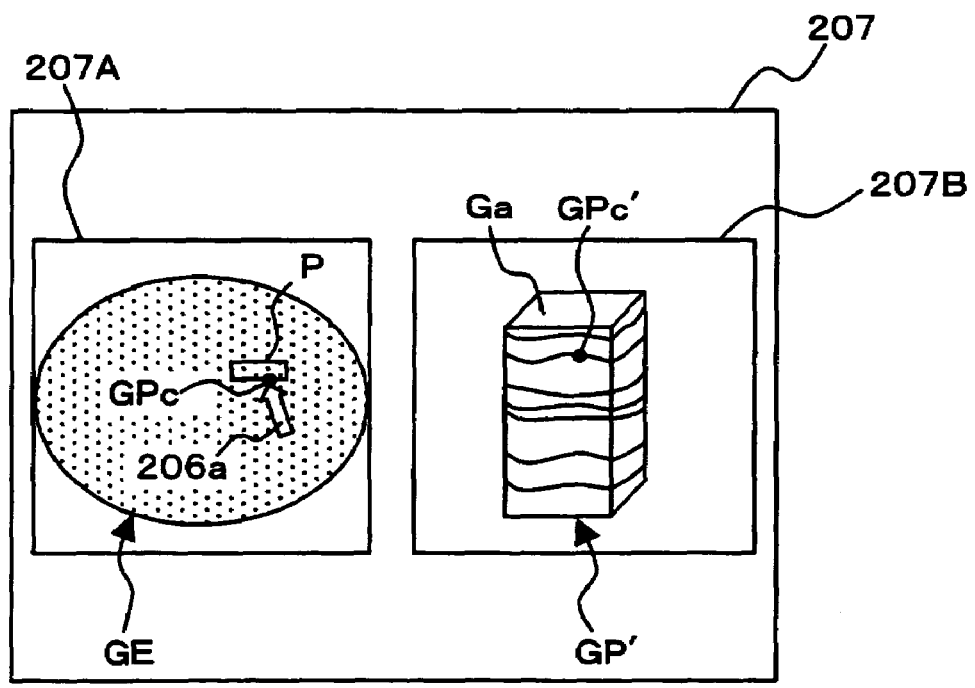
FIG. 41 is a schematic diagram representing one example of the display features of a fundus image in a favorable embodiment of the fundus observation device related to the present invention.

The controlling part 210 performs the same process as in Embodiment 1 to obtain the coordinate value of the designated attention region P to be sent to the image processing part 220. Based on the image data of the 3-dimensional image G, the image processing part 220 forms the image data of the 3-dimensional partial image GP' corresponding to this attention region P (S104). As shown in FIG. 41, the controlling part 210 displays this 3-dimensional partial image GP' on the tomographic image display region 207B (S105). Accordingly, on the display 207 the deep area tomographic image GE and the 3-dimensional partial image GP' are displayed in parallel.

Furthermore, as shown in FIG. 40, by moving the mouse pointer 206a to one point GPc on the deep area tomographic image GE and clicking, the examiner designates the one point GPc (S106). Upon receipt of the coordinate value (ξg,ηg) indicating the position of the designated one point GPc, by converting this, the controlling part 210 obtains (xh,yh,zh) in the xyz coordinate system (S170), and also stores this coordinate value (xh,yh,zh) in the designated position storing part 240 (S108).

Furthermore, the controlling part 210 displays the designated positional information GPc' indicating a position on the 3-dimensional partial image GP', that corresponds to the coordinate value (xh,yh,zh) that was obtained in step S107, so as to be overlapped with this 3-dimensional partial image GP' (S109). Then, based on the association of the xyz coordinate system explained in Embodiment 1 and the ξη coordinate system, the controlling part 210 converts the coordinate value (xh,yh,zh) to the ξη coordinate system (the ξη coordinate system defined in the tomographic image display region 207B) and displays the designated positional information GPc' on the 3-dimensional partial image GP' at a position to be specified by a coordinate value (ξg',ηg') that has been obtained accordingly. FIG. 41 represents one example of the display features of the designated positional information GPc' obtained as described.

Furthermore, the information ((coordinate value) xh,yh, zh) indicating the designated position (one point GPc) stored in the designated position storing part 240 in step S108 is read-out later when the image is observed, and the designated positional information (GPc') is displayed on the 3-dimensional partial image GP'.

In the present operational feature described above, the designated positional information is displayed only on the 3-dimensional partial image GP'; however, it may as also configured so as to display the designated positional information at a designated position (position of one point GPc) on the deep area tomographic image GE.

Moreover, in the present operational feature described above, after moving the mouse pointer 206a to a desired position on the deep area tomographic image GE by clicking, the designated position is confirmed (ref. step S106); however, for example, it may also be configured to execute the formation process as well as the display process of the 3-dimensional partial image GP', and the display process of the designated positional information following the movement of the mouse pointer 206a on the deep area tomographic image GE.

Furthermore, in the present operational feature, once the examiner specifically inputs an attention area P on the deep area tomographic image GE, a 3-dimensional partial image GP' corresponding to the attention region is formed and displayed; however, the present invention is not limited to this configuration. For example, it is configurable in a manner such that in response to the examiner having designated one point GPc on the deep area tomographic image, an attention region P including this one point GPc is set appropriately, and also the 3-dimensional partial image GP' corresponding to this an automatically set attention region P may be formed and displayed. The automatically setting process of this attention region P, for example, may be configured so as to read-out the saved information regarding the direction or the size (area) of the attention region P used in the past examination to be automatically set up. Moreover, it is also possible to configure in a manner such that the direction and the size of the attention region P is preset, and also the attention region P is set automatically, so as to arrange the designated one point GPc, for example, in the centroid.

Also, the designating position as one point GPc may be a contour region of the attention region P, or be the internal region.

According to the present operational feature, once the position (one point GPc) on the deep area tomographic image GE is designated, a 3-dimensional partial image including the designated position is formed and displayed parallel to the deep area tomographic image GE, at the same time the designated positional information (GPc') is displayed on the 3-dimensional partial image GP' at a position corresponding to the designated position, and therefore, the examiner may easily capture the relation of the position on the deep area tomographic image GE and the position on the 3-dimensional partial image GP'

[Modification Example]

The configuration described in detail thus far in Embodiment 2 is only an example of concrete configurations for executing the fundus observation device, the fundus image display device and the fundus observation program favorably. That is, the present invention is not limited to the configuration described above; however, for example, the optional modification explained below may be implemented appropriately.

As for the Operational Features 1 through 8 of the present embodiment described previously, it is to be configured to display the coordinate value of a designated one point on the display 207 so as to make it possible to change the coordinate value that has been displayed by using the user interface 230 (operational devices such as a mouse 206). Then, it is to be configured so as to display the designated positional information at a position on the display device 207 corresponding to the changed coordinate value.

The present modification example is explained for the case when it is applied to the Operational Feature 1 (the same with other operational features). The coordinate value (xa,ya) of one point La obtained in step S33 is made to be displayed on the display 207. This display process is executed by the controlling part 210. The examiner operates the mouse 206, etc. and changes the displayed coordinate value (xα,yα) to a desired coordinate value (xa,ya). The change information of the coordinate value is input from the user interface 230 to the controlling part 210.

Based on the coordinate value after the change (xα,yα), the controlling part 210 moves the designated positional information displayed at a designated position La on a fundus image Ef' to a position Lα. This process is executed by converting the coordinate value after the change (xα,yα) to a coordinate value (ξα,ηα) of the ξη coordinate system defined in the fundus image display region 207A, and by displaying the designated positional information at a position of a fundus image display region 207A, that is to be determined by this coordinate value (ξα,ηα).

Furthermore, based on the coordinate value after the change (xα,yα), the controlling part 210 moves a display position of a designated positional information La' displayed, overlapped with a tomographic image GL. In the same way as in step S35, this process may be executed by obtaining a position on the fundus image GL corresponding to the coordinate value (xα,yα), and by displaying a new designated positional information Lα' at the obtained position.

According to such a modification example, if the displayed coordinate value is changed by an operation by the examiner, and by changing the position of the designated positional information on the fundus image Ef', then designated positional information is displayed one after another on the tomographic image GL at a position corresponding to the position after the change, and thus the relation of the position on the fundus image Ef' and the position on the tomographic image GL may easily be captured.

The present modification example is particularly effective for the case when one wishes to designate a position in a more subtle way than designating operation of a position on a display image by using a mouse 206. That is, according to the present modification, by making a fine changes of the displayed coordinate value, a position slightly away from the originally designated position may precisely be designated, thus more detailed designating operation becomes possible.

Furthermore, the configuration explained in the modification example of Embodiment 1 may be applied to the present embodiment.

What is claimed is:

1. A fundus observation device comprising:
   a first image forming part configured to form a 2-dimensional image of the surface of a fundus oculi of an eye to be examined;
   a second image forming part configured to form a tomographic image of said fundus oculi;
   a display part having a first display region and a second display region;
   a controller configured to cause said display part to display said 2-dimensional image formed by said first image forming part on the first display region, to display said tomographic image formed by said second image forming part on the second display region, and also to display the cross-sectional position information indicating the cross-sectional position of said tomographic image displayed on the second display region, so as to be overlapped with said 2-dimensional image on said first display region; and
   an operating means,
   wherein when one point on said 2-dimensional image displayed on said first display region is designated by said operating means, said controller causes said display part to display the designated positional information indicating a position in the tomographic image corresponding to a position inside the eye to be examined indicated by the designated one point, so as to be overlapped with said tomographic image on the second display region.

2. The fundus observation device according to claim 1, wherein said controller,
   when said one point is designated by said operating means on an image displayed on said display part, is configured to cause said display part to display the coordinate value of said one point in a coordinate system predefined with respect to the image on said display part, and
   to change the position of said designated positional information to be displayed, in response to the change in the displayed coordinate value made by said operating means.

3. A fundus observation device comprising:
   a first image forming part configured to form a 2-dimensional image of the surface of a fundus oculi of an eye to be examined;
   a second image forming part configured to form a tomographic image of said fundus oculi;
   a display part having a first display region and a second display region;
   a controller configured to cause said display part to display said 2-dimensional image formed by said first image forming part on the first display region, to display said tomographic image formed by said second image forming part on the second display region, and also to display the cross-sectional position information indicating the cross-sectional position of said tomographic image displayed on the second display region, so as to be overlapped with said 2-dimensional image on said first display region; and
   an operating means,
   wherein when one point on said tomographic image displayed on the second display region is designated by said operating means, said controller is configured to cause said display part to display the designated positional information indicating a position in the two-dimensional image corresponding to a position inside the eye to be examined indicated by the designated one point, so as to be overlapped with said 2-dimensional image on the first display region.

4. The fundus observation device according to claim 3, wherein said controller,
   when said one point is designated by said operating means on an image displayed on said display part, is configured to cause said display part to display, the coordinate value of said one point in a coordinate system predefined with respect to the image, and
   changes the position of said designated positional information to be displayed on said display part, in response to the change in the displayed coordinate value made by said operating means.

5. A fundus observation device comprising:
   a first image forming part configured to form a 2-dimensional image of the surface of a fundus oculi of an eye to be examined;
   a second image forming part configured to form a tomographic image of said fundus oculi;
   a display part having a first display region and a second display region;
   a controller configured to cause said display part to display said 2-dimensional image formed by said first image forming part on the first display region, to display said tomographic image formed by said second image forming part on the second display region, and also to display the cross-sectional position information indicating the cross-sectional position of said tomographic image displayed on the second display region, so as to be overlapped with said 2-dimensional image on said first display region,
   wherein said second image forming part is an optical image measuring device comprising:
   a light source;
   an interference light generating means for splitting the light output from the light source into signal light directed towards said fundus oculi and reference light directed towards a reference object, and also for generating interference light by overlaying the signal light reflected at said fundus oculi and the reference light reflected at said reference object;
   a detecting means for outputting a detection signal upon receipt of said generated interference light; and
   a second image processing part configured to form a tomographic image of said fundus oculi, based on said detection signal that has been output, and
   wherein:
   said optical image measuring device further has a scanning means for scanning the incident position of said signal light with respect to said fundus oculi in a given main scanning direction and in a sub-scanning direction perpendicular to the main scanning direction respectively;

said second image processing part;

respectively forms a tomographic image along said main scanning direction at a plurality of positions that are different in said sub-scanning direction and forms a 3-dimensional image of said fundus oculi based on the plurality of formed tomographic images; and also forms an image of a partial region of the 3-dimensional image and a tomographic image at a boundary of the partial region, and forms a 3-dimensional partial image corresponding to said partial region based on the formed image of said partial region and the tomographic image of said boundary; and said controller;

displays the formed 3-dimensional partial image parallel to said 2-dimensional image on said display part, and also displays the cross-sectional position information indicating said boundary, so as to be overlapped with said 2-dimensional image.

6. The fundus observation device according to claim 5, wherein the fundus observation device further comprises an operating means for designating said partial region of said 3-dimensional image.

7. The fundus observation device according to claim 6, wherein:

said second image processing device, when one point on said 3-dimensional partial image displayed on said display part is designated by said operating means, forms a 2-dimensional image perpendicular to said depth direction at the depth in the depth direction at the designated one point of said fundus oculi;

said controller, and displays the 2-dimensional image formed at the depth of said one point parallel to said 3-dimensional partial image, and also displays the designated positional information indicating a position corresponding to said one point, so as to be overlapped with the 2-dimensional image at the depth of said one point.

8. The fundus observation device according to claim 7, wherein said controller, when said one point is designated by said operating means on an image displayed on said display part, displays the coordinate value of said one point in a coordinate system predefined with respect to the image on said display part, and changes the position of said designated positional information to be displayed on said display part, in response to the change in the displayed coordinate value made by said operating means.

9. The fundus observation device according to claim 7, further comprising a storing means, wherein said controller, when said one point is designated by said operating means on the image displayed on said display part, stores the coordinate value of said one point in a coordinate system predefined with respect to the image in said storing means so as to be read-out.

10. The fundus observation device according to claim 6, wherein:

said second image processing means forms a 2-dimensional image perpendicular to said depth direction at a given depth in the depth direction of said fundus oculi based on said 3-dimensional image;

said controller displays the formed 2-dimensional image at the given depth on said display part;

said second image processing part, when one point on the displayed 2-dimensional image at said given depth is designated by said operating part, forms a 3-dimensional partial image including the designated said one point based on said 3-dimensional image; and said controller displays the formed 3-dimensional partial image including said one point parallel to the 2-dimensional image at said given depth on said display part, and also displays the designated positional information indicating a position corresponding to said one point, so as to be overlapped with the 3-dimensional partial image including said one point.

11. The fundus observation device according to claim 10, wherein said controller, when said one point is designated by said operating means on an image displayed on said display part, displays the coordinate value of said one point in a coordinate system predefined with respect to the image on said display part, and changes the position of said designated positional information to be displayed on said display part, in response to the change in the displayed coordinate value made by said operating means.

12. The fundus observation device according to claim 10, further comprising a storing means, wherein said controller, when said one point is designated by said operating means on the image displayed on said display part, stores the coordinate value of said one point in a coordinate system predefined with respect to the image in said storing means so as to be read-out.

13. The fundus observation device according to claim 6, wherein, said second image processing part of said optical image measuring device, when a cross-sectional position is designated by said operating means on said 2-dimensional image displayed on said display part, forms a tomographic image at the designated cross-sectional position based on said 3-dimensional partial image, and said controller displays the formed tomographic image parallel to said 2-dimensional image on said display part, and also displays the cross-sectional position information indicating the designated cross-sectional position, so as to be overlapped with said 2-dimensional image.

14. The fundus observation device according to claim 6, wherein said controller, when one point on said 2-dimensional image displayed on said display part is designated by said operating means, displays the designated positional information indicating a position corresponding to the designated one point, so as to be overlapped with said 3-dimensional image.

15. The fundus observation device according to claim 6, wherein said controller, when one point on said 3-dimensional image displayed on said display part is designated by said operating means, displays the designated positional information indicating a position corresponding to the designated one point, so as to be overlapped with said 2-dimensional image.

16. A fundus observation device comprising:

a first image forming part configured to form a 2-dimensional image of the surface of a fundus oculi of an eye to be examined;

a second image forming part configured to form a tomographic image of said fundus oculi;

a display part having a first display region and a second display region;

a controller configured to cause said display part to display said 2-dimensional image formed by said first image forming part on the first display region, to display said tomographic image formed by said second image forming part on the second display region, and also to display the cross-sectional position information indicating the cross-sectional position of said tomographic image displayed on the second display region, so as to be overlapped with said 2-dimensional image on said first display region, wherein, said first image forming part is a fundus camera comprising:

an illuminating optical system for emitting illumination light onto said fundus oculi;

a photographing optical system for receiving the fundus reflection light of said emitted illumination light; and a first image processing part configured to form a 2-dimensional image of the surface of said fundus oculi based on said received fundus reflection light, and said second image forming part is an optical image measuring device comprising:

a light source;

an interference light generating means for splitting the light output from the light source into signal light directed towards said fundus oculi through a part of the optical path of the photographing optical system of said fundus camera and into reference light directed towards a reference object, and also for generating interference light by overlaying the signal light reflected at said fundus oculi and guided through a part of said optical oath and the reference light reflected at said reference object;

a detecting means for outputting a detection signal upon receipt of said generated interference light; and a second image processing part configured to form a tomographic image of said fundus oculi, based on said detection signal that has been output, said fundus observation device further comprising an operating means, wherein:

said optical image measuring device further has a scanning means for scanning the incident position of said signal light with respect to said fundus oculi in a given main scanning direction and in a sub-scanning direction perpendicular to the main scanning direction respectively;

said second image processing device respectively forms a tomographic image along said main scanning direction at a plurality of positions that are different in said sub-scanning direction and forms a 3-dimensional image of said fundus oculi based on the plurality of tomographic images that have been formed, and also when a cross-sectional position is designated by said operating means on said 2-dimensional image displayed on said display part, forms a tomographic image at the designated cross-sectional position based on said 3-dimensional image; and said controller displays the tomographic image at the designated cross-sectional position parallel to said 2-dimensional image, and also displays the cross-sectional position information indicating the designated cross-sectional position, so as to be overlapped with said 2-dimensional image.

17. The fundus observation device according to claim 16, wherein:

said second image processing part, when one point on said tomographic image displayed on said display part is designated by said operating means, forms a 2-dimensional image perpendicular to said depth direction at a depth in the depth direction at the designated one point of said fundus oculi; and said controller displays the 2-dimensional image formed at the depth of said one point parallel to said tomographic image, and also displays the designated positional information indicating a position corresponding to said one point, so as to be overlapped with the 2-dimensional image at the depth of said one point.

18. The fundus observation device according to claim 17, wherein said controller, when said one point is designated by said operating means on an image displayed on said display part, displays the coordinate value of said one point in a coordinate system predefined with respect to the image on said display part, and changes the position of said designated positional information to be displayed on said display part, in response to the change in the displayed coordinate value made by said operating means.

19. The fundus observation device according to claim 16, wherein:

said second image processing part forms a 2-dimensional image perpendicular to said depth direction at a given depth in the depth direction of said fundus oculi based on said 3-dimensional image;

said controller displays the 2-dimensional image formed at the given depth on said display part;

said second image processing means, when one point on the displayed 2-dimensional image at said given depth is designated by said operating means, forms a tomographic image including the designated said one point based on said 3-dimensional image; and said controller displays the formed tomographic image including said one point, parallel to the 2-dimensional image at said given depth on said display part, and also displays the designated positional information indicating a position corresponding to said one point, so as to be overlapped with the tomographic image including said one point.

20. The fundus observation device according to claim 19, wherein said controller, when said one point is designated by said operating means on an image displayed on said display part, displays the coordinate value of said one point in a coordinate system predefined with respect to the image on said display part, and changes the position of said designated positional information to be displayed on said display part, in response to the change in the displayed coordinate value made by said operating means.

21. The fundus observation device according to claim 16, wherein:

said optical image measuring device further has a scanning means for scanning the incident position of said signal light with respect to said fundus oculi in a given main scanning direction and in a sub-scanning direction perpendicular to the main scanning direction respectively;

said second image processing device
respectively forms a tomographic image along said main scanning direction at a plurality of positions that are different in said sub-scanning direction and forms a 3-dimensional image of said fundus oculi based on the plurality of formed tomographic images; and also
forms an image of a partial region of the 3-dimensional image and a tomographic image at a boundary of the partial region, and forms a 3-dimensional partial image corresponding to said partial region based on the formed image of said partial region and the tomographic image of said boundary; and said controller
displays the formed 3-dimensional partial image parallel to said 2-dimensional image on said display part, and also
displays the cross-sectional position information indicating said boundary, so as to be overlapped with said 2-dimensional image.

22. The fundus observation device according to claim 21, wherein the fundus observation device further comprises an operating means for designating said partial region of said 3-dimensional image.

23. The fundus observation device according to claim 22, wherein:
said second image processing part, when one point on said 3-dimensional partial image displayed on said display part is designated by said operating means, forms a 2-dimensional image perpendicular to said depth direction at the depth in the depth direction at the designated one point of said fundus oculi;
said controller, and
displays the 2-dimensional image formed at the depth of said one point parallel to said 3-dimensional partial image, and also
displays the designated positional information indicating a position corresponding to said one point, so as to be overlapped with the 2-dimensional image at the depth of said one point.

24. The fundus observation device according to claim 23, wherein
said,
when said one point is designated by said operating means on an image displayed on said display part, displays the coordinate value of said one point in a coordinate system predefined with respect to the image on said display part, and
changes the position of said designated positional information to be displayed on said display part, in response to the change in the displayed coordinate value made by said operating means.

25. The fundus observation device according to claim 23, further comprising a storing means,
wherein said controller, when said one point is designated by said operating means on the image displayed on said display part, stores the coordinate value of said one point in a coordinate system predefined with respect to the image in said storing means so as to be read-out.

26. The fundus observation device according to claim 22, wherein:
said second image processing part forms a 2-dimensional image perpendicular to said depth direction at a given depth in the depth direction of said fundus oculi based on said 3-dimensional image;
said controller displays the formed 2-dimensional image at the given depth on said display part;

said second image processing means, when one point on the displayed 2-dimensional image at said given depth is designated by said operating means, forms a 3-dimensional partial image including the designated said one point based on said 3-dimensional image; and
said controller
displays the formed 3-dimensional partial image including said one point parallel to the 2-dimensional image at said given depth on said display part, and also
displays the designated positional information indicating a position corresponding to said one point, so as to be overlapped with the 3-dimensional partial image including said one point.

27. The fundus observation device according to claim 26, wherein
said controller,
when said one point is designated by said operating means on an image displayed on said display part, displays the coordinate value of said one point in a coordinate system predefined with respect to the image on said display part, and
changes the position of said designated positional information to be displayed on said display part, in response to the change in the displayed coordinate value made by said operating means.

28. The fundus observation device according to claim 26, further comprising a storing means,
wherein said controller, when said one point is designated by said operating means on the image displayed on said display part, stores the coordinate value of said one point in a coordinate system predefined with respect to the image in said storing means so as to be read-out.

29. The fundus observation device according to claim 22, wherein,
said second image processing part of said optical image measuring device, when a cross-sectional position is designated by said operating means on said 2-dimensional image displayed on said display part, forms a tomographic image at the designated cross-sectional position based on said 3-dimensional partial image, and
said controller
displays the formed tomographic image parallel to said 2-dimensional image on said display part, and also
displays the cross-sectional position information indicating the designated cross-sectional position, so as to be overlapped with said 2-dimensional image.

30. The fundus observation device according to claim 22, wherein said controller, when one point on said 2-dimensional image displayed on said display part is designated by said operating means, displays the designated positional information indicating a position corresponding to the designated one point, so as to be overlapped with said 3-dimensional image.

31. The fundus observation device according to claim 22, wherein said controller, when one point on said 3-dimensional image displayed on said display part is designated by said operating means, displays the designated positional information indicating a position corresponding to the designated one point, so as to be overlapped with said 2-dimensional image.

32. A fundus image display device connected to a first image forming part configured to form a 2-dimensional image of the surface of a fundus oculi of an eye to be examined and to a second image forming part configured to form a tomographic image of said fundus oculi;
comprising:
a display part;

a control part configured to display said 2-dimensional image formed by said first image forming part parallel to said tomographic image formed by said second image forming part on said display part, and also to display the cross-sectional position information indicating the cross-sectional position of said tomographic image of the surface of said fundus oculi, so as to be overlapped with said 2-dimensional image; and an operating means, wherein said controller, when one point on said 2-dimensional image displayed on said display part is designated by said operating means, displays the designated positional information indicating a position corresponding to the designated one point, so as to be overlapped with said tomographic image.

33. The fundus image display device according to claim 32, further comprising:

an operating means, wherein said controller, when one point on said tomographic image displayed on said display part is designated by said operating means, displays the designated positional information indicating a position corresponding to the designated one point, so as to be overlapped with said 2-dimensional image.

34. A fundus observation program wherein a computer, which is connected to a first image forming part configured to form a 2-dimensional image of the surface of a fundus oculi of an eye to be examined and to a second image forming part configured to form a tomographic image of said fundus oculi, and which is equipped with a display part, is made to function as a controller configured to display said 2-dimensional image formed by said first image forming part parallel to said tomographic image formed by said second image forming part on said display part, and also to display the cross-sectional position information indicating the cross-sectional position of said tomographic image of the surface of said fundus oculi, so as to be overlapped with said 2-dimensional image, and wherein said computer further comprises an operating means, and when one point on said 2-dimensional image displayed on said display part is designated by said operating means, said controller is made to function to display the designated positional information indicating a position corresponding to the designated one point, so as to be overlapped with said tomographic image.

35. The fundus observation program according to claim 34, wherein said computer further comprises an operating means, and when one point on said tomographic image displayed on said display part is designated by said operating means, said controller is made to function to display the designated positional information indicating a position corresponding to the designated one point, so to be overlapped with said 2-dimensional image.

36. The fundus observation device according to claim 1, wherein:

said optical image measuring device further has a scanner configured to scan the incident position of said signal light with respect to said fundus oculi in a given main scanning direction and in a sub-scanning direction perpendicular to the main scanning direction respectively;

said second image processing part respectively forms tomographic images along said main scanning direction at a plurality of positions that are different in said sub-scanning direction and forms a 3-dimensional image of said fundus oculi based on the plurality of formed tomographic images; and also forms a tomographic image of a cross section including a point designed by the operating means, on the two-dimensional image displayed by the display part, based on the three-dimensional image; and said controller is configured to cause said display part to display said 2-dimensional image on the first display region and said 3-dimensional image on the second display region, and also to display the designed positional information to overlap with the tomographic image on the second display region.

* * * * *